United States Patent [19]

Glamkowski et al.

[11] Patent Number: 4,723,007
[45] Date of Patent: Feb. 2, 1988

[54] BENZOPYRROLOBENZODIAZEPINES AND QUINOBENZODIAZEPINES

[75] Inventors: Edward J. Glamkowski, Warren; Yulin Chiang, Convent Station, both of N.J.

[73] Assignee: Hoechst-Roussel Pharmaceuticals Inc., Somerville, N.J.

[21] Appl. No.: 929,705

[22] Filed: Nov. 12, 1986

Related U.S. Application Data

[60] Division of Ser. No. 770,046, Aug. 28, 1985, Pat. No. 4,663,453, which is a continuation-in-part of Ser. No. 639,569, Aug. 10, 1984, abandoned, which is a continuation-in-part of Ser. No. 495,569, May 18, 1983, abandoned.

[51] Int. Cl.$^4$ .................. C07D 487/02; C07D 215/00
[52] U.S. Cl. .................................. 540/360; 546/165; 548/511; 548/490
[58] Field of Search ............... 544/360; 546/165; 548/490, 511

[56] References Cited

U.S. PATENT DOCUMENTS

| | | | |
|---|---|---|---|
| 4,186,199 | 1/1980 | Glamkowski et al. | 514/218 |
| 4,192,874 | 3/1980 | Glamkowski et al. | 514/218 |
| 4,438,120 | 3/1984 | Rajagopalan | 514/218 |
| 4,447,361 | 5/1984 | Taylor | 514/218 |

OTHER PUBLICATIONS

Hoechst-Roussel Pharmaceuticals, Inc. CA 102-166786k.

Primary Examiner—Donald G. Daus
Assistant Examiner—Cecilia Shen
Attorney, Agent, or Firm—Raymond R. Wittekind

[57] ABSTRACT

The invention relates to benzopyrrolobenzodiazepines and quinobenzodiazepines of the formula

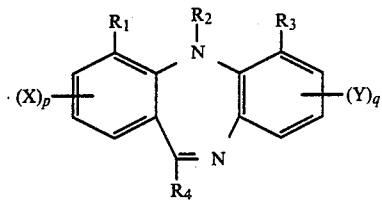

where X and Y may be the same or different and each is hydrogen, halogen, $CF_3$, lower alkyl, lower alkoxy, lower alkylthio and lower alkylsulfonyl, p and q are independently 1 or 2; $R_1$ is hydrogen when $R_2$ is bonded to $R_3$ to form a $-(CH_2)_m-CH_2-$ group or a $-CH=CH-$ group; $R_3$ is hydrogen when $R_1$ is bonded to $R_2$ to form a $-(CH_2)_m-CH_2-$ group or a $-CH=CH-$ group; m is 1 or 2; $R_4$ is $NR_5R_6$ wherein $R_5$ is hydrogen or lower alkyl and $R_6$ is hydrogen, lower alkyl or a group of the formula $(CH_2)_nNR_7R_8$ wherein $R_7$ and $R_8$ are lower alkyl, and n is 2 or 3,

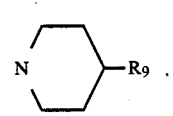

wherein $R_9$ is lower alkyl,

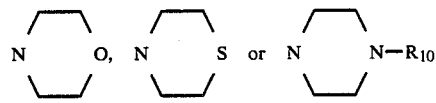

wherein $R_{10}$ is $CH_2CH_2OH$, lower alkyl, phenyl, phenyl substituted by halogen, $CF_3$, lower alkyl, lower alkoxy or lower alkylthio, benzyl, benzyl in which the phenyl group is substituted by halogen, $CF_3$, lower alkyl, lower alkoxy or lower alkylthio or $CO_2R_{11}$ wherein $R_{11}$ is lower alkyl, or a pharmaceutically acceptable acid salt thereof.

20 Claims, No Drawings

4,723,007

BENZOPYRROLOBENZODIAZEPINES AND QUINOBENZODIAZEPINES

This is a division of application Ser. No. 770,046, filed Aug. 28, 1985, now U.S. Pat. No. 4,663,453 which is a continuation-in-part of application Ser. No. 639,569, filed Aug. 10, 1984, now abandoned, which is a continuation-in-part of application Ser. No. 495,569, filed May 18, 1983, now abandoned.

To the best of our knowledge the compounds of the present invention have not heretofore been described or suggested.

U.S. Pat. No. 4,186,199 discloses compounds of the formula

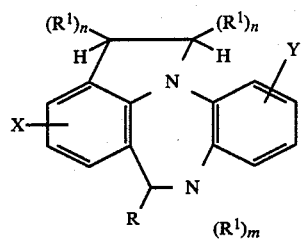

where X, Y, R and $R^1$ are various substituents and n and m are 0 or 1; which compounds have analgesic and anti-inflammatory activity. These compounds are substantially different from those of the present invention.

The compounds of the present invention have the general formula

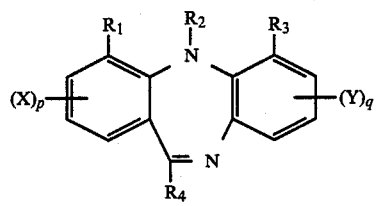

(I)

wherein X and Y may be the same or different and each is hydrogen, halogen, $CF_3$, lower alkyl, lower alkoxy, lower alkylthio or lower alkylsulfonyl, p and q are independently 1 or 2; $R_1$ is hydrogen when $R_2$ is bonded to $R_3$ to form a $—(CH_2)_m—CH_2—$ group or a $—CH=CH—$ group; $R_3$ is hydrogen when $R_1$ is bonded to $R_2$ to form a $—(CH_2)_m—CH_2—$ group or a $—CH=CH—$ group; m is 1 or 2; $R_4$ is $NR_5R_6$ wherein $R_5$ is hydrogen or lower alkyl and $R_6$ is hydrogen, lower alkyl, or a group of the formula $(CH_2)_nNR_7R_8$ wherein $R_7$ and $R_8$ are lower alkyl, 2 and n is 2 or 3,

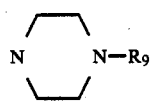

wherein $R_9$ is lower alkyl,

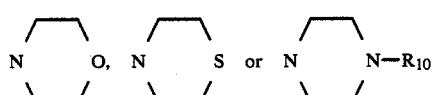

wherein $R_{10}$ is $CH_2CH_2OH$, lower alkyl, phenyl, phenyl substituted by halogen, $CF_3$, lower alkyl, lower alkoxy or lower alkylthio, benzyl, benzyl in which the phenyl group is substituted by halogen, $CF_3$, lower alkyl, lower alkoxy or lower alkylthio, or $CO_2R_{11}$ wherein $R_{11}$ is lower alkyl; or a pharmaceutically acceptable acid salt thereof.

Encompassed by the present invention are compounds of the formulas:

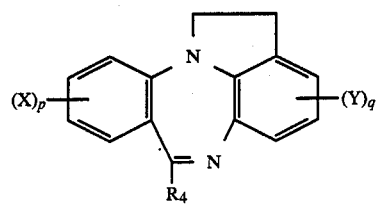

(Ia)

wherein $R_4$, X, Y, p and q are as previously defined or a pharmaceutically acceptable acid addition salt thereof.

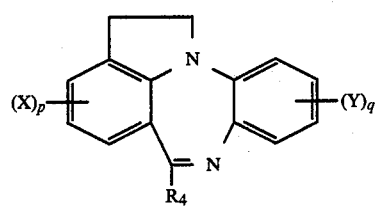

(Ib)

wherein $R_4$, X, Y, p and q are as previously defined or a pharmaceutically acceptable acid addition salt thereof.

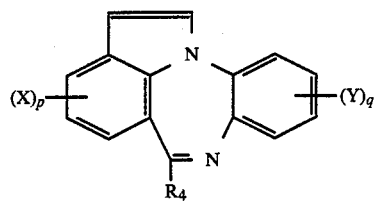

(Ic)

wherein $R_4$, X, Y, p and q are as previously defined or a pharmaceutically acceptable acid addition salt thereof.

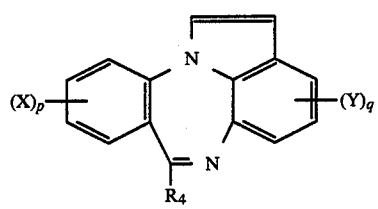

(Id)

wherein $R_4$, X, Y, p and q are as previously defined or a pharmaceutically acceptable acid addition salt thereof.

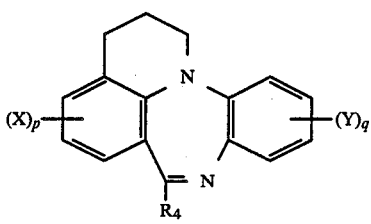

(Ie)

wherein $R_4$, X, Y, p and q are as previously defined or a pharmaceutically acceptable acid addition salt thereof.

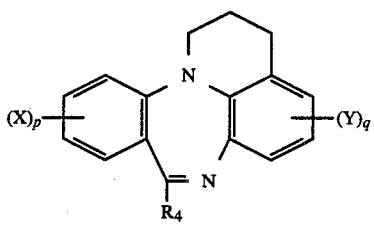

(If)

wherein $R_4$, X, Y, p and q are as previously defined or a pharmaceutically acceptable acid addition salt thereof.

More specifically, included in the present invention are compounds of formulas wherein (a) $R_4$ is $NR_5R_6$ wherein $R_5R_6$ are as previously defined or a group of the formula $(CH_2)_nNR_7R_8$ wherein $R_7$, $R_8$ and n are as previously defined; (b) $R_4$ is

wherein $R_9$ and $R_{10}$ are as previously defined; and (c) $R_4$ is

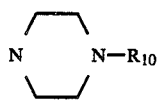

wherein $R_{10}$ is as previously defined.

Also encompassed by the present invention are compounds of the formula

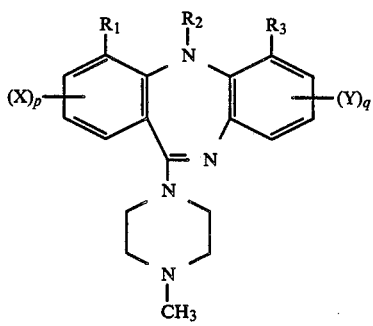

(Ig)

where X and Y may be the same or different and each is hydrogen, halogen, $CF_3$, lower alkyl, lower alkoxy, lower alkylthio and lower alkylsulfonyl, p and q are independently 1 or 2; $R_1$ is hydrogen when $R_2$ is bonded to $R_3$ to form a $-CH_2CH_2-$ group; and $R_3$ is hydrogen when $R_2$ is bonded to $R_1$ to form a $-CH_2CH_2-$ group; and the pharmaceutically acceptable acid addition salts thereof.

Preferred embodiments of the subject invention are those wherein the compounds have the formula:

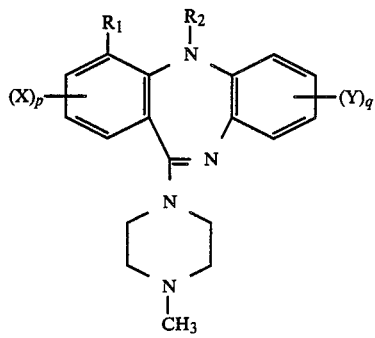

Most preferred are compounds Ia where Y and X are independently $CH_3$ or Br.

In the above definitions the term "lower" means the group it is describing contains from 1 to 6 carbon atoms. The term "alkyl" refers to a straight or branched chain hydrocarbon containing no unsaturation, e.g. methyl, ethyl, isopropyl, 2-butyl, neopentyl, n-hexyl, etc.; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc.; the term "halogen" refers to a member of the family consisting of fluorine, chlorine, bromine and iodine; the term "lower alkylthio" refers to a monovalent substituent having the formula lower alkyl—S—; and the term "lower alkylsulfonyl" refers to a monovalent substitutent having the formula lower alkyl—$SO_2$—.

The compounds of the present invention are prepared in the following manner. The substituents X, Y, $R_1$, $R_2$, $R_3$, p and q are as defined above unless indicated otherwise. Compound I wherein $R_1$ is hydrogen and $R_2$ is bonded to $R_3$ to form a $-CH_2CH_2-$ group, as depicted by formula Ia'

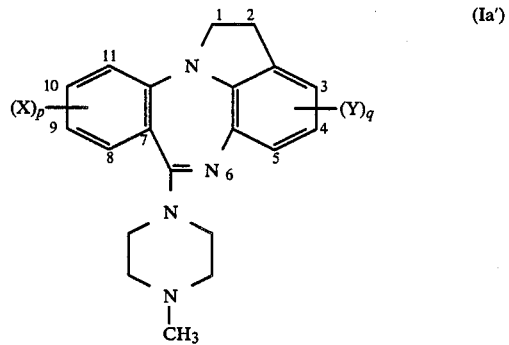

(Ia')

is prepared by reacting a selected indoline of formula IIa.

with a compound of the formula

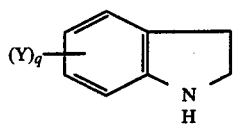

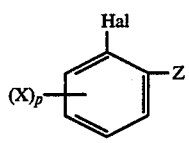 (III)

where Hal is a halogen and Z is selected from $$-\overset{O}{\underset{\|}{C}}-NH_2, \quad -\overset{O}{\underset{\|}{C}}-OCH_3,$$

and —CN. Compound IIa is reacted with Compound III under conventional nucleophilic reaction conditions, typically in the presence of a base, e.g. NaH, KOC(CH$_3$)$_3$, C$_6$H$_5$Li, etc. either alone or in a solvent, e.g. dimethylsulfoxide (MDSO), dimethylformamide (DMF), etc., at a temperature of 0° C. to 100° C. for 0.5 to 24 hours, to form compound IV of the formula

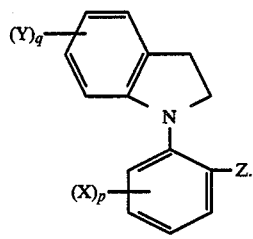 (IV)

Compound IV in turn is subjected to a conventional aromaic nitration by means of a conventional nitrating agent such as acetyl nitrate, typically by reacting Compound IV with silver nitrate and acetyl chloride in the presence of acetonitrile, to form a nitro-substituted compound of the formula

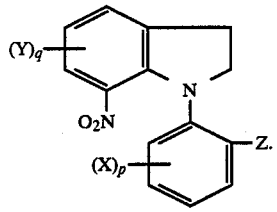 (V)

Compound V is then reduced in a conventional manner, such as catalytically, e.g., with hydrogen and Pd on carbon catalyst, Pt on carbon, with metal salts, e.g. stannous chloride/hydrochloric acid, etc. to form a compound of the formula

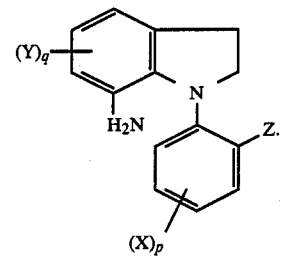 (VI)

When halogen is present at X or Y, it is preferred to use 1% Pt on carbon as the catalyst to avoid the possibility of hydrogenolysis of the nuclear halogen substituent.

Compound VI is subjected to a condensation or cyclization by reaction with a conventional agent, e.g. SiO$_2$, P$_2$O$_5$ and heating at 100° C. to 200° C. for 0.5 to 24 hours to form a benzodiazepinone of the formula

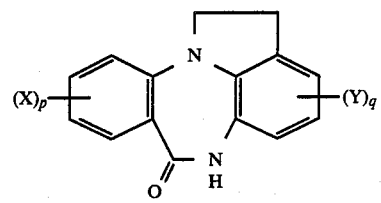 (VIIa)

when Z is $$-\overset{O}{\underset{\|}{C}}-NH_2 \text{ or } -\overset{O}{\underset{\|}{C}}-OCH_3$$

and a compound of the formula

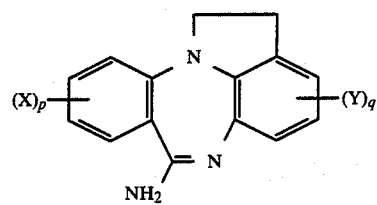 (VIIb)

when Z is —CN. Compound VII(a) or (b) in turn is reacted with N-methyl piperazine,

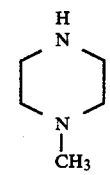

under conventional nucleophilic reaction conditions, typically in the presence of a Lewis acid, e.g. TiCl$_4$, AlCl$_3$, etc. to form Compound Ia' of the invention.

Alternatively, the benzodiazepinone VIIa may be converted to Compound VIII, that is either an imino halide, as for example, an imino chloride with phosphorous pentachloride, or an iminomethylmercaptan, first by reaction with phosphorus pentasulfide in pyridine, then reaction of the resulting benzodiazepine-thione with methyl iodide.

(VIII)

where R is halogen or —SCH$_3$. Compound VIII in turn is reacted with N-methyl piperazine under conventional nucleophilic conditions in an inert solvent to form compound Ia' of the invention.

Compound I where R$_1$ and R$_2$ are bonded to form a —CH$_2$CH$_2$— group, as depicted by formula Ib'

(Ib')

is prepared by reacting selected indoline IIb with a halo substituted nitrobenzene of the formula (IIb)

(IX)

where Hal is halogen. The reaction is carried out under conventional nucleophilic reaction conditions. The reaction can be carried out using an excess of indoline to serve as a base as well as reactant. The reaction can be carried out without a solvent by heating the two reactants from 50° C. to 200° C. or in the presence of an inert solvent, e.g. benzene, toluene, xylene, dimethylformamide, etc., at a temperature of 20° C. to the boiling point of the solvent. The reactio can be carried out typically in the presence of a base, e.g., NaH, KOC(CH$_3$)$_3$, n-butyllithium, etc. and an inert solvent, e.g. dimethylformamide, dimethylsulfoxide, etc., at a temperature of 0° C. to 150° C. for 0.5 to 24 hours, to form compound (X) having the formula

X

Compound X in turn is reduced, in the manner previously described, to form compound (XI)

XI

Amino-substituted compound XI is converted to a urea XII by reaction with 4-methyl-1-piperazine carbonyl chloride, Under conventional acylation conditions, typically in the presence of a base, e.g., K$_2$CO$_3$, NaHCO$_3$, collidine, etc. in an inert solvent, e.g. chloroform, dimethylformamide, toluene, etc., at a temperature of 0° C. to 100° C. for 0.5 to 48 hours to form the urea (XII)

Urea XII is subjected to the cyclization reported in U.S. Pat. No. 4,186,199, which involves treating Compound XII with POCl$_3$ usually in an inert atmosphere at temperatures from 20° C. up to the reflux temperature of the reaction mixture, with or without solvent, to form compound Ib' of the invention.

The compounds of the present invention are also prepared by the processes described in Reaction Schemes A and B.

To prepare 6-substituted-1,2-dihydrobenzo[b]pyrrolo[3,2,1-jk][1,4]-benzodiazepines of formula Ib, 1-(aminophenyl)indoline of formula XI, the preparation of which is hereinbeforedescribed, is converted to 1-(ureidophenyl)indoline XV, either directly or via 1-(phenoxycarbonyl)indoline XIV, which is cyclized to (Ib) or a mixture of (Ib) and 1,2-dihydrobenzo[b]pyrrolo[3,2,1-jk]benzodiazepin-6-one (XVI), the latter of which, i.e., compound (XVI), is condensed with amines R$_5$R$_6$NH (XVIII) wherein R$_5$ and R$_6$ are as hereinbeforedefined to provide compounds of formula (Ib). See Reaction Scheme A.

The conversion of 1-(aminophenyl)indoline (XI) to urea (XV) is accomplished by treating (XI) with a carbonyl halide of thie formula $R_4COHal$ (XIX) wherein $R_4$ and Hal are as hereinbeforedefined in the presence of a suitable base and a suitable solvent, essentially by the procedure hereinbeforedescribed for the preparation of compound (XII). Included among suitable bases are alkali metal carbonates and bicarbonates, e.g., lithium, sodium and potassium carbonates, and lithium, sodium and potassium bicarbonates. Included among suitable solvents are halocarbons, e.g., dichloromethane, trichloromethane, tetrachloromethane, dichloroethane, and the like. A combination of sodium bicarbonate or potassium carbonate and trichloromethane is preferred. The temperature at which the conversion is effected is not narrowly critical. To promote a reasonable rate of conversion, an elevated temperature, e.g., the reflux temperature of the reaction mixture, may be employed.

Alternatively, 1-(aminophenyl)indoline (XI) is treated with a haloformate of the formula $R_{16}OCOHal$ (XX) in the presence of a suitable base, e.g., a tertiary amine such as trimethyl-, triethyl-, tripropylamine, and the like, or a heterocyclic amine such as pyridine, lutidine, collidine, and the like, and a suitable solvent, e.g., a halocarbon such as dichloromethane, trichloromethane and the like, preferably at ambient temperature, to provide carbamate (XIV), which, in turn, is treated with $R_5R_6NH$ (XVIII) in a suitable solvent, e.g., an aromatic solvent such as benzene, toluene, xylene, and the like, or a halocarbon such as dichloromethane, trichloromethane, and the like to afford (XV). While these reactions are generally conducted at ambient temperature, elevated temperatures such as the reflux temperature of the reaction medium may be employed to establish a reasonable rate of reaction.

The cyclization of urea (XV) to 1,2-dihydrobenzo[b]pyrrolo[3,2,1-jk][1,4]benzodiazepine (Ib) is conveniently performed by contacting urea (XV) with phosphorus oxychloride, phosphorous trichloride or tribromide, or polyphosphoric acid ethyl ester at a temperature within the range of about ambient temperature to the reflux temperature of the reaction mixture. A temperature about the reflux temperature of the reaction mixture is preferred. The cyclization proceeds readily in the absence of a solvent. A suitable solvent may be employed, however. Among suitable solvents, there may be mentioned aromatic solvents such as, for example, benzene, toluene, xylene, and the like, and halocarbons such as dichloromethane, trichloromethane and the like.

When polyphosphoric acid ethyl ester is utilized as the catalyst in the cyclization step (XV→Ib), in addition to pyrrolobenzodiazepine (Ib), pyrrolobenzodiazepin-6-one (XVI) is formed and isolated. For example, treatment of (XV) wherein X is chloro with polyphosphoric acid ethyl ester in a halocarbon solvent such as 1,2-dichloroethane at a reaction temperature of about 75° C. affords a mixture of the diazepine Ib wherein X is chloro and diazepinone (XVI) wherein X is chloro.

Diazepinones (XVI) are also prepared by hydrolysis of diazepines (Ib). Thus, treatment of (Ib) with an aqueous mineral acid such as hydrochloric acid, sulfuric acid, nitric acid, phosphoric acid, and the like at a reaction temperature between about ambient temperature and the reflux temperature of the reaction medium furnishes lactam XVI, which is useful as a precursor for the synthesis of diazepines, i.e., diazepines of formula (Ib) having substituents $R_4$ other than those of the starting material for the hydrolysis (Ib→XVI).

Thus, treatment of diazepinone (XVI) with amines of the formula $R_5R_6NH$ (XVIII) wherein $R_5$ and $R_6$ are as hereinbeforedescribed in the presence of a Lewis acid and an aromatic solvent affords diazepines (Ib) wherein $R_4$ is as hereinbefore described. Lewis acids include titanium tetrachloride, aluminum chloride, and the like. Aromatic solvents include benzene, toluene, xylene, mesitylene, and the like. Titanium tetrachloride is the preferred Lewis acid. Toluene is the preferred aromatic solvent. The temperature at which the conversion of (XVI) to (Ib) is performed is not critical. While the reaction proceeds readily at moderate temperatures, elevated temperatures up to and including the reflux temperature of the reaction system may be employed to promote the reaction. A reaction temperature of about the reflux temperature of the reaction medium is preferred.

To provide entry into the benzo[b]pyrrolo[3,2,1-jk][1,4]benzodiazepine series, i.e., to synthesize compounds of formula (Ic), one dehydrogenates a 1,2-dihydrobenzo[b]pyrrolo[3,2,1-jk]benzodiazepin-6-one (XVI) to a benzo[b]pyrrolo[3,2,1jk]benzodiazepin-6-one XVII and condenses the diazepin-6-one (XVII), so obtained, with amines of the formula $R_5R_6NH$ (XVIII). The dehydrogenation is accomplished by treating the dihydro compound XVI with an oxidizing agent, such as, for example, 2,3,5,6-tetrachlorobenzoquinone, 2,3-dichloro-5,6-dicyanobenzoquinone, and the like, or manganese dioxide, in a suitable solvent. For the quinone oxidation, aromatic hydrocarbons, e.g., benzene, toluene, xylene, and the like, are suitable, xylene being preferred. For the manganese dioxide oxidation, halocarbons, e.g., dichloromethane, trichloromethane, dichloroethane, and the like are appropriate, trichloromethane being preferred. While the temperature at which one conducts the dehydrogenation reaction is not critical, it is desirable to perform it at the reflux temperature of the reaction mixture. The condensation of lactam (XVII) with amines of the formula $R_5R_6NH$ (XVIII) is conveniently carried out by the hereinbeforedescribed processes for the conversion of lactam (XVI) to amidine (Ib).

In the alternative, benzo[b]pyrrolo[3,2,1-jk]benzodiazepine (Ic) is obtained by dehydrogenating 1,2-dihydrobenzo[b]pyrrolo[3,2,1-jk]benzodiazepine (Ib) with a benzoquinone or manganese dioxide by the hereinbeforedescribed procedure for the synthesis of (XVII) from (XVI).

To also gain entry into the 1,2-dihydrobenzo[c]pyrrolo[1,2,3-ef][1,5]-benzodiazepine series, the cyano group of a 1-(2-cyanophenyl)indoline of formula (V), the preparation of which is hereinbeforedescribed, is hydrolyzed to a 1-(2-carboxyphenyl)indoline of formula (XXI), which is converted to the 1,2-dihydrobenzo[c]pyrrolo[1,2,3-ef][1,5]benzodiazepin-7-one (VIIa) and then condensed with an amine of the formula $R_5R_6NH$ (XVIII) to furnish benzodiazepines of formula (Ia).

The hydrolysis is conveniently carried out by treating the nitrile of formula V with an alkali metal or alkaline earth hydroxide such as, for example, lithium, sodium, or potassium hydroxide, or calcium or magnesium hydroxide, in an alkanol such as, for example, methanol, ethanol, 2-propanol, 1-butanol, 2-pentanol, 3-hexanol, and the like, or a glycol such as, for example, ethylene glycol, propylene glycol, and the like. Potassium hydroxide and ethylene glycol are preferred. The hydrolysis proceeds at a convenient rate at the reflux temperature of the reaction medium. Reduced temperatures may be used to effect the transformation of nitrile (V) to carboxylic acid (XXI).

The conversion of the 1-(2-carboxyphenyl)indoline (XXI) to the benzodiazepinone (VIIa) is performed by reducing the nitro group which hydrogen in the presence of a metal catalyst in a suitable solvent. Among metal catalysts, there may be mentioned platinum, palladium, rhodium, ruthenium, and the like, free or supported on a carrier such as, for example, carbon, silica, and the like. Suitable solvents include alkanols, such as methanol, ethanol, 2-propanol, 1-butanol, 2-pentanol and 3-hexanol, and the like. Palladium-on-carbon is preferred. Five percent palladium-on-carbon is most preferred. Ethanol is also preferred. A mineral acid such as hydrochloric acid, sulfuric acid, phosphoric acid or nitric acid may be utilized to promote the conversion. Hydrochloric acid is preferred. The hydrogenation is preferably carried out at an elevated pressure of about 5 atmospheres. The reaction, however, proceeds readily at reduced pressures within the range of about 1 to about 5 atmospheres.

The condensation of (VIIa) with amines $R_5R_6NH$ (XVIII) is accomplished by means of the process described hereinbefore for the conversion of 1,2-dihydrobenzo[b]pyrrolo[3,2,1-jk][1,4]benzodiazepin-6-one XVI to benzodiazepine (Ib).

Alternatively, 1-(2-cyanophenyl)nitroindoline (V) is converted to 7-aminobenzodiazepine (VIIb), which may be hydrolyzed to benzodiazepinone (VIIa) and transformed to benzodiazepine (Ia) by procedures hereinbeforedescribed.

The synthesis of benzo[c]pyrrolo[1,2,3-ef][1,5]benzodiazepines of formula (Id) is also accomplished by methods described hereinbefore. Thus, dehydrogenation of benzodiazepinone (VIIa) with, for example, 2,3-dichloro-5,6-dicyanobenzoquinone in xylene affords the dehydro compound (XXII), which is converted to benzodiazepine (Id) by means of, for example, $R_5R_6NH$ (XVIII) in the presence of a Lewis acid, e.g., titanium tetrachloride. Benzodiazepine (Ia) may be converted to the dehydro compound (Id) by analogous dehydrogenation techniques disclosed hereinbefore.

The quinobenzodiazepines of the present invention may be prepared by the processes described in Reaction Schemes C and D.

To prepare 7-substituted-2,3-dihydro-1H-quino[1,8-ab][1,5]benzodiazepines of the formula (Ie), 1-(aminophenyl)tetrahydroquinoline of formula (XI'), the preparation of which is hereinafterdescribed, may be converted to 1-(ureidophenyl)tetrahydroquinoline (XV'), either directly or via the phenoxycarbonyl derivative (XIV'), which may be cyclized to (Ie) or a mixture of (Ie) and 2,3-dihydroquino[1,8-ab][1,5]benzodiazepin-7-one (XVI'), the latter of which, i.e., compound (XVI'), may be condensed with amines $R_5R_6$ (XVIII) wherein $R_5$ and $R_6$ are as hereinbeforedefined to provide compounds of formula (Ie). See Reaction Scheme C.

The conversion of 1-(aminophenyl)tetrahydroquinoline (XI') to urea (XV') may be accomplished by treating (XI') with a carbonyl halide of the formula $R_4CO$-Hal (XIX) wherein $R_4$ and Hal are as hereinbeforedefined in the presence of a suitable base and a suitable solvent, essentially by the procedure hereinbeforedescribed for the preparation of compound (XII). Included among suitable bases are alkali metal carbonates and bicarbonates, e.g., lithium, sodium and potassium carbonates, and lithium, sodium and potassium bicarbonates. Included among suitable solvents are halocarbons, e.g., dichloromethane, trichloromethane, tetrachloromethane, dichloroethane, and the like. A combination of sodium bicarbonate or potassium carbonate and trichloromethane is preferred. The temperature at which the conversion is effected is not narrowly critical. To promote a reasonable rate of conversion, an elevated temperature, e.g., the reflux temperature of the reaction mixture, may be employed.

Alternatively, 1-(aminophenyl)tetrahydroquinoline (XI') may be treated with a haloformate of the formula $R_{16}OCOHal$ (XX) in the presence of a suitable base, e.g., a tertiary amine such as trimethyl-, triethyl-, tripropylamine, and the like, or a heterocyclic amine such as pyridine, lutidine, collidine, and the like, and a suitable solvent, e.g., a halocarbon such as dichloromethane, trichloromethane and the like, preferably at ambient temperature, to provide carbamate (XIV'), which, in turn, may be treated with $R_5R_6NH$ (XVIII) in a suitable solvent, e.g., an aromatic solvent such as benzene, toluene, xylene, and the like, or a halocarbon such as dichloromethane, trichloromethane, and the like to afford (XV'). While these reactions generally may be conducted at ambient temperature, elevated temperatures such as the reflux temperature of the reaction medium may be employed to establish reasonable rate of reaction.

The cyclization of urea (XV') to 2,3-dihydro-1H-quino[1,8-ab][1,5]benzodiazepine (Ie) may be conveniently performed by contacting urea XV' with a phosphorus oxychloride, phosphorus trichloride or tribromide, or polyphosphoric acid ethyl ester at a temperature within the range of about ambient temperature to the reflux temperature of the reaction mixture. A temperature about the reflux temperature of the reaction mixture may be preferred. The cyclization proceeds readily in the absence of a solvent. A suitable solvent may be employed, however. Among suitable solvents, there may be mentioned aromatic solvents such as, for example, benzene, toluene, xylene, and the like, and halocarbons such as dichloromethane, trichloromethane and the like.

When polyphosphoric acid ethyl ester is utilized as the catalyst in the cyclization step (XV'→Ie), in addition to quinobenzodiazepine (Ie), quinobenzodiazepin-7-one (XVI') may be formed and isolated. For example, treatment of (XV') wherein X is chloro with polyphosphoric acid ethyl ester in a halocarbon solvent such as 1,2-dichloroethane at a reaction temperature of about 75° C. may afford a mixture of the diazepine (Ie) wherein X is chloro and diazepinone (XVI') wherein X is chloro.

Diazepinones (XVI') may also be prepared by hydrolysis of diazepines (Ie). Thus, treatment of (Ie) with an aqueous mineral acid such as hydrochloric acid, sulfuric acid, nitric acid, phosphoric acid, and the like at a reaction temperature between about ambient temperature and the reflux temperature of the reaction medium may furnish lactam (XVI'), which is useful as a precursor for the synthesis of diazepines, i.e., diazepines of formula (Ie) having substituents $R_4$ other than those of the starting material for the hydrolysis (Ie→XVI').

Thus, treatment of diazepinone XVI' with amines of the formula $R_5R_6NH$ (XVIII) wherein $R_5$ and $R_6$ are as hereinbeforedescribed in the presence of a Lewis acid and an aromatic solvent affords diazepines (Ie) wherein $R_4$ is as hereinbeforedescribed. Lewis acids include titanium tetrachloride, aluminum chloride, and the like. Aromatic solvents include benzene, toluene, xylene, mesitylene, and the like. Titanium tetrachloride is the prefered Lewis acid. Toluene is the prefered aromatic solvent. The temperature at which the conversion of (XVI') to (Ie) is performed may not be critical. While the reaction may proceed readily at moderate temperatures, elevated temperatures up to and including the reflux temperature of the reaction system may be employed to promote the reaction. A reaction temperature of about the reflux temperature of the reaction medium may be preferred.

1-(Aminophenyl)tetrahydroquinoline (XI') may be synthesized by condensing tetrahydroquinoline (XIII') with halonitrobenzene (IX) by the procedure hereinbeforedescribed for the preparation of the corresponding indoline of formula (X) and reducing the nitro group of (X') to the amino function of (XI'), by the method hereinbeforedescribed for the preparation of the corresponding compound in the indoline series.

To gain entry into the quino[1,8-ab][1,4]benzodiazepine series (If), the cyano group of a 1-(2-cyanophenyl)-tetrahydroquinoline of formula (V'), the preparation of which is hereinafter described, may be hydrolyzed to a 1-(2-carboxyphenyl)tetrahydroquinoline of formula (XXI'), which may be converted to the quino[1,8-ab][1,4]benzodiazepin-8-one (XXII') and then condensed with an amine of the formula $R_5R_6NH$ (XVIII) to furnish benzodiazepines of formula (If).

The hydrolysis may be conveniently carried out by treating the nitrile of formula (V') with an alkali metal or alkaline earth hydroxide such as, for example, lithium, sodium, or potassium hydroxide, or calcium or magnesium hydroxide, in an alkanol such as, for example, methanol, ethanol, 2-propanol, 1-butanol, 2-pentanol, 3-hexanol, and the like, or a glycol such as, for example, ethylene glycol, propylene glycol, and the like. Potassium hydroxide and ethylene glycol are prefered. The hydrolysis proceeds at a convenient rate at the reflux temperature of the reaction medium. Reduced temperatures may be used to effect the transformation of nitrile (V') to carboxylic acid (XXI').

The conversion of the 1-(2-carboxyphenyl)tetrahydroquinoline (XXI') to the benzodiazepinone (XXII') may be performed by reducing the nitro group with hydrogen in the presence of a metal catalyst in a suitable solvent. Among metal catalysts, there may be mentioned platinum, palladium, rhodium, ruthenium, and the ike, free or supported on a carrier such as, for example, carbon, silica, and the like. Suitable solvents include alkanols, such as methanol, ethanol, 2-propanol, 1-butanol, 2-pentanol and 3-hexanol, and the like. Palladium-on-carbon may be preferred. Five percent palladium-on-carbon may be most preferred. Ethanol may also be preferred. A mineral acid such as hydrochloric acid, sulfuric acid, phosphoric acid or nitric acid may be utilized to promote the conversion. Hydrochloric acid may be preferred. The hydrogenation may preferably be carried out at an elevated pressure of about 5 atmospheres. The reaction, however may proceed readily at reduced pressures within the range of about 1 to about 5 atmospheres.

The condensation of (XXII') with amines $R_5R_6NH$ (XVIII) may be accomplished by means of the process described hereinbefore for the conversion of benzo[b-]pyrrolo[3,2,1-jk][1,4]benzodiazepin-6-one (XVI) to benzodiazepine (Ib).

Alternatively, 1-(2-cyanophenyl)-nitrotetrahydroquinoline (V') may be converted to 8-aminobenzodiazepine (XIII'), which may be hydrolyzed to benzodiazepinone (XXII') and transformed to benzodiazepine (If) by procedures hereinbeforedescribed.

1-(2-Cyanophenyl)tetrahydroquinoline (V') may be prepared by procedures similar to those hereinbeforedescribed for the synthesis of related compounds in the indoline series involving, for example, the condensation of a tetrahydroquinoline (II') with a halobenzonitrile (III) followed by nitration of the 1-(cyanophenyl)tetrahydroquinoline IV'. See Reaction Scheme E.

The preparation of a 5-bromodihydroindole (XXIV) or a 6-bromotetrahydroquinoline (XXIV') wherein Y may be halogen, $CF_3$, lower alkyl or lower alkylsulfonyl; q is 1 or 2; and $R_{17}$ is nitro or a group of the formula

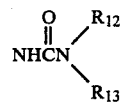

wherein $R_{12}$ and $R_{13}$ are lower alkyl; and $R_{12}$ and $R_{13}$ taken together with the nitrogen atom to which they are attached form a group of the formula

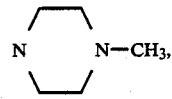

i.e., a compound of formula X, X', XV or XV' wherein one of the X-substituents is bromine bound to the 5-position of the hydroindole ring or the 6-position of the tetrahydroquinoline ring, is accomplished by treating a dihydroindole (XXIII), or a tetrahydroquinoline (XXIII') with a brominating agent such as N-bromoacetamide or N-bromosuccinimide in a dipolar aprotic solvent. Among dipolar aprotic solvents there may be mentioned dimethylacetamide, dimethylformamide, hexamethylphosphoramide and the like. N-bromosuccinimide is the preferred brominating agent. Dimethylformamide is the preferred solvent. The temperature at which the bromination is preformed is not narrowly critical. It is preferred, however, to carry out the bromination at a reaction temperature between about $-25°$ to about $100°$ C., a reaction temperature within the range of about $-10°$ C. to $60°$ C. being most preferred. See Reaction Scheme F.

The benzopyrrolobenzodiazepines and quinobenzodiazepines of the present invention are useful for treating psychoses by virtue of their ability to elicit an antipsychotic response in mammals.

Antipsychotic activity is determined in the climbing mice assay by a method similar to those described by P. Protais, et al., Psychopharmacol., 50, 1 (1976) and B. Costall, Eur. J. Pharmacol., 50, 39 (1978).

The subject CK-1 male mice (23–27 grams) are group-housed under standard laboratory conditions. The mice are individually placed in wire mesh stick cages (4"×4"×10") and are allowed one hour for adaptation and exploration of the new environment. Then apomorphine is injected subcutaneously at 1.5 mg/kg, a dose causing climbing in all subjects for 30 minutes.

Compounds to be tested for antipsychotic activity are injected intraperitoneally or given oral doses at various time intervals, e.g. 30 minutes, 60 minutes, etc. prior to the apomorphine challenge at a screening dose of 10–60 mg/kg.

For evaluation of climbing, 3 readings are taken at 10, 20 and 30 minutes after apomorphine administration according to the following scale:

| Climbing Behavior | Score |
|---|---|
| Mice with: | |
| 4 paws on bottom (no climbing) | 0 |
| 2 paws on the wall (rearing) | 1 |
| 4 paws on the wall (full climb) | 2 |

Mice consistently climbing before the injection of apomorphine will be discarded.

With full-developed apomorphine climbing, the animals are hanging on to the cage walls, rather motionless, over longer periods of time. By contrast, climbs due to mere motor stimulation usually only last a few seconds.

The climbing scores are individually totaled (maximal score: 6 per mouse over 3 readings) and the total score of the control group (vehicle intraperitoneally—apomorphine subcutaneously) is set to 100%. $ED_{50}$ values with 95% confidence limits, calculated by a Linear Regression Analysis, of some of the instant benzopyrrolobenzodiazepines as well as a standard antipsychotic agent are presented in Table 1.

TABLE 1

| COMPOUND | CLIMBING MOUSE ASSAY ($ED_{50}$ mg/kg, po) |
|---|---|
| 9-Bromo-6-(4-methyl-1-piperazinyl)-1,2-dihydrobenzo[b]pyrrolo[3,2,1-jk]-[1,4]benzodiazepine | 30.8 |
| 9-Methyl-6-(4-methyl-1-piperazinyl)-1,2-dihydrobenzo[b]pyrrolo[3,2,1-jk]-[1,4]benzodiazepine | 25.5 |
| 9-bromo-6-(4-methyl-1-piperazinyl)-benzo[b]pyrrolo[3,2,1-jk][1,4]benzodiazepine | 13.5 |
| 4-chloro-6-(4-methyl-1-piperazinyl)-benzo[b]pyrrolo[3,2,1-jk][1,4]-benzodiazepine | 13.4 |
| clozapine | 23.2 |

Antipsychotic response is achieved when the present benzopyrrolobenzodiazepines and quinobenzodiazepines are administered to a subject requiring such treatment as an effective oral, parenteral or intravenous dose of from 0.01 to 50 mg/kg of body weight per day. A particularly preferred effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

Some of the benzopyrrolobenzodiazepines and quinobenzodiazepines of the present invention are also useful as analgetics due to their ability to alleviate pain in mammals. The analgetic utility is demonstrated in the phenyl-p-quinone writhing assay in mice, a standard assay for analgesia [Proc. Soc. Exptl. Biol Med., 95 729 (1957)]. Thus, for instance, the subcutaneous dose effecting an approximately 50% inhibition of writhing ($ED_{50}$) in mice produced in this assay is as shown in Table 2.

TABLE 2

| COMPOUND | INHIBITION OF PHENYLQUINONE INDUCED WRITHING $ED_{50}$ mg/kg, sc |
|---|---|
| 9-chloro-6-(4-methyl-1-piperazinyl)-1,2-dihydrobenzo[b]pyrrolo[3,2,1-jk]-[1,4]benzodiazepine | 4.1 |
| 9-methyl-6-(4-methyl-1-piperazinyl)-1,2-dihydrobenzo[b]pyrrolo[3,2,1-jk]-[1,4]benzodiazepine | 0.34 |
| 9-bromo-6-[(2-dimethylamino)-N—methylethylamino]-1,2-dihydrobenzo-[b]pyrrolo[3,2,1-jk][1,4]-benzodiazepine | 8.1 |
| 9-bromo-6-(4-methyl-1-piperazinyl)-benzo[b]pyrrolo[3,2,1-jk][1,4]-benzodiazepine | 0.72 |
| propoxyphene (standard) | 3.9 |

Analgesia production is achieved when the present benzopyrrolobenzodiazepines and quinobenzodiazepines are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Compounds of the invention also include:
4-chloro-6-(4-methyl-1-piperazinyl)-1,2-dihydrobenzo[b]pyrrolo[3,2,1-jk][1,4]benzodiazepine;
4-bromo-6-(4-methyl-1-piperazinyl)-1,2-dihydrobenzo[b]pyrrolo[3,2,1-jk][1,4]benzodiazepine;
4-methyl-6-(4-methyl-1-piperazinyl)-1,2-dihydrobenzo[b]pyrrolo[3,2,1-jk][1,4]benzodiazepine;
9-bromo-4-chloro-6-(4-methyl-1-piperazinyl)-1,2-dihydrobenzo[b]pyrrolo[3,2,1-jk][1,4]benzodiazepine;
4-chloro-9-methyl-6-(4-methyl-1-piperazinyl)-1,2-dihydrobenzo[b]pyrrolo[3,2,1-jk][1,4]benzodiazepine;
10-methyl-6-(4-methyl-1-piperazinyl)-1,2-dihydrobenzo[b]pyrrolo[3,2,1-jk][1,4]benzodiazepine;
9-chloro-7-(4-methyl-1-piperazinyl)-1,2-dihydrobenzo[c]pyrrolo[1,2,3-ef][1,5]benzodiazepine;
9-chloro-4-methyl-7-(4-methyl-1-piperazinyl)-1,2-dihydrobenzo[c]pyrrolo[1,2,3-ef][1,5]benzodiazepine;
4-bromo-9-chloro-7-(4-methyl-1-piperazinyl)-1,2-dihydrobenzo[c]pyrrolo[1,2,3-ef][1,5]benzodiazepine;
10-bromo-7-(4-methyl-1-piperazinyl)-2,3-dihydro-1H-quino[1,8-ab][1,5]benzodiazepine;
10-bromo-5-methyl-7-(4-methyl-1-piperazinyl)-2,3-dihydro-1H-quino[1,8-ab][1,5]benzodiazepine;
10-methyl-8-(4-methyl-1-piperazinyl)-2,3-dihydro-1H-quino[1,8-ab][1,4]benzodiazepine;
10-bromo-5-methyl-8-(4-methyl-1-piperazinyl)-2,3-dihydro-1H-quino[1,8-ab][1,4]benzodiazepine.

Effective amounts of the compounds of the present invention may be administered to a subject by any one of the several methods, for example, orally as in capsules or tablets, parenterally in the form of sterile solutions or suspensions, and in some cases intravenously in the form of sterile solutions. The benzopyrrolobenzodiazepines and quinobenzodiazepines of the present invention, while effective themselves, may be formulated and administered in the form of their pharmaceutically acceptable acid addition salts for purposes of stability, convenience or crystallization, increased solubility and the like.

Preferred pharmaceutically acceptable acid addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

Effective quantities of the compounds of the invention may be administered orally, for example, with an inert diluent or with an edible carrier. They may be enclosed in gelatin capsules or compressed into tablets. For the purposes of oral therapeutic administration, the aforesaid compounds may be incorporated with an excipient and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0-300 milligrams of the active compound.

The tablets, pills, capsules, troches and the like may also contain the following ingredients: a binder such as microcrystalline cellulose, gum tragancanth or gelatine; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains beteen 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens, antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

REACTION SCHEME A
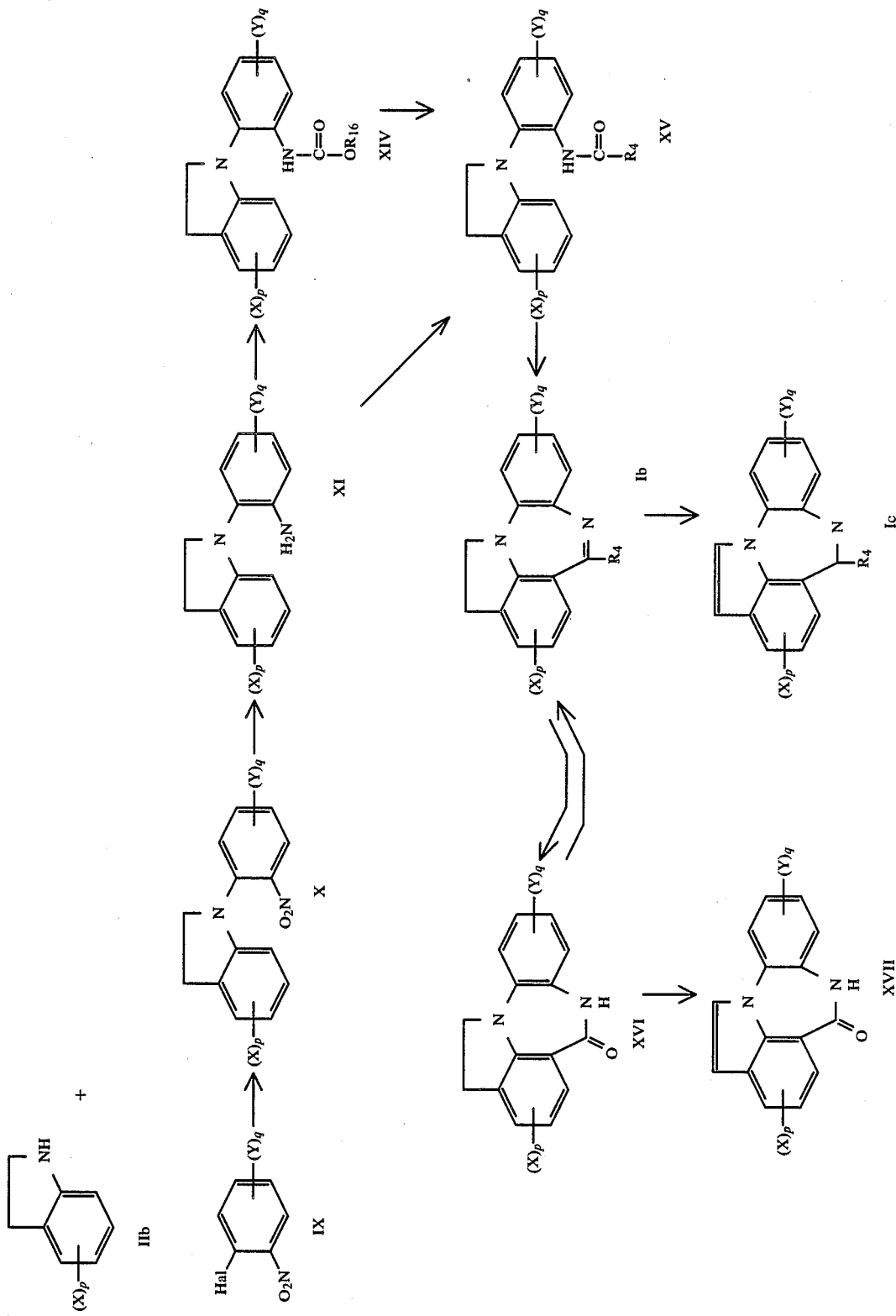
wherein X, Y, R4, p, q and Hal are as hereinbeforedescribed.

REACTION SCHEME B
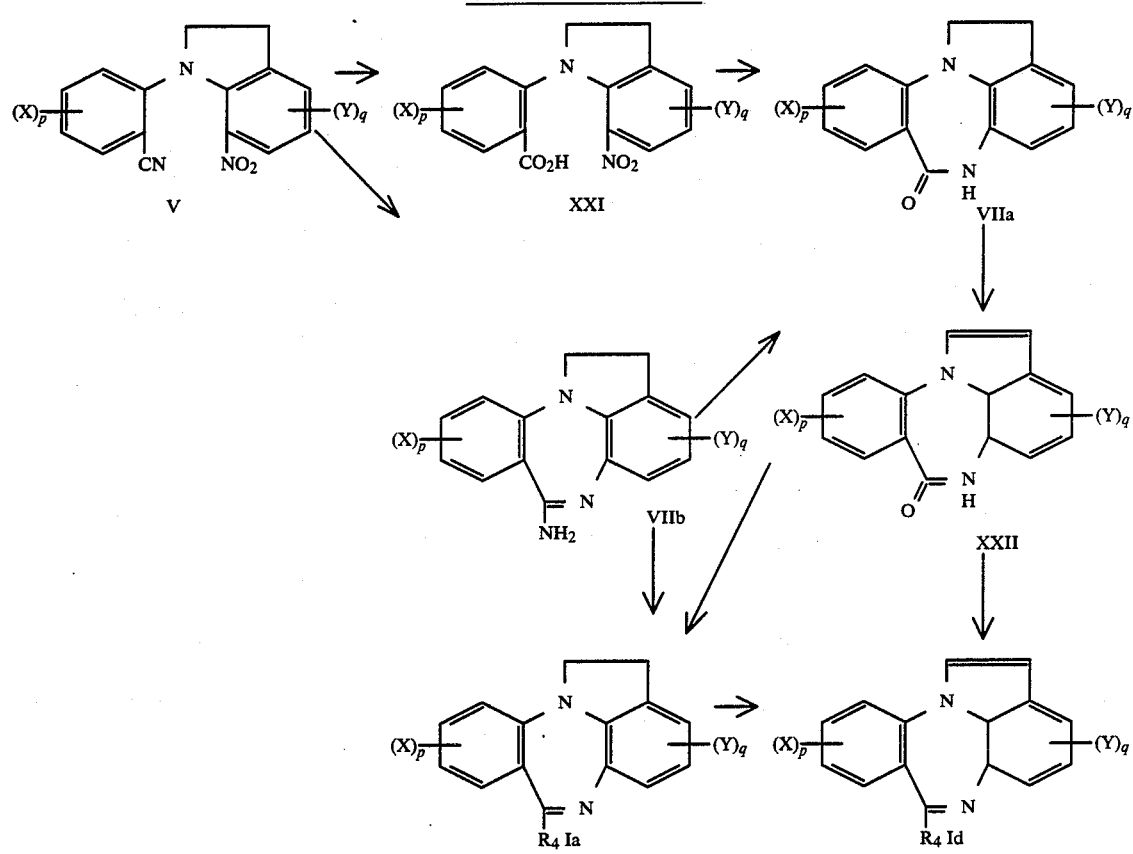
wherein X, Y, R₄, p and q are as hereinbeforedescribed.

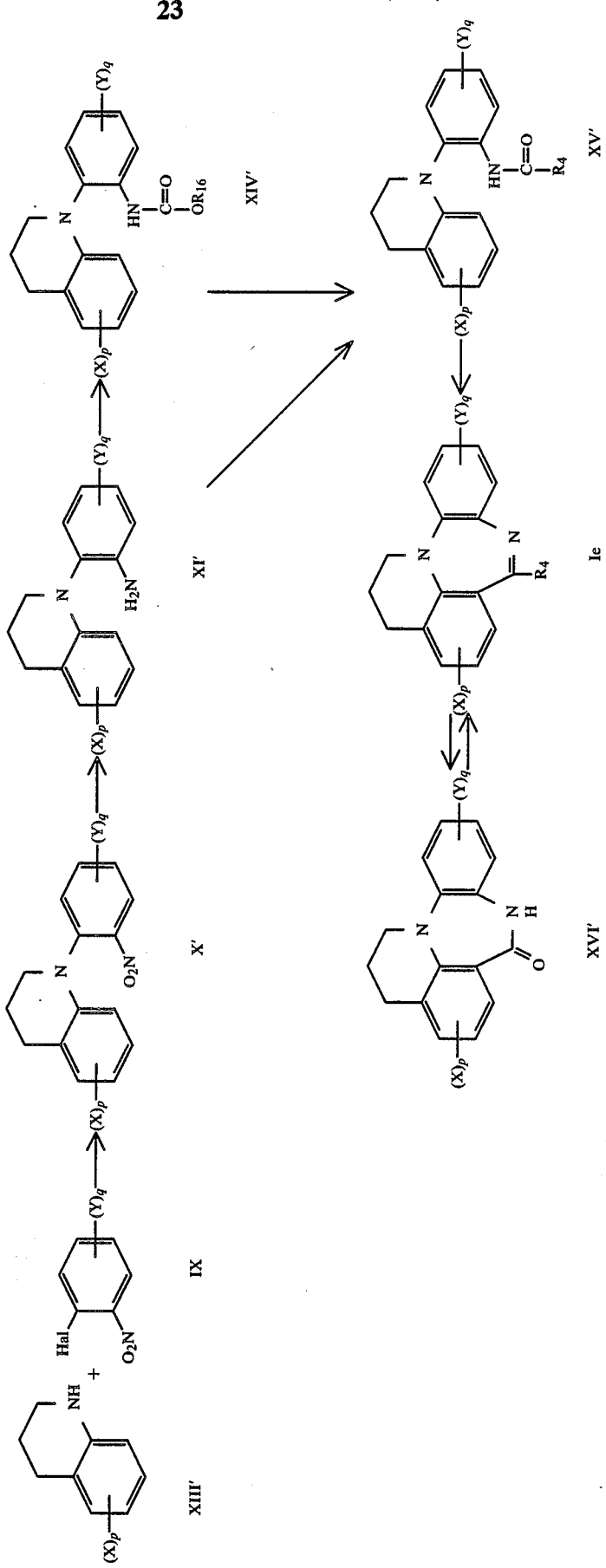
REACTION SCHEME C
wherein X, Y, R4, p, q and Hal are as hereinbefore described.

REACTION SCHEME D
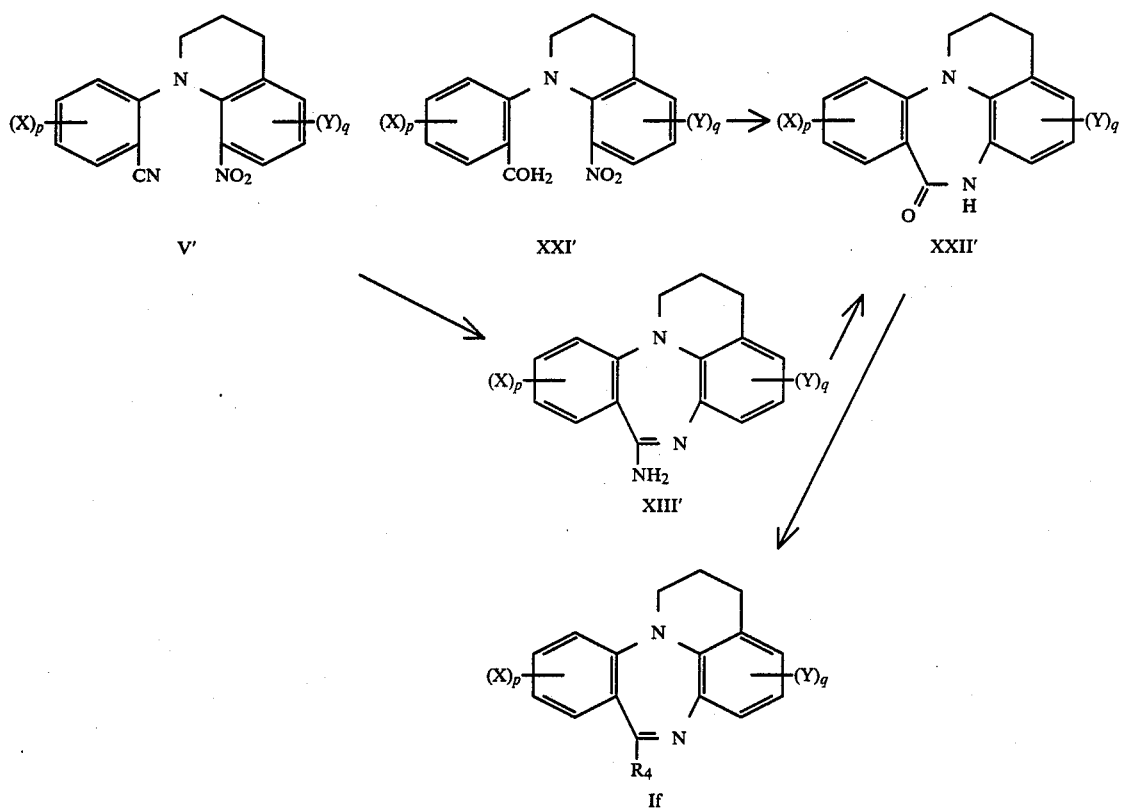
wherein X, Y, p, q and R₄ are as hereinbefore described.
REACTION SCHEME E
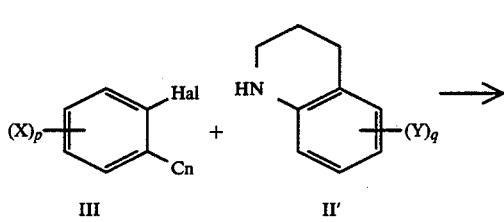
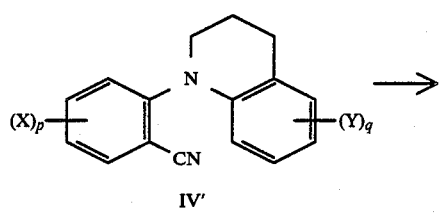
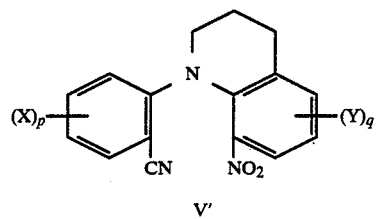
wherein X, Y, p and q are as hereinbeforedescribed.
REACTION SCHEME F
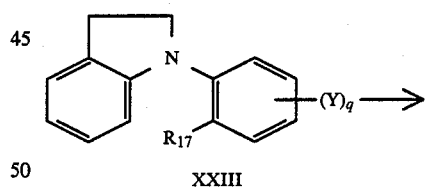
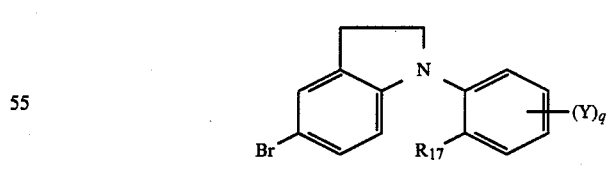
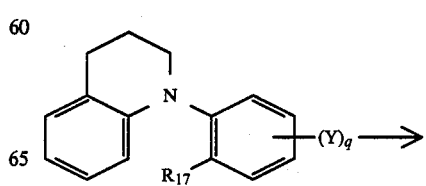

-continued
REACTION SCHEME F

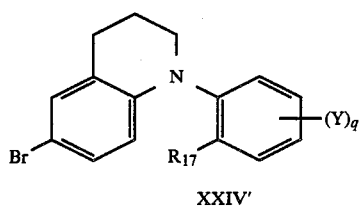

XXIV' where Y is as hereinbeforedescribed.

The following examples are for illustrative purposes only and are not to be construed as limiting the invention. All temperatures are given in degrees Centrigrade (°C.) unless indicated otherwise.

EXAMPLE 1 a.

2-(5-Chloro-indolin-1-yl)benzamide

A slurry was prepared comprising 5-chloroindoline (15.3 gm, 0.1 mole), dimethylsulfoxide (DMSO) [50 ml] and sodium hydride (5.28 gm, 50% in oil, washed with hexane). The slurry was permitted to stir at room temperature for 1 hour. To this a solution of o-fluorobenzamide (15.2 gm, 1.1 eq.) in DMSO (20 ml) was added dropwise with the temperature between 17°-19° C. At the end of addition the reaction mixture was stirred at room temperature for 2 hours, then heated to 75°-78° C. for 16 hours. The reaction mixture was partitioned between methylene chloride (300 ml) and water (250 ml). The aqueous phase was separated and extracted twice with methylene chloride (150 ml). The combined organic solution was washed twice with water, twice with HCl (2N, 100 ml), brine (2×50 ml), dried over $Na_2SO_4$, concentrated to about 50 ml. Ether (50 ml) was added. The product was crystallized out upon standing overnight (about 16 hours). The yield was 14.2 gm (52%); m.p. 137°-138° C. Recrystallization from methylene chloride and ether yielded 2-(5-chloro-indolin-1-yl)benzamide (11.82 gm) m.p. 137°-138° C.

ANALYSIS: Calculated for $C_{15}H_{13}ClN_2O$: 66.06%C 5.01%H 10.29%N. Found: 65.69%C 4.92%H 10.18%N.

b.

2-(5-Chloro-7-nitroindolin-1-yl)benzamide

A solution of 2-(5-chloroindolin-1-yl)benzamide of Example 1a (11.9 gm), silver nitrate (8.16 gm, 1.1 equivalents), chloroform (50 ml) and acetonitrile (100 ml) was chilled to 15° C. To this a solution of acetyl chloride (3.8 gm, 1.1 equivalents) in acetonitrile (10 ml) was added dropwise in 20 minutes. The mixture was stirred at room temperature for 3 hours. The mixture was diluted with methylene chloride (250 ml) and filtered. The ppt (AgCl) was washed with a large volume of methylene chloride (1.2 l in several portions). The combined organic solution was washed twice with brine (125 ml) containing $NaHCO_3$ (2.5 gm), dried over $Na_2SO_4$, and evaporated down to a solid (14.9 gm). Recrystallization from chloroform:ether (1:1) afforded crystals of 2-(5-chloro-7-nitroindolin-1-yl)benzamide, 12.6 gm (76%), m.p. 225°-226° C.

ANALYSIS: Calculated for $C_{15}H_{12}ClN_3O_3 \cdot \frac{1}{2}CHCl_3$: 49.33%C 3.34%H 11.13%N. Found: 49.67%C 3.39%H 11.24%N.

c.

2-(5-Chloro-7-aminoindolin-1-yl)benzamide

To the solution of 2-(5-chloro-7-nitroindolin-1-yl)benzamide of Example 1b (10 gm, 26.5 mmoles) in dimethylformamide (DMF) [100 ml] and ethanol (100 ml) was added 1% Pt/carbon (2.0 gm). The mixture was shaken under hydrogen (59 psi) for 4½ hours. The mixture was then filtered under nitrogen and concentrated to remove solvent at 55° C. and high vacuum to give a solid (9.1 gm). Recrystallization from chloroform twice afforded 2-(5-chloro-7-aminoindolin-1-yl)benzamide, (4.3 gm, 47.3%), m.p. 199°-201° C. dec.

ANALYSIS: Calculated for $C_{15}H_{14}ClN_3O \cdot \frac{1}{2}H_2O$: 60.71%C 5.06%H 14.16%N. Found: 60.51%C 4.68%H 14.32%N.

d.

4-Chloro-1,2-dihydrobenzo[c]pyrrolo[1,2,3-ef][1,5]benzodiazepin-7-one 2-(5-chloro-7-aminoindolin-1-yl)benzamide of Example 1c (28.7 g, 0.10 mole) was dissolved in methanol/dichloromethane (DCM) solution (1:9 v/v) at 35° C. Silica gel (510 gm) was added to absorb the starting material, then the solvent was removed as much as possible under vacuum (50° C., 25 mmHg pressure for 1 hr.) The reaction mixture was then heated at 145°-155° C. and mechanically stirred for 1½ hours. The heating was stopped when the mixture started to turn brown. The combined material was placed onto a flash chromatography column (1 kg, silica gel 60, slurry packed with DCM), eluted with DCM (16 l) and 2% $CH_3OH$ in DCM (10 l). The fractions containing the desired product were pooled and concentrated to yield a solid, 16 gm, (59%), m.p. 252°-255° C.

ANALYSIS: Calculated for $C_{15}H_{11}ClN_2O$: 66.55%C 4.10%H 10.35%N. Found: 66.85%C 4.14%H 10.38%N.

e.

4-chloro-1,2-dihydrobenzo[c]pyrrolo[1,2,3-ef][1,5]benzodiazepin-7-one

Alternatively 4-chloro-1,2-dihydrobenzo[c]pyrrolo[1,2,3-ef][1,5]benzodiazepin-7-one can be prepared in the following manner. 2-(5-chloro-7-aminoindolin-1-yl)benzamide (2.17 gm, 7.5 mmoles) in 100 ml of hot ethanol was treated with 5 ml of ethereal-HCl solution. The red crystals formed in approximately 5 minutes. It was chilled in freezer overnight (16 hours), filtered to give 1.80 gm (89%) of pure compound with the same melting point as Example 1d.

f.

4-Chloro-7-(4-methyl-1-piperazinyl)-1,2-dihydrobenzo[c]pyrrolo[1,2,3-ef][1,5]benzodiazepine A mixture comprising toluene (250 ml), N-methyl piperazine (15 ml, 13.5 gm, 10 equivalents) and titanium tetrachloride (3 ml) was stirred for 20 minutes and then 4-chloro-1,2-dihydrobenzo[c]pyrrolo[1,2,3-ef][1,5]benzodiazepine-7-one (3.5 gm, 12.9 mmoles) was added in one portion. The resultant mixture was refluxed at 100° C. for 20 minutes, then cooled down slowly over 2 hours. The mixture was diluted with ether (500 ml) and filtered. The residue was brought into water (600 ml) and was extracted twice with ether (400 ml). The combined ether solution was washed twice with brine (150 ml) and dried over $Na_2SO_4$. Evaporation to dryness gave a solid (4.3 gm). Purification of the crude product was effected by flash chromatography over silica gel (200 gm, packed and eluted with 4% $CH_3OH$ in DCM, 1.5 l). The fractions (15 ml each) containing the pure product were pooled and concentrated to give 2.6 g (57%) of a solid. Recrystallization from ethanol yielded 2.05 gm of 4-chloro-7-(4-methyl-1-piperazinyl)-1,2-dihydrobenzo[c]pyrrolo[1,2,3-ef][1,5]benzodiazepine, m.p. 199°–200.5° C.

ANALYSIS: Calculated for $C_{20}H_{21}ClN_4$: 68.08%C 6.00%H 15.88%N. Found: 68.37%C 6.08%H 15.97%N.

EXAMPLE 2 a.

1-(4-Fluoro-2-nitrophenyl)indoline

A stirred solution of 14.9 g (0.125 mole) of indoline, 15.9 g (0.10 mole) of 2,5-difluoronitrobenzene, and 15.2 g (0.125 mole) of collidine in 100 ml of xylene was refluxed overnight (about 16 hours). After cooling to room temperature, 250 ml of dichloromethane and 250 ml of water were added with vigorous stirring. The organic phase was separated, washed twice with water, twice with 2N-HCl, once with 2N-NaOH, once more with brine, then dried and concentrated in vacuo to 19.2 g (74%) of an oil. This material was dissolved in 60 ml of iso-propyl ether from which 11.5 g (45% yield) of product crystallized. This material was recrystallized from methanol to afford 8.5 g (33% overall yield) of 1-(4-fluoro-2-nitrophenyl)indoline, m.p. 87°–89° C.

ANALYSIS: Calculated for $C_{14}H_{11}FN_2O_2$: 65.11%C 4.29%H 10.85%N. Found: 65.07%C 4.41%H 10.90%N.

b.

1-(2-Amino-4-fluorophenyl)indoline Hydrochloride

A Parr bottle, charged with 12.9 g (0.05 mole) of 1-(4-fluoro-2-nitrophenyl)indoline of Example 2a, 200 ml absolute ethanol, 0.3 g of 5% of Pd/C, was shaken under 59 psi pressure of hydrogen until uptake ceased. The catalyst was then removed by filtration and the filtrate was concentrated to an oil weighing 11.6 g (100%). This was dissolved in 75 ml of ethanol, with heating, and then 25 ml of ether saturated with hydrogen chloride was added. An additional 400 ml of plain ether was added to maximize precipitation. The hydrochloride salt was collected, dried, and found to weigh 9.1 g (69%). Recrystallization from ethanol-ether afforded 6.8 g (52% overall yield) of 1-(2-amino-4-fluorophenyl)indoline hydrochloride, m.p. 190°–193° C.

ANALYSIS: Calculated for $C_{14}H_{13}FN_2.HCl$: 63.52%C 5.33%H 10.58%N. Found: 63.63%C 5.35%H 10.64%N.

c.

N-[2-(2,3-Dihydro-1H-indol-1-yl)-5-fluorophenyl]-4-methyl-1-piperazine carboxamide Maleate To a stirred solution under nitrogen, of 50.2 g (0.22 mole) of 1-(3-amino-4-fluorophenyl)indoline of Example 2b, and 66.7 g (0.66 mole) of triethylamine in 900 ml of chloroform was added 65.7 g (0.33 mole) of 4-methyl-1-piperazine carbonyl chloride hydrochloride in portions over 5 minutes. The reaction was refluxed for 6 hours when an additional 22.2 g (0.22 mole) of triethylamine and 43.8 g (0.22 mole) of the carbonyl chloride reagent were added. After refluxing overnight (about 16 hours) the reaction was cooled, treated with 1 liter of water and stirred vigorously for 15 minutes. The layers were separated, and the organic phase was washed twice with water, dried over $Na_2SO_4$, and concentrated in vacuo to leave 50 g. This material was dissolved in 150 ml of toluene and absorbed on a tall chromatography column containing 1.5 kg of silica gel made up in toluene. Elution first with toluene, then with increasing percentages (25% per step) of dichloromethane ($CH_2Cl_2$) in toluene, followed by 100% $CH_2Cl_2$, and finally by increasing percentages of methanol (1% per step) in $CH_2Cl_2$ brought forth 27.3 g (35% overall yield) of pure urea. 12.7 g (0.036 mole) was converted to the maleate salt in the following manner. The urea was dissolved in 30 ml of ethanol and treated with a solution of 4.64 g (0.04 mole) of maleic acid in 20 ml of warm ethanol. The salt crystals were collected, and found to weigh 13.2 g (78%). Two recrystallizations from ethanol furnished N-[2-(2,3-dihydro-1H-indol-1-yl)-5-fluorophenyl]-4-methyl-1-piperazine carboxamide maleate, m.p. 117°–120° C.

ANALYSIS: Calculated for $C_{20}H_{23}FN_4O.C_4H_4O_4$: 61.27%C 5.78%H 11.91%N. Found: 61.18%C 5.94%H 11.80%N.

d.

9-Fluoro-6-(4-methyl-1-piperazinyl)-1,2-dihydrobenzo[b]pyrrolo[3,2,1-jk][1,4]benzodiazepine A stirred mixture of 10.6 g (0.030 mole) of N-[2-(2,3-dihydro-1H-indol-1-yl)-5-fluorophenyl]-4-methyl-1-piperazine carboxamide of Example 2c in 250 ml of phosphorus oxychloride was refluxed for 6 hours under nitrogen, then cooled to room temperature. The excess phosphorus oxychloride was removed at aspirator pressure with gentle warming. The residue was chilled in an ice-bath (with exclusion of moisture) and then treated first with 250 ml of ice-cold 2N-NaOH, then with 500 ml of dichloromethane. The mixture was stirred vigorously until all the material passed into solution. The organic phase was separated, washed thrice with water, dried over $Na_2SO_4$ and concentrated in vacuo to 9.1 g of an oil. This material was adsorbed on a tall chromatography column containing 400 g of alumina made up in $CH_2Cl_2$. Elution with $CH_2Cl_2$ brought forth fractions of pure tetracycle which were combined and concentrated to afford 3.5 g (35% overall yield) of product which crystallized. This was recrystallized from a small volume of acetone to furnish 2.1 g of 9-fluoro-6-(4-methyl-1-piperazinyl)-1,2-dihydrobenzo[b]pyrrolo[3,2,1-jk][1,4]benzodiazepine, m.p. 151°–153° C.

ANALYSIS: Calculated for $C_{20}H_{21}FN_4$: 71.41%C 6.29%H 16.65%N. Found: 71.07%C 6.35%H 16.46%N.

EXAMPLE 3 a.

1-(4-Bromo-2-nitrophenyl)indoline

A stirred solution of 29.8 g (0.25 mole) of indoline, 56.2 (0.20 mole) of 2,5-dibromonitrobenzene, and 30.3 g (0.25 mole) of collidine in 200 ml of xylene was refluxed under nitrogen overnight (about 16 hours). After cooling to room temperature, the precipitated salt was removed by filtration, and the filtrate was concentrated. The latter residue was partitioned between 300 ml of dichloromethane and 300 ml of water. The organic phase was separated, washed twice more with water, twice with dilute HCl, once with dilute NaOH, twice more with water, then dried over $Na_2SO_4$ and concentrated in vacuo leaving 55.1 g (92%). This was dissolved in 100 ml of methanol with heating from which 34.7 g (58% yield) of product crystallized. 5 g of this material was recrystallized from ethyl acetate to afford 3.5 g (70%) of 1-(4-bromo-2-nitrophenyl)indoline, m.p. 100°–102° C.

ANALYSIS: Calculated for $C_{14}H_{11}BrN_2O_2$: 52.59%C 3.47%H 8.78%N. Found: 52.86%C 3.55%H 8.81%N.

b.

1-(2-Amino-4-bromophenyl)indoline Hydrochloride

A Parr bottle, charged with 15.96 g (0.050 mole) of 1-(4-bromo-2-nitrophenyl)indoline of Example 3a, 100 ml of benzene, 100 ml of absolute ethanol, and 1.0 g of 1% Pt/carbon, was shaken under an initial 59 psi pressure of hydrogen until uptake ceased. The catalyst was then removed by filtration and the filtrate was concentrated in vacuo to an oil weighing 14.4 (100%). This was dissolved in 25 ml of ethanol, with heating, and then 25 ml of ether saturated with hydrogen chloride was added. An additional 500 ml of plain ether was added to maximize precipitation. The hydrochloride salt was collected, dried, and found to weigh 10.6 g (65%). Recrystallization twice (charcoal) from ethanol-ether afforded 4.8 g (30% overall yield) of 1-(2-amino-4-bromophenyl)indoline hydrochloride, m.p. 185°–188° C.

ANALYSIS: Calculated for $C_{14}H_{13}BrN_2 \cdot HCl$: 51.64%C 4.33%H 8.60%N. Found: 51.63%C 4.42%H 8.66%N.

c.

N-[5-Bromo-2-(2,3-dihydro-1H-indol-1-yl)phenyl]-4-methyl-1-piperazinecarboxamide Maleate To a stirred solution, under nitrogen of 43.5 g (0.15 mole) of 1-(4-bromo-2-aminophenyl)indoline of Example 3b and 82.8 g (0.60 mole) of milled potassium carbonate in 1000 ml of chloroform was added 44.7 g (0.225 mole) of 4-methyl-1-piperazinecarbonyl chloride hydrochloride in portions over 10 minutes. The reaction was refluxed for 6 hours when an additional charge of 10.4 g (0.075 mole) of potassium carbonate and 14.9 g (0.075 mole) of the carbonyl chloride reagent was added. After refluxing overnight (about 16 hours), the reaction was cooled, treated with 500 ml of water, and stirred vigorously for 15 minutes. The layers were separated and the organic phase was washed thrice with water, dried over $Na_2SO_4$, and concentrated in vacuo. The residue was dissolved in 200 ml of toluene and adsorbed on a tall chromatography column containing 1.5 kg of silica gel packed in toluene. Elution first with toluene, then with increasing percentages of dichloromethane in toluene, (25% per step), followed by dichloromethane alone, and finally with 1% methanol in dichloromethane brought forth 24 g (overall 39% yield) of fairly pure urea. This was dissolved in 100 ml of ethanol and treated with a solution of 6.96 g (0.06 mole) of maleic acid dissolved in 50 ml of ethanol. The maleate salt was collected, dried, and found to weigh 17.3 g (22% overall), m.p. 175°–177° C. dec. Recrystallization from methanol (charcoal) afforded 12.7 g (16% overall yield) of N-[5-bromo-2-(2,3-dihydro-1H-indol-1-yl)phenyl]-4-methyl-1-piperazinecarboxamide maleate, m.p. 175°–177° C. dec.

ANALYSIS: Calculated for $C_{20}H_{23}BrN_4O \cdot C_4H_4O_4$: 54.25%C 5.12%H 10.54%N. Found: 54.38%C 5.04%H 10.49%N.

d.

9-Bromo-6-(4-methyl-1-piperazinyl)-1,2-dihydrobenzo[b]pyrrolo[3,2,1-jk][1,4]benzodiazepine A stirred mixture of 9.14 g (0.022 mole) of N-[5-bromo-2-(2,3-dihydro-1H-indol-1-yl)phenyl]-4-methyl-1-piperazinecarboxamide of Example 3c in 250 ml of phosphorus oxychloride was refluxed for 7 hours under nitrogen then cooled to room temperature. The excess phosphorus oxychloride was removed at aspirator pressure with gentle warming. The residue was chilled in an ice-bath (with exclusion of moisture) and then treated first with 250 ml of ice-cold 2N-NaOH, then with 500 ml of dichloromethane. The mixture was stirred vigorously until all the material passed into solution. The organic phase was separated, washed thrice with water, dried over $Na_2SO_4$ and concentrated in vacuo to 8.5 g (98%) of an oil. This material was adsorbed on a tall chromatography column containing 350 g of alumina made up in $CH_2Cl_2$. Elution with $CH_2Cl_2$ brought forth fractions of virtually pure tetracycle which were combined and concentrated to afford 4.6 g (53% overall yield) of product as a foam. This was crystallized from a small volume of methanol to furnish 2.6 g of 9-bromo-6-(4-methyl-1-piperazinyl)-1,2-dihydrobenzo[b]pyrrolo[3,2,1-jk][1,4]benzodiazepine, m.p. 153°–155° C.

ANALYSIS: Calculated for $C_{20}H_{21}BrN_4$: 60.46%C 5.33%H 14.10%N. Found: 60.13%C 5.30%H 14.06%N.

EXAMPLE 4 a.

1-(4-Chloro-2-nitrophenyl)indoline

A stirred solution of 38.4 g (0.20 mole) of 1,4-dichloro-2-nitrobenzene and 59.6 g (0.50 mole) of indoline in 400 ml of dimethylformamide (DMF) was heated under nitrogen at 140°–145° C. overnight (23 hours). The DMF solvent was then removed in vacuo and the residue was dissolved in 500 ml of dichloromethane. This solution was extracted with $H_2O$, with dilute hydrochloric acid, with brine, then dried over $Na_2SO_4$ and concentrated to an oil. This was adsorbed on a tall chromatography column containing 1.5 kg of silica gel packed in toluene. Elution with toluene brought forth 22.1 g (40% overall yield) of product, which crystallized. A small portion was recrystallized from hexane to afford 1-(4-chloro-2-nitrophenyl)indoline, m.p. 97°–99° C.

ANALYSIS: Calculated for $C_{14}H_{11}ClN_2O_2$: 61.21%C 4.04%H 10.20%N. Found: 60.84%C 4.01%H 10.22%N.

b.

N-[5-Chloro-2-(2,3-dihydro-1H-indol-1-yl)phenyl]-4-methyl-1-piperazinecarboxamide maleate To a stirred solution, under nitrogen of 24.5 g (0.10 mole) of 1-(2-amino-4-chlorophenyl)indoline (prepared from the compound of Example 4a via a method analagous to that of Example 3b) and 30.3 g (0.30 mole) of triethylamine in 450 ml of chloroform was added 29.9 g (0.15 mole) of 4-methyl-1-piperazinecarbonyl chloride hydrochloride in portions over 5 minutes. The reaction was refluxed for 6 hours when an additional charge of 15.2 g (0.15 mole) of triethylamine and 19.9 g (0.10 mole) of the carbonyl chloride reagent was added. After refluxing overnight (about 16 hours), the reaction was cooled, treated with 400 ml of water and stirred vigorously for 15 minutes. The layers were separated and the organic phase was washed thrice with water, dried over $Na_2SO_4$, and concentrated in vacuo. The residue was dissolved in 150 ml of toluene and adsorbed on a tall chromatography column containing 1.5 kg of silica gel packed in toluene. Elution first with toluene, then with increasing percentages of dichloromethane in toluene (25% per step), followed by dichloromethane alone, and finally increasing percentages of methanol in dichloromethane (1% per step) brought forth with 3% methanol in dichloromethane 12 g (overall 32% yield) of pure urea which crystallized. The 12 g (0.032 mole) was dissolved in 100 ml of ether, filtered, and the stirred solution was treated dropwise with a solution of 4.64 g (0.040 mole) of maleic acid in 180 ml of ether and 20 ml of ethanol. The finely divided maleate salt was collected, dried and found to weigh 10.7 g (22% overall yield). Recrystallization from 200 ml of methanol (charcoal) to which 400 ml of ether was then added afforded 7.8 g (16% overall yield) of N-[5-chloro-2-(2,3-dihydro-1H-indol-1-yl)phenyl]-4-methyl-1-piperdazinecarboxamide maleate, m.p. 165°–166° C. dec.

ANALYSIS: Calculated for $C_{20}H_{23}ClN_4O \cdot C_4H_4O_4$: 59.20%C 5.59%H 11.51%N. Found: 59.03%C 5.52%H 11.14%N.

c.

9-Chloro-6-(4-methyl-1piperazinyl)-1,2-dihydrobenzo[b]pyrrolo[3,2,1-jk][1,4]benzodiazepine A stirred solution of 6.30 g (0.017 mole) of N-[5-chloro-2-(2,3-dihydro-1H-indol-1-yl)-phenyl]-4-methyl-1piperazinecarboxamide of Example 4b in 100 ml of phosphorus oxychloride was refluxed for 6 hours under nitrogen, then cooled to room temperature. The excess phosphorus oxychloride was removed at aspirator pressure with gentle warming. The residue was chilled in an ice-bath (with exclusion of moisture) and then treated first with 250 ml of ice-cold 2N-NaOH, then with 250 ml of dichloromethane. The mixture was stirred vigorously until all the material passed into solution. The organic phase was separated, washed four times with water, dried over $Na_2SO_4$ and concentrated in vacuo to 5.7 g (95%) of a semi-crystalline material. Recrystallization from acetone afforded 2.20 g (37% overall yield) of 9-chloro-6-(4-methyl-1-piperazinyl)-1,2-dihydrobenzo[b]pyrrolo[3,2,1-jk][1,4]benzodiazepine, m.p. 154°–156° C.

ANALYSIS: Calculated for $C_{20}H_{21}ClN_4$: 68.08%C 6.00%H 15.88%N. Found: 67.85%C 6.00%H 15.63%N.

EXAMPLE 5 a.

1-(4-Methyl-2-nitrophenyl)indoline

A stirred mixture of 216 g (1.00 mole) of 4-bromo-3-nitrotoluene, 179 g (1.50 mole) of indoline and 182 g (1.50 mole) of collidine in 500 ml of xylene was refluxed for 3 days under nitrogen. After cooling to room temperature, the precipitated collidine hydrobromide salt was removed by filtration. The xylene filtrate was then washed with water, thrice with dilute HCl, once with dilute NaOH, again with water, then dried over $Na_2SO_4$ and concentrated to an oil. This material was dissolved in 250 ml of methanol from which 91 g (36% yield) of product crystallized having a melting point of 93°–95° C. A portion was recrystallized from methanol to afford 1-(4-methyl-2-nitrophenyl)indoline, m.p. 93°–95° C.

ANALYSIS: Calculated for $C_{15}H_{14}N_2O_2$: 70.85%C 5.55%H 11.02%N. Found: 70.94%C 5.62%H 11.08%N.

b.

1-(2-Amino-4-methylphenyl)indoline Hydrochloride

A Parr bottle, charged with 15.3 g (0.060 mole) of 1-(4-methyl-2-nitrophenyl)indoline of Example 5a, 100 ml of benzene, 100 ml of absolute ethanol, and 1.00 g of 5% Pd/C catalyst, was shaken under an initial 60 psi pressure of hydrogen until uptake ceased. The catalyst was then removed by filtration and the filtrate was concentrated in vacuo to an oil weighing 13.1 g (97%). This was dissolved in 50 ml of methanol and then 50 ml of ether saturated with hydrogen chloride was added. An additional 300 ml of plain ether was added to maximize precipitation. The hydrochloride salt was collected, dried, and found to weight 15.0 g (96%). Recrystallization twice from methanol-ether afforded 8.1 g (52% overall yield) of 1-(2-amino-4-methylphenyl)indoline hydrochloride, m.p. 203°–206° C.

ANALYSIS: Calculated for $C_{15}H_{16}N_2 \cdot HCl$: 69.09%C 6.57%H 10.75%N. Found: 68.97%C 6.94%H 10.44%N.

c.

N-[5-methyl-2-(2,3-dihydro-1H-indol-1-yl)phenyl]-4-methyl-1-piperazinecarboxamide Maleate To a stirred solution, under nitrogen of 43.0 g (0.190 mole) of 1-(2-amino-4-methylphenyl)indoline of Example 5b and 105 g (0.76 mole) of milled potassium carbonate in 1000 ml of chloroform was added 56.7 (0.285 mole) of 4-methyl-1-piperazinecarbonyl chloride hydrochloride in portions over 10 minutes. The reaction was refluxed for 7 hours, when an additional charge of 13.1 g (0.095 mole) of potassium carbonate and 18.9 g (0.095 mole) of the carbonyl chloride reagent was added. After refluxing overnight (about 16 hours), the reaction was cooled, treated with 500 ml of water, and stirred vigorously for 15 minutes. The layers were separated and the organic phase was washed thrice with water, dried over $NaSO_4$, and concentrated in vacuo to a semi-solid weighing 77 g. This was dissolved in 200 ml of methanol and treated with a solution of 24.4 g of maleic acid in 100 ml of methanol. This afforded 37.7 g (43% overall yield) of crystalline maleate salt. This salt was reversed back to the free base urea, yielding 18.1 g. This material was dissolved in 50 ml of dichloromethane and absorbed on a tall chromatography column containing 300 g of silica gel packed in dichloromethane. Elution first with dichloromethane, followed by 25% methanol/75% dichloromethane brought forth 16.2 g (24% overall yield) of pure urea. This (0.046 mole) was dissolved in 50 ml of methanol and treated with a solution of 5.92 g (0.051 mole) of maleic acid dissolved in 25 ml of methanol. The resulting maleate salt was recrystallized from methanol to afford 12.6 g of N-[5-methyl-2-(2,3-dihydro-1H-indol-1-yl)-phenyl]-4- methyl-1-piperazinecarboxamide maleate, m.p. 173°-175° C. dec.

ANALYSIS: Calculated for $C_{21}H_{26}N_4O.C_4H_4O_4$: 64.36%C 6.48%H 12.01%N. Found: 64.36%C 6.36% H 12.15%N.

d.

9-Methyl-6-(4-methyl-1-piperazinyl)-1,2-dihydrobenzo[b]pyrrolo[3,2,1-jk][1,4]benzodiazepine A stirred mixture of 35.1 (0.10 mole) of N-[5-methyl-2-(2,3-dihydro-1H-indol-1-yl)phenyl]-4-methyl-1-piperazinecarboxamide of Example 5c in 500 ml of phosphorus oxychloride was refluxed for 6 hours under nitrogen, then cooled to room temperature. The excess phosphorus oxychloride was removed at aspirator pressure with gentle warming. The residue was chilled in an ice-bath (with exclusion of moisture), and then treated first with 250 ml of ice-cold 2N-NaOH, then with 500 ml of chloroform. The mixture was stirred vigorously until all the material passed into solution. The organic phase was separated, washed thrice with water, and concentrated in vacuo to an oil. This was dissolved in 100 ml of boiling acetone, then allowed to crystallize at room temperature to afford 13.5 g (41% overall yield) of 9-methyl-6-(4-methyl-1-piperazinyl)-1,2-dihydrobenzo[b]pyrrolo[3,2,1-jk][1,4]-benzodiazepine, m.p. 160°-162° C.

ANALYSIS: Calculated for $C_{21}H_{24}N_4$: 75.87% C 7.28%H 16.85%N. Found: 75.98%C 7.54%H 16.48%N.

EXAMPLE 6 a.

N-[2-(2,3-Dihydro-1H-indol-1-yl)-5-( , , -trifluoromethyl)phenyl]-4-methyl-1-piperazinecarboxamide Maleate To a stirred solution, under nitrogen of 27.8 g (0.10 mole) of 1-(2-amino-4-trifluoromethylphenyl)indoline and 30.3 g (0.30 mole) of triethylamine in 450 ml of chloroform was added 29.9 g (0.15 mole) of 4-methyl-1-piperazinecarbonyl chloride hydrochloride in portions over about 5 minutes. The reaction was refluxed for 3 hours when an additional 15.2 g (0.15 mole) of triethylamine and 15.0 g (0.075 mole) of the carbonyl chloride reagent were added. After refluxing overnight (about 16 hours), the reaction was cooled, treated with 400 ml of water and stirred vigorously for 15 minutes. The layers were separated and the organic phase was washed twice with water, dried over $Na_2SO_4$, and concentrated in vacuo to leave 41.1 g. This material was dissolved in 100 ml of 1:1 $C_6H_5CH_3:CH_2CL_2$ and absorbed on a tall chromatography column containing 1 kg of silica gel packed in toluene. Elution first with 1:1 $C_6H_5CH_3:CH_2Cl_2$, and then with 100% $CH_2Cl_2$ brought forth 20.2 g (50% overall yield) of pure urea which crystallized. 8.6 g (0.021 mole) of urea were converted to the maleate salt in the following manner. The pure urea was dissolved in 20 ml of water ethanol and a solution of 2.67 g (0.023 mole) of maleic acid in 15 ml of ethanol was added. Then 20 ml of ether was added which caused rapid crystallization of N-[2-(2,3-dihydro-1H-indol-1-yl)-5-( , , -trifluoromethyl)phenyl-4-methyl-1-piperazinecarboxamide maleate. This was collected and found to weigh 8.2 g (75% yield) and had m.p. 173°-175° C. dec.

ANALYSIS: Calculated for $C_{21}H_{23}F_3N_4O.C_4H_4O_4$: 57.69%C 5.23%H 10.76%N. Found: 57.43%C 5.17%H 11.09%N.

b.

6-(4-Methyl-1-piperazinyl)-9-trifluoromethyl-1,2-dihydrobenzo[b]pyrrolo[3,2,1-jk][1,4]benzodiazepine A stirred mixture of 19.0 g (0.047 mole) of N-[2-(2,3-dihydro-1H-indol-1-yl)-5-( , , -trifluoromethyl)phenyl]-4-methyl-1-piperazinecarboxamide of Example 6a and 190 ml of phosphorus oxychloride was heated under nitrogen to reflux. Shortly thereafter, a solution resulted and this was refluxed for 7 hours, then cooled to room temperature. The excess phosphorus oxychloride was removed at aspirator pressure with gentle warming. The residue was treated first with 400 ml of 2N sodium hydroxide solution, then with 400 ml of dichloromethane. The mixture was stirred until all the material passed into solution. The organic phase was separated, washed twice with dilute brine, dried over $Na_2SO_4$, and concentrated to 16 g (88%) of a crystalline solid. Recrystallization from acetone afforded 7.7 g (42% overall yield) of 6-(4-methyl-1-piperazinyl)-9-trifluoromethyl-1,2-dihydrobenzo[b]pyrrolo[3,2,1-jk][1,4]benzodiazepine, m.p. 177°-180° C.

ANALYSIS: Calculated for $C_{21}H_{21}F_3N_4$: 65.27%C 5.48%H 14.50%N. Found: 65.45%C 5.46%H 14.57%N.

EXAMPLE 7 a.

N-[2-(2,3-Dihydro-1H-indol-1-yl)phenyl]-4-methyl-1-piperazinecarboxamide Maleate To a stirred solution, under nitrogen, of 21.0 g (0.10 mole) of 1-(2-aminophenyl)indoline and 30.4 g (0.30 mole) of triethylamine in 400 ml of chloroform was added 29.9 g (0.15 mole) of 4-methyl-1-piperazinecarbonyl chloride hydrochloride in portions over about 5 minutes. The reaction was refluxed for 6 hours when an additional 10.1 g (0.10 mole) of triethylamine and 19.9 g (0.10 mole) of 4-methyl-1-piperazinecarbonyl chloride hydrochloride were added. After refluxing overnight (total of 25 hrs), the reaction was cooled, treated with 400 ml water, and stirred vigorously for 15 minutes. The layers were separated and the organic phase was washed twice with water, dried over $Na_2SO_4$, and concentrated in vacuo. The residue was dissolved in 100 ml of absolute ethanol and treated in one portion with a warm solution of 13.2 g (0.11 mole) of maleic acid in 50 ml of ethanol. After several hours, the crystals were collected, washed with ethanol, and dried to afford 19.2 g (43%), of product, m.p. 158° dec. An additional 4.5 g of pure salt was obtained from the mother liquor making the total amount of product 23.7 g and the yield 53%. 3.0 g of product were recrystallized from ethanol to provide 2.80 g of N-[2-(2,3-dihydro-1H-indol-1-yl)phenyl]-4-methyl-1-piperazinecarboximide maleate.

ANALYSIS: Calculated for $C_{20}H_{24}N_4O.C_4H_4O_4$: 63.70%C 6.24%H 12.38%N. Found: 63.96%C 6.25%H 12.49%N.

b.

6-(4-Methyl-1-piperazinyl)-1,2-dihydrobenzo[b]pyrrolo[3,2,1-jk][1,4]benzodiazepine To 21.1 g (0.0627 mole) of N-[2-(2,3-dihydro-1H-indol-1-yl)phenyl]-4-methyl-1-piperazinecarboxamide of Example 7a was added 500 ml of phosphorus oxychloride and this was refluxed under nitrogen overnight. The excess POCl3 was then removed at aspirator pressure with warming. The residue was boiled and triturated on the steam bath with 60 ml of absolute ethanol until solution resulted. This solution was cooled and stirred resulting in separation of a solid. This solid was collected, washed with ethanol, with ether, and finally hexane, then dried to afford 19.0 g. This was partitioned between 200 ml of chloroform and 100 ml of water, with good stirring. Addition of 2.5N-NaOH rendered the medium basic, and the product base passed into the organic phase. This was separated, washed twice with water, dried over Na2SO4 and concentrated to 6.5 g of an oil. This oil was boiled with 60 ml of acetone, filtered from some insolubles, and the filtrate concentrated under nitrogen to 20 ml and allowed to crystallize. This gave 2.6 g of solid, m.p. 144°–146° C. dec. This material was treated with 20 ml of 2N-HCl with stirring. The resulting solution was filtered from a small amount of insolubles, then made basic with 2.5N-NaOH and the product extracted into dichloromethane. The latter extract was washed twice with water, dried over Na2SO4, and concentrated to an oil which began to crystallize. This was quickly dissolved in a small volume of boiling acetone and allowed to crystallize. The crystals were collected, washed with a little acetone, and dried to afford 2.00 g (10% overall yield) of 6-(4-methyl-1-piperazinyl)-1,2-dihydrobenzo[b]pyrrolo[3,2,1-jk][1,4]benzodiazepine, m.p. 149°–151° C.

ANALYSIS: Calculated for $C_{20}H_{22}N_4$: 75.44%C 6.96%. Found: 75.56%C 6.95%H.

EXAMPLE 8 a.

5-Chloro-1-(4chloro-2-nitrophenyl)indoline

A stirred solution of 123 g (0.80 mole) of 5-chloroindoline, 134 g (0.70 mole) of 1,4-dichloronitrobenzene and 97 g (0.80 mole) of collidine in 1000 ml of dimethylformamide was heated under nitrogen at 150° C. for 48 hours. The mixture was then cooled, filtered from some insolubles, and the solvent was removed in vacuo with warming. The residue was partitioned between 1000 ml of dichloromethane and 500 ml of water. The water layer was removed and the organic phase was washed twice with 2N-hydrochloric acid, once with 2N-sodium hydroxide, once more with water, dried over Na2SO4 and concentrated to an oil weighing 230 g. This was dissolved in 170 ml of methanol and stirred at room temperature and then at 0° C. The resultant crystals were collected, washed well with cold methanol, and dried. This afforded 86.5 g (40% yield) of product, m.p. 130°–133° C. 4 g of 5-chloro-1-(4-chloro-2-nitrophenyl)indoline were recrystallized from methanol in 85% yield (overall yield: 34%); m.p. 133°–135° C.

ANALYSIS: Calculated for $C_{14}H_{10}Cl_2N_2O_2$: 54.39%C 3.26%H 9.06%N. Found: 54.36%C 3.31%H 9.14%N.

b.

1-(2-Amino-4-chlorophenyl)-5-chloroindoline Hydrochloride Ethanolate

A Parr bottle, charged with 12.4 g (0.040 mole) of 5-chloro-1-(4-chloro-2-nitrophenyl)indoline of Example 8a, 100 ml of benzene, 100 ml of absolute ethanol and 0.5 g of 1% Pt/C was shaken under an initial hydrogen pressure of 57 psig until uptake ceased. The catalyst was then removed by filtration and the filtrate was concentrated in vacuo to an oil weighing 11.2 g (100%). This was dissolved in 30 ml of ethanol and then 30 ml of ether saturated with hydrogen chloride was added. An additional 500 ml of plain ether was added, and the mixture was stirred at 0° C., to maximize precipitation. The hydrochloride salt was collected, dried, and found to weigh 9.2 g (73%), m.p. 174°–178° C. Recrystallization from ethanol (charcoal) afforded 1-(2-amino-4-chlorophenyl)-5-chloroindoline hydrochloride ethanolate in 58% overall yield, m.p. 177°–180° C.

ANALYSIS: Calculated for $C_{14}H_{12}Cl_2N_2 \cdot HCl \cdot C_2H_6O$: 53.13%C 5.30%H 7.75%N. Found: 53.25%C 5.28%H 7.78%N.

c.

N-[5-Chloro-2-(5-chloroindol-2,3-dihydro-1H-1-yl)phenyl]-4-methyl-1-piperazinecarboxamide It is predicted that if the 1-(2-amino-4-chlorophenyl)-5-chloroindoline of Example 8b is employed and treated in the manner of Example 4b that N-[5-chloro-2-(5-chloroindol-2,3-dihydro-1H-1-yl)phenyl]-4-methyl-1-piperazinecarboxamide will be obtained.

d.

4,9-Dichloro-6-(4-methyl-1-piperazinyl)-1,2-dihydrobenzo[b]pyrrolo[3,2,1-jk][1,4]benzodiazepine It is predicted that if the N-[5-chloro-2-(5-chlorindol-2,3-dihydro-1H-1-yl)phenyl]-4-methyl-1-piperazinecarboxamide of Example 8c is employed and treated in the manner of Example 4c that 4,9-dichloro-6-(4-methyl-1-piperazinyl)-1,2-dihydrobenzo[b][pyrrolo[3,2,1-jk][1,4]benzodiazepine will be obtained.

EXAMPLE 9 a.

1-(4-Methoxy-2-nitrophenyl)indoline

A stirred mixture of 37.5 g (0.20 mole) of 4-chloro-3-nitroanisole, 35.8 g (0.30 mole) of indoline and 36.4 g (0.30 mole) of collidine in 100 ml of xylene was refluxed for 6 days. The mixture was then concentrated to an oil. This was partitioned between 1000 ml of dichloromethane and 500 ml of water. The organic phase was separated and extracted once more with water, then twice with dilute hydrochloric acid, once with dilute sodium hydroxide, twice more with water, then dried over sodium sulfate, and finally concentrated in vacuo, leaving an oil (38 g). This was dissolved in 150 ml of toluene and adsorbed on a tall chromatography column containing 1.5 kg of silica gel packed in toluene. Elution with toluene brought forth fractions containing 11.8 g (22% overall yield) of product which crystallized. This was recrystallized from isopropyl ether to afford 1-(4-methoxy-2-nitrophenyl)indoline, m.p. 88°–90° C.

ANALYSIS: Calculated for $C_{15}H_{14}N_2O_3$: 66.65%C 5.22%H 10.37%N. Found: 66.85%C 5.12%H 10.52N.

b.

1-(2-Amino-4-methoxyphenyl)indoline

It is predicted that if 1-(4-methoxy-2-nitrophenyl)indoline of Example 9a is employed and treated in the manner of Example 5b that 1-(2-amino-4-methoxyphenyl)indoline hydrochloride will be obtained.

c.

N-[2-(2,3-dihydro-1H-indol-1-yl)-5-methoxyphenyl]-4-methyl-1-piperazinecarboxamide It is predicted that if the 1-(2-amino-4-methoxyphenyl)indoline of Example 9b is employed and treated in the manner of Example 4b that N-[2-(2,3-dihydro-1H-indol-1-yl)-5-methoxyphenyl]-4-methyl-1-piperazinecarboxamide will be obtained.

d.

9-Methoxy-6-(4-methyl-1-piperazinyl)-1,2-dihydrobenzo[b]pyrrolo[3,2,1-jk][1,4]benzodiazepine It is predicted that if the N-[2-(2,3-dihydro-1H-indol-1-yl)-5-methoxyphenyl]-4-methyl-1-piperazinecarboxamide of Example 9c is employed and treated in the manner of Example 4c that 9-methoxy-6-(4-methyl-1-piperazinyl)-1,2-dihydrobenzo[b]pyrrolo[3,2,1-jk][1,4]benzodiazepine will be obtained.

EXAMPLE 10 a.

1-(4-Methylthio-2-nitrophenyl)indoline

To a stirred solution, under nitrogen, of 10.3 g (0.04 mole) of 1-(4-fluoro-2-nitrophenyl)indoline of Example 2a in 100 ml of hexamethylphosphoramide (HMPA) was added in portions 8.64 g (0.16 mole) of lithium methyl mercaptide. This resulted in a rapid exotherm from 18° to 40° C. The mixture was heated at 90° C. for 3 hours when an additional 4.32 g (0.08 mole) of lithium methyl mercaptide was added. After two more hours at 90° C., the mixture was cooled and quenched into 1 liter of ice/water, with good stirring. The product was extracted into 300 ml of ether, and the aqueous extracted twice more with ether. The combined ether phases were washed four times with water, dried over $Na_2SO_4$, and concentrated to a oil weighing 11.9 g. This was dissolved in 50 ml of toluene and adsorbed on a tall chromatography column containing 1200 g of silica gel, packed in toluene. Elution with toluene brought forth fractions containing 6.0 g (53% overall yield) of product. This was recrystallized from toluene-hexane to afford 1-(4-methylthio-2-nitrophenyl)indoline, m.p. 67°–69° C.

ANALYSIS: Calculated for $C_{15}H_{14}N_2O_2S$: 62.91%C 4.93%H 9.79%N. Found: 63.02%C 5.01%H 9.80%N.

b.

1-(2-Amino-4-methylthiophenyl)indoline

It is predicted that if the 1-(4-methylthio-2-nitrophenyl)indoline of Example 10a is treated in the manner of Example 5b that 1-(2-amino-4-methylthiophenyl)indoline will be obtained.

c.

N-[5-methylthio-2-(2,3-dihydro-1H-indol-1-yl)phenyl]-4-methyl-1-piperazinecarboxamide It is predicted that if the 1-(2-amino-4-methylthiophenyl)indoline of Example 10b is treated in the manner of Example 4b that N-[5-methylthio-2-(2,3-dihydro-1H-indol-1-yl)phenyl]-4-methyl-1-piperazinecarboxamide will be obtained.

d.

9-Methylthio-6-(4-methyl-1-piperazinyl)-1,2-dihydrobenzo[b]pyrrolo[3,2,1-jk][1,4]benzodiazepine It is predicted that if the N-[5-methylthio-2-(2,3-dihydro-1H-indol-1-yl)phenyl]-4-methyl-1-piperazinecarboxamide of Example 10c is treated in the manner of Example 4c that 9-methylthio-6-(4-methyl-1-piperazinyl)-1,2-dihydrobenzo[b]pyrrolo[3,2,1-jk][1,4]benzodiazepine will be obtained.

EXAMPLE 11 a.

1-(4-Methylsulfonyl-2-nitrophenyl)indoline

A stirred mixture of 47.7 g (0.40 mole) of indoline, 47.1 g (0.20 mole) of 4-chloro-3-nitrophenyl methyl sulfone, 36.4 g (0.30 mole) of collidine in 500 ml of xylene was refluxed under nitrogen for 2 days. The liquid was then decanted while hot from the crust of salt and concentrated. The residue was partitioned between dichloromethane and water. The organic phase was separated, washed once with water, twice with dilute HCl, once with dilute NaOH, twice more with water, then dried over $Na_2SO_4$, and concentrated. The residue was dissolved in 200 ml of hot acetone and allowed to crystallize on cooling. This afforded 40.8 g (64% yield) of product. This was recrystallized from acetone to yield 1-(4-methylsulfonyl-2-nitrophenyl)indoline, m.p. 151.5°–154° C.

ANALYSIS: Calculated for $C_{15}H_{14}N_2O_4S$: 56.60%C 4.43%H 8.80%N. Found: 56.70%C 4.66% H 8.85%N.

b.

1-(2-Amino-4-methylsulfonylphenyl)indoline

It is predicted that if the 1-(4-methylsulfonyl)-2-nitrophenyl)indoline of Example 11a is treated in the manner of Example 5b that 1-(2-amino-4-methylsulfonylphenyl)indoline will be obtained.

c.

N-[5-Methylsulfonyl-2-(2,3-dihydro-1H-indol-1-yl)phenyl]-4-methyl-1-piperazinecarboxamide It is predicted that if the 1-(2-amino-4-methylsulfonylphenyl)indoline of Example 11b is treated in the manner of Example 4b that N-[5-methylsulfonyl-2-(2,3-dihydro-1H-indol-1-yl)phenyl]-4-methyl-1-piperazinecarboxamide will be obtained.

d.

9-Methylsulfonyl-6-(4-methyl-1-piperazinyl)-1,2-dihydrobenzo[b]pyrrolo[3,2,1-jk][1,4]benzodiazepine It is predicted that if the N-[5-methylsulfonyl-2-(2,3-dihydro-1H-indol-1-yl)phenyl]-4-methyl-1-piperazinecarboxamide of Example 11c is treated in the same manner of Example 4c that 9-methylsulfonyl-6-(4-methyl-1-piperazinyl)-1,2-dihydrobenzo[b]pyrrolo[3,2,1-jk][1,4]benzodiazepine will be obtained.

EXAMPLE 12 a.

N-[2-(5-Chloro-2,3-dihydro-1H-indol-1-yl)phenyl]-4-methyl-1-piperazinecarboxamide maleate To a stirred solution, under nitrogen, of 24.5 g (0.10 mole) of 1-(2-aminophenyl)-5-chloroindoline and 30.4 g (0.30 mole) of triethylamine in 400 ml of chloroform was added 29.9 g (0.15 mole) of 4-methyl-1-piperazinecarbonyl chloride hydrochloride in portions over 5 minutes. The reaction was refluxed for 6 hours when an additional 15.2 g (0.15 mole) of triethylamine and 15.0 g (0.075 mole) of the piperazinecarbonyl chloride.HCl were added. After refluxing overnight (about 16 hours), the reaction was cooled, treated with 400 ml of water, and stirred vigorously for 15 minutes. The layers were separated and the organic phase was washed twice with water, dried over $Na_2SO_4$, and concentrated. The residue was dissolved in toluene and adsorbed on a tall chromatography column containing 1.5 kg. of silica gel packed with toluene. Elution first with toluene, then with increasing percentages of dichloromethane in toluene (25% per step), followed by increasing percentages of methanol in dichloromethane (1% per step) brought forth 9.8 g of urea (26% yield), using 4% methanol in dichloromethane. A solution of 7.42 g (0.020 mole) of the urea in 50 ml of ether was treated dropwise with a solution of 2.32 g (0.020 mole) of maleic acid in 150 ml of ether. The crystals so formed weighed 6.9 g (18% overall yield), m.p. 147°–149° C. dec. This was dissolved in ethanol, boiled with charcoal, filtered and treated with ether to form 4.2 g of N-[2-(5-chloro-2,3-dihydro-1H-indol-1-yl)phenyl]-4-methyl-1-piperazinecarboxamide maleate, m.p. 150°–152° C.

ANALYSIS: Calculated for $C_{20}H_{23}ClN_4O.C_4H_4O_4$: 59.20%C 5.59%H 11.51%N. Found: 59.06%C 5.70%H 11.32%N.

b.

6-(4-Methyl-1-piperazinyl)-4-chloro-1,2-dihydrobenzo[b]pyrrolo[3,2,1-jk][1,4]benzodiazepine It is predicted that if the N-[2-(5-chloro-2,3-dihydro-1H-indol-1-yl)phenyl]-4-methyl-1-piperazinecarboxamide of Example 12a is treated in the manner of Example 4c that 6-(4-methyl-1-piperazinyl)-4-chloro-1,2-dihydrobenzo[b]pyrrolo[3,2,1-jk][1,4]benzodiazepine will be obtained.

EXAMPLE 13

2-(5-Bromo-indolin-1-yl)benzamide

A slurry was prepared from 5-bromoindoline (9.85 g, 50 mmoles) dimethylsulfoxide (DMSO) (35 ml), sodium hydride (2.6 g, 50% in oil, washed with hexane, 1.1 eq). The slurry was stirred for 30 minutes. To this a solution of o-fluorobenzamide (7.9 g, 1.1 eq) in DMSO (15 ml) was added dropwise with temperature between 12°–13° C. At the end of addition the reaction mixture was stirred at ambient temperature for 4 hours, then heated up to 55° C. for 24 hours. The reaction mixture was partitioned between dichloromethane (300 ml) and water (250 ml). The aqueous phase was separated and extracted twice with dichloromethane (DCM) (150 ml). The combined DCM solution was washed twice with water (100 ml), twice with 2N HCl (100 ml), twice with brine (50 ml), dried over $Na_2SO_4$ and concentrated to a solid. Purification was on a flash chromatographic column (150 gm of silica gel) eluted with dichloromethane (DCM) (3 l). This gave 6.4 g of product (40%). Recrystallization from a small amount of ether yielded the 2-(5-bromo-indolin-1-yl)benzamide, m.p. 120°–122° C.

ANALYSIS: Calculated for $C_{15}H_{13}BrN_2O$: 56.80%C 4.13%H 8.83%N. Found: 57.09%C 4.25%H 8.90%N.

b.

2-(5-Bromo-7-nitro-1-indolinyl)benzamide It is predicted that if the 2-(5-bromo-indolin-1-yl)benzamide of Example 13a is treated in the manner of Example 1b that 1-(5-bromo-7-nitro-1-indolinyl)benzamide will be obtained.

c.

2-(5-Bromo-7-aminoindolin-1-yl)benzamide

It is predicted that if the 2-(5-bromo-7-nitro-1-indolinyl)benzamide of Example 13b is treated in the manner of Example 1c that 2-(5-bromo-7-aminoindolin-1-yl)benzamide will be obtained.

d.

4-Bromo-1,2-dihydrobenzo[c]pyrrolo[1,2,3-ef][1,5]benzodiazepin-7-one

It is predicted that if the 2-(5-bromo-7-aminoindolin-1-yl)benzamide of Example 13c is treated in the manner of Example 1d that 4-bromo-1,2-dihydrobenzo[c]pyrrolo[1,2,3-ef][1,5]benzodiazepin-7-one will be obtained.

e.

4-Bromo-7-(4-methyl-1-piperazinyl)-1,2-dihydrobenzo[c]pyrrolo[1,2,3-ef][1,5]benzodiazepine It is predicted that if the 4-bromo-1,2-dihydrobenzo[c]pyrrolo[1,2,3-ef][1,5]benzodiazepin-7-one of Example 13d is treated in the manner of Example 1e that 4-bromo-7-(4-methyl-1-piperazinyl)-1,2-dihydrobenzo[c]pyrrolo[1,2,3-ef][1,5]benzodiazepine will be obtained.

EXAMPLE 14

4-Bromo-6-(4-methyl-1-piperazinyl)-1,2-dihydrobenzo[b]pyrrolo[3,2,1-jk][1,4]benzodiazepine A mixture of N-[2-(5-bromo-1-indolinyl)phenyl]-4-methyl-1-piperazinecarboxamide (11.5 g, 27.5 mmoles) and 750 ml of phosphorus oxychloride was stirred until a solution was obtained and then heated under reflux for 40 minutes. The reaction mixture was cooled. Excess phosphorus oxychloride was removed by evaporation at 50°–55° C. The residue was dried for 30 minutes under vacuum. Ice-chilled 2N sodium hydroxide solution (250 ml) and dichloromethane (350 ml) were added to the residue at 4° C. (ice-water bath). The mixture was stirred until all the solid had dissolved. The organic phase was separated and washed with brine (2 times, 200 ml), dried over anhydrous magnesium sulfate and concentrated. Crystallization from ether (100 ml) gave 5.7 g (57%) of product. Recrystallization from isopropanol yielded the analytical sample, mp 203°–204° C.

ANALYSIS: Calculated for $C_{20}H_{21}BrN_4$: 60.46%C 5.33%H 14.10%N. Found: 60.51%C 5.45%H 14.03%N.

EXAMPLE 15

4-Chloro-6-(4-methyl-1-piperazinyl)-1,2-dihydrobenzo[b]pyrrolo[3,2,1-jk][1,4]benzodiazepine To N-[2-(5-chloro-1-indolinyl)phenyl]-4-methyl-1-piperazinecarboxamide (13.5 g, 36.5 mmoles) was added a solution of polyphosphoric acid ethyl ester and 1,2-dichloroethane (250 ml). The solution was heated at 75° C. for 4 hours with exclusion of moisture. The solution was cooled and poured into a mixture of ice-sodium hydroxide solution (2 l) and dichloromethane (1.2 l).

The mixture was stirred for 15 minutes. The layers were separated. The organic layer was washed with 2 l of 2N sodium hydroxide, then with brine (500 ml), and dried over anhydrous magnesium sulfate. Removal of the solvent at reduced pressure gave an oil. The oil was purified by flash chromatography on a silica gel column (1 kg, 230–400 mesh), packed and eluted initially with dichloromethane, then with dichloromethane containing an increasing methanol content in 1% increments to a final content of 5% (total 8 l). Concentration of the 5% methanol/dichloromethane eluent gave 3.8 g (28%) of product. Recrystallization from 2-propanol (50 ml) gave the analytical sample, mp 182°–183° C.

ANALYSIS: Calculated for $C_{20}H_{21}ClN_4$: 68.08%C 6.00%H 15.88%N. Found: 68.03%C 6.03%H 15.80%N.

EXAMPLE 16

9-Bromo-6-(4-phenyl-1-piperazinyl)-1,2-dihydrobenzo[b]pyrrolo[3,2,1-jk][1,4]benzodiazepine A stirred mixture of 7.88 g (0.0250 mole) of 9-bromo-1,2-dihydrobenzo[b]pyrrolo[3,2,1-jk][1,4]benzodiazepine-6-one and 1200 ml of toluene was heated under nitrogen until a solution resulted. Then there was added 40.6 g (0.250 mole) of N-phenylpiperazine, followed by 14.2 g (0.075 mole) of titanium tetrachloride. The mixture was heated under reflux for three hours, cooled to room temperature and treated with 500 ml of 2N sodium hydroxide solution. After stirring vigorously for 15 minutes, the layers were separated. The aqueous phase was extracted with 300 ml of toluene. The toluene layers were combined, washed once with 2N sodium hydroxide solution, twice with water, dried over anhydrous sodium sulfate, and concentrated to an oil. The oil was taken up in 80 ml of hot methanol, from which the product crystallized, affording 7.8 g (68%) of product. Recrystallization from a hot solution of dichloromethane (25 ml), to which methanol (25 ml) was added, provided the analytical sample, mp 171°–173° C.

ANALYSIS: Calculated for $C_{25}H_{23}BrN_4$: 65.36%C 5.05%H 12.20%N. Found: 65.25%C 5.08%H 12.27%N.

EXAMPLE 17

9-Bromo-6-(4-phenylmethyl-1-piperazinyl)-1,2-dihydrobenzo[b]pyrrolo[3,2,1-jk][1,4]benzodiazepine A stirred mixture of 7.88 g (0.0250 mole) of 9-bromo-1,2-dihydrobenzo[b]pyrrolo[3,2,1-jk][1,4]benzodiazepine-6-one and 1200 ml of toluene was heated under nitrogen until a solution resulted. Then there was added 44.1 g (0.250 mole) of N-benzylpiperazine, followed by 14.2 g (0.0750 mole) of titanium tetrachloride. The mixture was heated under reflux for 3 hours, cooled to room temperature and treated with 500 ml of 2N sodium hydroxide. After stirring vigorously for 15 minutes, the layers were separated. The aqueous phase was extracted further with 300 ml of toluene. The toluene layers were combined, washed once with 2N sodium hydroxide solution, twice with water, dried over anhydrous sodium sulfate, and concentrated in vacuo. The residue was taken up in 50 ml of hot methanol, from which 7.00 g (59%) of product crystallized. Recrystallization from a solution of dichloromethane (10 ml) to which methanol (50 ml) was added afforded the analytical sample, mp 129°–131° C.

ANALYSIS: Calculated for $C_{26}H_{25}BrN_4$: 65.96%C 5.32%H 11.84%N. Found: 65.67%C 5.54%H 11.52%N.

EXAMPLE 18

9-Bromo-6-(4-n-propyl-1-piperazinyl)-1,2-dihydrobenzo[b]pyrrolo[3,2,1-jk][1,4]benzodiazepine A stirred mixture of 7.88 g (0.0250 mole) of 9-bromo-1,2-dihydrobenzo[b]pyrrolo[3,2,1-jk][1,4]benzodiazepin-6-one and 1200 ml of toluene was heated until a solution resulted. Then there was added 32.1 g (0.25 mole) of N-propylpiperazine, followed by 14.2 g (0.075 mole) of titanium tetrachloride. The mixture was refluxed for 3 hours, and then cooled to room temperature. The mixture was stirred with 500 ml of 2N sodium hydroxide solution for 15 minutes and the layers were separated. The aqueous phase was extracted with 300 ml of toluene. The toluene layers were combined, filtered, washed once with 2N sodium hydroxide solution, twice with water, dried over anhydrous sodium sulfate, and concentrated to an oily solid. The oily solid was dissolved in 25 ml of hot ethyl acetate, filtered, and allowed to crystallize first at room temperature, then at 0° C. to yield 3.20 g (30%) of product, mp 134°–136° C.

ANALYSIS: Calculated for $C_{22}H_{25}BrN_4$: 62.12%C 5.92%H 13.17%N. Found: 61.84%C 5.81%H 12.82%N.

EXAMPLE 19

9-Bromo-6-(4-ethoxycarbonyl-1-piperazinyl)-1,2-dihydrobenzo[b]pyrrolo[3,2,1-jk][1,4]benzodiazepine A stirred mixture of 7.88 g (0.025 mole) of 9-bromo-1,2-dihydrobenzo[b]pyrrolo[3,2,1-jk][1,4]benzodiazepine-6-one and 1200 ml toluene was heated under nitrogen until a solution resulted. Then there was added 39.6 g (0.250 mole) of ethyl N-piperazinocarboxylate followed by 14.2 g (0.075 mole) of titanium tetrachloride. The mixture was heated under reflux for three hours, cooled to room temperature and treated with 500 ml of 2N sodium hydroxide solution. After stirring vigorously for 15 minutes, the layers were separated. The aqueous phase was extracted with 300 ml of toluene. The toluene layers were combined, washed once with 2N sodium hydroxide solution, twice with water, dried over anhydrous sodium sulfate, and concentrated in vacuo. The residue was taken up in 25 ml of hot methanol from which 8.5 g (75%) of product crystallized. Recrystallization from ethyl acetate gave the analytical sample, mp 128°–131° C.

ANALYSIS: Calculated for $C_{22}H_{23}BrN_4O_2$: 58.03%C 5.09%H 12.30%N. Found: 57.98%C 5.03%H 12.22%N.

EXAMPLE 20

4-Bromo-6-(4-methyl-1-piperazinyl)benzo[b]pyrrolo[3,2,1-jk][1,4]benzodiazepine

To a solution of 4-bromo-6-(4-methyl-1-piperazinyl)-1,2-dihydrobenzo[b]pyrrolo[3,2,1-jk][1,4]benzodiazepine (5.7 g, 14.3 mmoles) in chloroform (100 ml) was added manganese dioxide (5 g) and the mixture was heated at gentle reflux for 24 hours. Additional manganese dioxide was added and reflux was continued for 36 hours. The mixture was filtered and the solids were washed with dichloromethane. The filtrate was concentrated at reduced pressure. The residue was purified on a silica gel column (160 g), eluted with a mixture of methanol and dichloromethane (1.5% methanol in dichloromethane, 4 l, 2% methanol in dichloromethane, 2 l). The fractions containing pure product were combined and concentrated to give 3.7 g (64%) of product. Recrystallization from toluene (23 ml) yielded the analytical sample, mp 157°–159° C.

ANALYSIS: Calculated for $C_{20}H_{19}BrN_4$: 60.77%C 4.84%H 14.17%N. Found: 60.71%C 4.88%H 14.16%N.

EXAMPLE 21

4-Chloro-6-(4-methyl-1-piperazinyl)benzo[b]pyrrolo[3,2,1-jk][1,4]benzodiazepine

To a solution of 4-chloro-6-(4-methyl-1-piperazinyl)-1,2-dihydrobenzo[b]pyrrolo[3,2,1-jk][1,4]benzodiazepine (6 g, 17 mmoles), in chloroform (150 ml) was added manganese dioxide (10.5 g). The mixture was heated under reflux for 24 hours. The mixture was cooled, filtered and the solid was washed with dichloromethane (200 ml). The filtrate was then concentrated to dryness. The residue was purified by flash chromatography over a silica gel column (150 g), eluted with 2% methanol in dichloromethane (4 l) and 3% methanol in dichloromethane (2 l). Evaporation of the eluent gave 3.8 g (63%) of product. Recrystallization from toluene (40 ml) yielded the analytical sample, mp 170°–172° C.

ANALYSIS: Calculated for $C_{20}H_{19}ClN_4$: 68.47%C 5.46%H 15.97%N. Found: 68.68%C 5.64%H 16.06%N.

EXAMPLE 22

9-Methyl-6-(4-methyl-1-piperazinyl)benzo[b]pyrrolo[3,2,1-jk][1,4]benzodiazepine

A mixture of 4.97 g (0.020 mole) of 9-methylbenzo[b]pyrrolo[3,2,1-jk][1,4]benzodiazepin-6-one in 1000 ml of dry toluene was heated under nitrogen, with stirring, until a clear solution resulted. There was then added 20.0 g (0.20 mole) of N-methylpiperazine, followed by 11.4 g (0.060 mole) of titanium tetrachloride. The resulting mixture was heated under reflux for 3 hours, cooled to room temperature and 500 ml of 2N sodium hydroxide solution was added. After stirring vigorously for 15 minutes, the layers were separated. The aqueous phase was extracted with 250 ml of toluene, and the organic layers were combined, washed twice with dilute brine, dried over anhydrous sodium sulfate, and concentrated in vacuo to give 6.56 g (100%) of product. Recrystallization from ethyl acetate afforded the analytical sample, mp 202°–204° C.

ANALYSIS: Calculated for $C_{21}H_{22}N_4$: 76.33%C 6.71%H. Found: 76.26%C 6.80%H.

EXAMPLE 23

9-Bromo-6-(4-methyl-1-piperazinyl)benzo[b]pyrrolo[3,2,1-jk][1,4]benzodiazepine

A mixture of 6.16 g (0.020 mole) of 9-bromobenzo[b]pyrrolo[3,2,1-jk][1,4]benzodiazepin-6-one in 1000 ml of dry toluene was heated under nitrogen until a clear solution resulted. There was then added 20.0 g (0.20 mole) of N-methylpiperazine, followed by 11.4 g (0.060 mole) of titanium tetrachloride. The resulting mixture was heated under reflux for three hours, cooled to room temperature and filtered. The filtrate was stirred vigorously with 500 ml of 2N sodium hydroxide solution for 15 minutes, and the layers were separated. The organic layer was washed twice with dilute brine, dried over anhydrous sodium sulfate, and concentrated in vacuo to an oil which crystallized to provide 8.0 g (100%) of product. Recrystallization from ethanol afforded the analytical product, mp 164°–166° C.

ANALYSIS: Calculated for $C_{20}H_{19}BrN_4$: 60.76%C 4.84%H 14.17%N. Found: 60.58%C 4.88%H 14.13%N.

EXAMPLE 24

4-Methyl-7-(4-methyl-1-piperazinyl)-1,2-dihydrobenzo[c]pyrrolo[1,2,3-ef][1,5]benzodiazepine A solution of 4-methyl-1,2-dihydrobenzo[c]pyrrolo[1,2,3-ef][1,5]benzodiazepin-7-one (3.6 g, 14.3 mmoles), N-methylpiperazine (16 ml) and toluene (350 ml) was heated to 110° C. Titanium tetrachloride (4.3 ml) was added in three portions in two minute intervals. The mixture was heated under reflux for two hours and cooled to room temperature. Toluene (500 ml) and ice-water (500 m) were added. The mixture was stirred for 30 minutes and the insoluble material was removed by filtration. The organic phase was separated. The aqueous phase was extracted with toluene (200 ml). The combined toluene solutions were washed with water (300 ml), brine (2 times, 300 ml) and dried over anhydrous sodium sulfate. The solvent was evaporated. The residue was triturated with ethanol:hexane to a solid. Recrystallization of the solid from chloroform:hexane yielded 2.4 g of product. The mother liquor was concentrated and the residue was purified on a silica gel column (60 g, 230–400 mesh) to give a second crop of 1.3 g of product (77% overall yield). Recrystallization from 2-propanol gave the analytical sample, mp 173°–174° C.

ANALYSIS: Calculated for $C_{21}H_{24}N_4$: 75.87%C 7.28%H 16.85%N. Found: 75.52%C 7.32%H 16.69%N.

EXAMPLE 25

4-Methyl-7-(4-methyl-1-piperazinyl)benzo[c]pyrrolo[1,2,3-ef][1,5]benzodiazepine

To a solution of 4-methylbenzo[c]pyrrolo[1,2,3-ef][1,5]benzodiazepine-7-one (3.2 g, 13.1 moles), N-methylpiperazine (13.5 ml, 131 mmoles) and toluene (300 ml) at 120° C., was added titanium tetrachloride (4.5 ml) in one portion. The mixture was heated for 30 minutes and then cooled to room temperature. Toluene (500 ml) and ice-water (1 l) were added. The mixture was stirred for 15 minutes. The insoluble material was filtered off. The layers of the filtrate were separated and the aqueous phase was extracted with toluene (200 ml). The combined organic extracts were washed with brine (3 times, 300 ml), dried over anhydrous sodium sulfate and concentrated. The residue was purified by flash chromatography on a silica gel column (200 g, 230–400 mesh). Elution with 2.5% methanol in dichloromethane gave 2.8 g (65%) of product. Recrystallization from 2-propanol yielded the analytical sample, mp 167°–168° C.

ANALYSIS: Calculated for $C_{21}H_{22}N_4$: 76.33%C 6.71%H 16.96%N. Found: 76.28%C 6.84%H 16.84%N.

EXAMPLE 26

4-Chloro-7-(4-methyl-1-piperazinyl)benzo[c]pyrrolo[1,2,3-ef][1,5]benzodiazepine

A mixture of 4-chlorobenzo[c]pyrrolo[1,2,3-ef][1,5]benzodiazepin-7-one (2.6 g, 9.7 mmoles), N- methylpiperazine (11 ml, 97 mmoles) and toluene (250 ml) was heated to 100° C. over 25 minutes. Titanium tetrachloride (2.5 ml) was added in one portion. The mixture was heated under reflux for 2 hours, with stirring, and then cooled to room temperature. Toluene (300 ml) and water (150 ml) were added. The mixture was stirred for 20 minutes. The insoluble material was filtered off. The layers of the filtrate were separated and the aqueous phase was extracted with toluene (200 ml). The combined toluene extracts were washed with water (2 times, 200 ml), brine (200 ml), dried over anhydrous sodium sulfate and concentrated to yield 3.0 g, (88%) of product. Recrystallization from dichloromethane (25 ml)/hexane (40 ml) gave the analytical sample, mp 184°–186° C.

ANALYSIS: Calculated for $C_{20}H_{19}ClN_4$: 68.47%C 5.46%H 15.97%N. Found: 68.19%C 5.48%H 15.83%N.

EXAMPLE 27

9-Methyl-6-(4-methyl-1-piperidinyl)-1,2-dihydrobenzo[b]pyrrolo[3,2,1-jk][1,4]benzodiazepine A stirred mixture of 6.26 g (0.0250 mole) of 9-methyl-1,2-dihydrobenzo[b]pyrrolo[3,2,1-jk][1,4]benzodiazepin-6-one and 1000 ml of toluene was heated under nitrogen until a solution resulted. Then there was added 24.8 g (0.250 mole) of 4-methylpiperidine, followed by 14.2 g (0.075 mole) of titanium tetrachloride. The mixture was heated under reflux for three hours, cooled to room temperature and filtered. The filtrate was stirred with 500 ml of 2N sodium hydroxide solution for 15 minutes and the layers were separated. The aqueous phase was extracted with 250 ml of toluene. The toluene layers were combined, washed once with 2N sodium hydroxide solution, twice with water, dried over anhydrous sodium sulfate, filtered, and concentrated in vacuo to 8.1 g (98%) of product. Recrystallization from ethyl acetate provided the analytical sample, mp 194°–196° C.

ANALYSIS: Calculated for $C_{22}H_{25}N_3$: 79.72%C 7.60%H 12.68%N. Found: 79.90%C 7.66%H 12.72%N.

EXAMPLE 28

9-Bromo-6-(4-methyl-1-piperidinyl)-1,2-dihydrobenzo[b]pyrrolo[3,2,1-jk][1,4]benzodiazepine A mixture of 4.73 g (0.0150 mole) of 9-bromo-1,2-dihydrobenzo[b]pyrrolo[3,2,1-jk][1,4]benzodiazepin-6-one and 1000 ml of toluene was heated under nitrogen, with stirring, until a solution resulted. Then there was added 14.9 g (0.150 mole) of 4-methylpiperidine, followed by 8.54 g (0.045 mole) of titanium tetrachloride. The mixture was refluxed for 3 hours, cooled to room temperature and filtered. The filtrate was stirred with 500 ml of 2N sodium hydroxide solution for 15 minutes and the layers were separated. The aqueous phase was extracted with 250 ml of toluene. The toluene layers were combined, washed once with 2N sodium hydroxide solution, twice with water, dried over anhydrous sodium sulfate, filtered, and concentrated in vacuo to an oil which solidified. The solid was triturated twice with hexane to afford 4.9 g (83%) of product. Recrystallization from ethyl acetate provided the analytical sample, mp 177°–179° C.

ANALYSIS: Calculated for $C_{21}H_{22}BrN_3$: 63.64%C 5.60%H 10.60%N. Found: 63.53%C 5.57%H 10.64%N.

EXAMPLE 29

9-Bromo-6-(4-morpholinyl)-1,2-dihydrobenzo[b]pyrrolo[3,2,1-jk][1,4]benzodiazepine A mixture of 7.88 g (0.0250 mole) of 9-bromo-1,2-dihydrobenzo[b]pyrrolo[3,2,1-jk][1,4]benzodiazepin-6-one and 1200 ml of toluene was heated under nitrogen, with stirring, until a solution resulted. Then there was added 21.8 g (0.250 mole) of morpholine, followed by 14.2 g (0.075 mole) of titanium tetrachloride. The mixture was heated under reflux for three hours, cooled to room temperature and treated with 500 ml of 2N sodium hydroxide solution. After stirring vigorously for 15 minutes, the layers were separated. The aqueous phase was extracted with 250 ml of toluene. The toluene layers were combined, washed once with 2N sodium hydroxide solution, twice with water, dried over anhydrous sodium sulfate, filtered, and concentrated in vacuo to 8.6 g (90%) of product. Recrystallization from a hot solution of dichloromethane (80 ml) to which methanol (80 ml) was added provided the analytical sample, mp 216°–218° C.

ANALYSIS: Calculated for $C_{19}H_{18}BrN_3O$: 59.38%C 4.72%H 10.94%N. Found: 59.31%C 4.75%H 11.08%N.

EXAMPLE 30

9-Bromo-6-(4-thiomorpholinyl)-1,2-dihydrobenzo[b]pyrrolo[3,2,1-jk][1,4]benzodiazepine A mixture of 7.88 g (0.025 mole) of 9-bromo-1,2-dihydrobenzo[b]pyrrolo[3,2,1-jk][1,4]benzodiazepin-6-one and 1200 ml of toluene was heated under nitrogen, with stirring, until a solution resulted. Then there was added 25.8 g (0.250 mole) of thiomorpholine, followed by 14.2 g (0.075 mole) of titanium tetrachloride. The mixture was heated under reflux for 3 hours, cooled to room temperature and treated with 500 ml of 2N sodium hydroxide solution. After stirring vigorously for 15 minutes, the layers were separated. The aqueous phase was extracted with 300 ml of toluene. The toluene layers were combined, washed once with 2N sodium hydroxide solution, twice with water, dried over anhydrous sodium sulfate, filtered, and concentrated in vacuo. The residue was crystallized from 100 ml of hot methanol to give 8.8 g (88%) of product. Recrystallization from a hot solution of dichloromethane (50 ml, charcoal) to which methanol (100 ml) was added provided the analytical sample, mp 165°–167° C.

ANALYSIS: Calculated for $C_{19}H_{18}BrN_3S$: 57.00%C 4.53%H 10.50%N. Found: 56.90%C 4.53%H 10.46%N.

EXAMPLE 31

4-Chloro-7-(4-methyl-1-piperidinyl)benzo[c]pyrrolo[1,2,3-ef][1,5]benzodiazepine

A mixture of 4-chlorobenzo[c]pyrrolo[1,2,3-ef][1,5]benzodiazepin-7-one (3.0 g, 11 mmole), toluene (450 ml), and 4-methylpiperidine (15 ml, 110 mmoles) was heated to 110° C., with stirring. Titanium tetrachloride (3.5 ml) was added slowly in one portion. The mixture was heated under reflux for 1 hour. The mixture was cooled and diluted with toluene (250 ml). The mixture was washed with cold water (500 ml) and the insoluble material was collected. The aqueous phase was separated and extracted twice with toluene (300 ml and 150 ml). The combined toluene extracts were washed with brine (2 times, 300 ml), dried over anhydrous sodium sulfate, filtered, and concentrated. The residue was purified by flash chromatography on silica gel (125 g, 230–400 mesh), eluted with 1:1 hexane:dichloromethane (2 l) and 8:2 dichloromethane:hexane (1 l). The fractions containing desired products were collected and evaporated to give 3.8 g (97%) of product. Recrystallization from dichloromethane and hexane afforded the analytical sample, mp 162°–163° C.

ANALYSIS: Calculated for $C_{21}H_{20}ClN_3$: 72.09%C 5.76% H 12.01%N. Found: 72.14%C 5.83%H 12.02%N.

EXAMPLE 32

4-Chloro-7-(4-methyl-1-piperidinyl)-1,2-dihydrobenzo[c]pyrrolo[1,2,3-ef][1,5]benzodiazepine To a mixture of 4-chloro-1,2-dihydrobenzo[c]pyrrolo[1,2,3-ef][1,5]benzodiazepin-7-one (4.5 g, 16 mmole), toluene (150 ml) and 4-methylpiperidine (18 ml, 0.15 mole), a solution of titanium tetrachloride (11 g, 58 mmoles) in toluene (5 ml) was added dropwise. The mixture was heated under reflux at 120° C. for three hours. The mixture was filtered and the solid was partitioned between sodium chloride solution (50% saturated, 550 ml) and ether (800 ml). The organic phase was separated. The aqueous phase was extracted twice with ether (400 ml). The combined organic extracts were washed with brine (2 times, 350 ml), dried over anhydrous sodium sulfate, filtered, and evaporated. The residue was washed with a small amount of ethanol. Recrystallization from chloroform:heptane yielded 4.62 g (78%) of product. The analytical sample was prepared by recrystallization from dichloromethane, mp 238°–239° C.

ANALYSIS: Calculated for $C_{21}H_{22}ClN_3$: 71.68%C 6.30%H 11.94%N. Found: 71.82%C 6.29%H 12.17%N.

EXAMPLE 33

4-Methyl-7-amino-1,2-dihydrobenzo[c]pyrrolo[1,2,3-ef][1,5]benzodiazepine hydrochloride To a solution of 2-(5-methyl-B 7-nitroindolin-1-yl)benzonitrile (11 g, 39.4 mmoles), dimethylformamide (150 ml) and ethanol (150 ml) was added 5% palladium-carbon (2.0 g). The mixture was shaken under hydrogen (59 psi) for 24 hours. The mixture was filtered and the filtrate was concentrated. The residue was dissolved in the minimum volume of ethanol and ethereal hydrogen chloride was added to give 3.37 g (35%) of product. Recrystallization from hot ethanol afforded the analytical sample, mp >250° C.

ANALYSIS: Calculated for $C_{16}H_{15}N_3$ HCl: 67.25%C 5.64%H 14.70%N. Found: 67.33%C 5.69%H 14.81%N.

EXAMPLE 34

9-Bromo-6-[(3-dimethylamino)propylamino]-1,2-dihydrobenzo[b]pyrrolo[3,2,1-jk][1,4]benzodiazepine A mixture of 7.88 g (0.025 mole) of 9-bromo-1,2-dihydrobenzo[b]pyrrolo[3,2,-jk][1,4]benzodiazepin-6-one and 1200 ml of toluene was heated under nitrogen, with stirring, until a solution resulted. Then there was added 25.5 g (0.250 mole) of 3-dimethylaminopropylamine, followed by 14.2 g (0.075 mole) of titanium tetrachloride. The mixture was heated under reflux for three hours, cooled to room temperature and treated with 500 ml of 2N sodium hydroxide solution. After stirring vigorously for 15 minutes, the layers were separated. The aqueous phase was extracted with 300 ml of toluene. The toluene layers were combined, washed once with 2N sodium hydroxide solution, twice with water, dried over anhydrous sodium sulfate, filtered and concentrated. The residue was dissolved in 80 ml of boiling ethyl acetate, and the solution was concentrated to 30 ml. The crystals were collected to give 7.8 g (78%) of product. Recrystallization from 50 ml of methanol afforded the analytical sample, mp 126°–129° C.

ANALYSIS: Calculated for $C_{20}H_{23}BrN_4$: 60.15%C 5.81%H 14.03%N. Found: 60.04%C 5.85%H 14.14%N.

EXAMPLE 35

9-Bromo-6-[(2-dimethylamino)-N-methylethylamino]-1,2-dihydrobenzo[b]pyrrolo[3,2,1-jk][1,4]benzodiazepine Dimaleate salt A mixture of 7.88 g (0.0250 mole) of 9-bromo-1,2-dihydrobenzo[b]pyrrolo[3,2,1-jk][1,4]benzodiazepin-6-one and 1200 ml of toluene was heated under nitrogen, with stirring, until a solution resulted. There was then added 25.5 g (0.25 mole) of N,N,N'-trimethylethylenediamine, followed by 14.2 g (0.075 mole) of titanium tetrachloride. The resulting mixture was heated under reflux for three hours, cooled to room temperature and treated with 500 ml of 2N sodium hydroxide solution. After stirring vigorously for 15 minutes, the layers were separated. The aqueous layer was extracted with 300 ml of toluene. The combined toluene layers were washed once with 2N sodium hydroxide solution, twice with water, dried over anhydrous sodium sulfate, filtered, and concentrated in vacuo to an oil. The oil was dissolved in 30 ml of warm ethanol and was treated with a solution of 3.27 g (0.028 mole) of maleic acid dissolved in 20 ml of hot ethanol. After standing at room temperature for 1 hour, and at 0° C. for one hour, the crystals were collected to give 6.1 g (47%) of product, mp 179°–180° C. dec.

ANALYSIS: Calculated for $C_{20}H_{23}BrN_4 2C_4H_4O_4$: 53.19%C 5.10%H 8.86%N. Found: 53.25%C 4.95%H 8.87%N.

EXAMPLE 36

9-Bromo-6-dimethylamino-1,2-dihydrobenzo[b]pyrrolo[3,2,1-jk][1,4]benzodiazepine

A mixture of 10.8 g (0.030 mole) of N-[5-bromo-2-(2,3-dihydro-1H-indol-1-yl)phenyl]-N',N'-dimethylurea and 110 ml of phosphorus oxychloride, under nitrogen, was heated under reflux for 6 hours, with stirring, and then cooled to room temperature. The excess phosphorus oxychloride was removed under vacuum with gentle warming. The residue was chilled in an ice-bath (with exclusion of moisture) and treated first with 250 ml of ice-cold 2N sodium hydroxide solution, and then with 500 ml of dichloromethane. The mixture was stirred and triturated until all the material passed into solution. The organic phase was separated, washed with 2N sodium hydroxide solution, twice with water, dried over anhydrous sodium sulfate, filtered, and concentrated in vacuo to an oil. The oil was dissolved in 50 ml of ethyl acetate and the solution was concentrated under a stream of nitrogen. At a volume of about 30 ml, the mixture was filtered. Concentration of the filtrate was continued to a volume of about 20 ml, during which crystallization resulted. The solid was dissolved by heating, the hot solution was filtered and allowed to crystallize to afford 4.9 g (48%) of product, mp 124°–127° C.

ANALYSIS: Calculated for $C_{17}H_{16}BrN_3$: 59.66%C 4.71%H 12.28%N. Found: 59.50%C 4.69%H 12.21%N.

EXAMPLE 37

4-Methyl-1,2-dihydrobenzo[c]pyrrolo[1,2,3-ef][1,5]benzodiazepin-7-one

To a solution of 2-(5-methyl-7-nitroindolin-1-yl)benzoic acid (9 g, 0.03 mole), conc. hydrochloric acid (several drops) and ethanol (200 ml) was added 5% palladium-charcoal (1.5 gm). The mixture was shaken under hydrogen (58 psi) for 30 hours. The solvent was removed and the residue was loaded onto a silica gel flash chromatography column (800 g, 230–400 mesh), packed and eluted with dichloromethane (4 l) and 2% methanol in dichloromethane (4 l). The fractions containing product were pooled and evaporated to yield 5 g (66%) of product. Recrystallization from chloroform gave the analytical sample, mp 222°–224° C.

ANALYSIS: Calculated for $C_{16}H_{14}N_2O$: 76.76%C 5.64%H 11.12%N. Found: 76.41%C 5.63%H 11.21%N.

EXAMPLE 38

4-Methylbenzo[c]pyrrolo[1,2,3-ef][1,5]benzodiazepin-7-one

A solution of 4-methyl-1,2-dihydrobenzo[c]pyrrolo[1,2,3-ef][1,5]benzodiazepin-7-one (0.10 g, 0.40 mmole) in 30 ml of xylene was brought to reflux, with stirring, and 2,3-dichloro-5,6-dicyano-1,4-benzoquinone (0.12 g, 0.53 mmole) was added in one portion. After heating under reflux for 15 minutes, the reaction mixture was cooled and flash chromatographed on 15 g of silica gel (230–400 mesh), using dichloromethane as eluent, to afford 0.075 g (75%) of product, mp 228°–230° C.

ANALYSIS: Calculated for $C_{10}H_{12}N_2O$: 77.40%C 4.87%H 11.28%N. Found: 77.15%C 5.01%H 11.18%N.

EXAMPLE 39

4-Chlorobenzo[c]pyrrolo[1,2,3-ef][1,5]benzodiazepin-7-one

A solution of 4-chloro-1,2-dihydrobenzo[c]pyrrolo[1,2,3-e,f][1,5]benzodiazepin-7-one (7 g, 26 mmoles) in xylene (800 ml was heated at 100° C. for 15 minutes and 2,3-dichloro-5,6-dicyano-1,4-benzoquinone (7 g, 31 mmoles) was added in one portion. The mixture was stirred at 105° C. for 1.5 hours. The hot solution was filtered and the filtrate was cooled to 5° C. The crystals were collected and washed with ethanol (10 ml) to give 5.8 g (83%) of product. Recrystallization from hot ethanol (800 ml) afforded the analytical sample, mp 278°–280° C.

ANALYSIS: Calculated for $C_{15}H_9ClN_2O$: 67.05%C 3.38%H 10.42%N. Found: 66.74%C 3.45%H 10.39%N.

EXAMPLE 40

9-Bromo-1,2-dihydrobenzo[b]pyrrolo[3,2,1-jk][1,4]benzodiazepin-6-one

A mixture of 5.96 g (0.0150 mole) of 9-bromo-6-(4-methyl-1-piperazinyl)-1,2-dihydrobenzo[b]pyrrolo[3,2,1-jk][1,4]benzodiazepine and 100 ml of 2N hydrochloric acid was heated under reflux for 2 hours, with stirring, and then cooled to room temperature. The reaction mixture was filtered and the filter cake washed several times with water and dried to afford 3.92 g (83%) of product. Recrystallization from hot dimethylformamide provided the analytical sample, mp 255°–257° C.

ANALYSIS: Calculated for $C_{15}H_{11}BrN_2O$: 57.17%C 3.52%H 8.89%N. Found: 57.07%C 3.64%H 8.91%N.

EXAMPLE 41

9-Methyl-1,2-dihydrobenzo[b]pyrrolo[3,2,1-jk][1,4]benzodiazepin-6-one

A solution of 9.97 g (0.030 mole) of 9-methyl-6-(4-methyl-1-piperazinyl)-1,2-dihydrobenzo[b]pyrrolo[3,2,1-jk][1,4]benzodiazepine in 200 ml of 2N hydrochloric acid was heated under reflux for 1 hour, with stirring. The mixture was cooled to room temperature and filtered. The filter cake was washed several times with water and dried to afford 6.0 g (80%) of product. Recrystallization from hot dimethylformamide gave the analytical sample, mp 238°–240° C.

ANALYSIS: Calculated for $C_{16}H_{14}N_2O$: 76.77%C 5.64%H 11.20%N. Found: 77.01%C 5.73%H 11.43%N.

EXAMPLE 42

9-Methylbenzo[b]pyrrolo[3,2,1-jk][1,4]benzodiazepin-6-one

A mixture of 11.8 g (0.047 mole) of 9-methyl-1,2-dihydrobenzo[b]pyrrolo[3,2,1-jk][1,4]benzodiazepin-6-one and 1200 ml of xylene was heated under nitrogen, with stirring to 125° C. To the resulting solution was then added 21.3 g (0.094 mole) of 2,3-dichloro-5,6-dicyano-1,4-benzoquinone. The mixture was heated under reflux for 2 hours, allowed to cool to 120° C. and filtered. The filtrate was concentrated. The residue was triturated with 50 ml of methanol and the solid collected to afford 6.0 g (51%) of product. Recrystallization from 20 ml of hot dimethylformamide provided the analytical sample, mp 222°–225° C.

ANALYSIS: Calculated for $C_{16}H_{12}N_2O$: 77.40%C 4.87%H 11.29%N. Found: 77.12%C 4.91%H 11.44%N.

EXAMPLE 43

9-Bromobenzo[b]pyrrolo[3,2,1-jk][1,4]benzodiazepin-6-one

A mixture of 12.6 g (0.040 mole) of 9-bromo-1,2-dihydrobenzo[b]pyrrolo[3,2,1-jk][1,4]benzodiazepin-6-one and 1200 ml of xylene was heated under nitrogen, with stirring, to about 125° C., at which all of the solids had dissolved. To this solution was added 18.2 g (0.080 mole) of 2,3-dichloro-5,6-dicyano-1,4-benzoquinone. The mixture was heated under reflux for 2 hours. The reaction mixture was allowed to cool to 120° and filtered. The filtrate was stirred at ambient temperature for 3 hours. The material which separated was collected. The material was boiled and triturated with 50 ml of methanol and then filtered to afford 10.1 g (80%) of product. Recrystallization from 50 ml of hot dimethylformamide gave the analytical sample, mp 272°–274° C.

ANALYSIS: Calculated for $C_{15}H_9BrN_2O$: 57.53%C 2.90%H 8.95%N. Found: 57.48%C 2.94%H 9.00%N.

EXAMPLE 44

4-Chloro-1,2-dihydrobenzo[b]pyrrolo[3,2,1-jk][1,4]benzodiazepin-6-one

In the preparation of 4-chloro-6-(4-methyl-1-piperazinyl)-1,2-dihydrobenzo[b]pyrrolo[3,2,1-jk][1,4]benzodiazepine, a second component was isolated and purified by flash chromatography (dichloromethane eluent) to give 2.3 g (23%) of product. Recrystallization from dichloromethane gave the analytical sample, mp 232°–233° C.

ANALYSIS: Calculated for $C_{15}H_{11}ClN_2O$: 66.55%C 4.10%H 10.35%N. Found: 66.35%C 4.22%H 10.12%N.

EXAMPLE 45

N-[2-(5-bromo-1-indolinyl)phenyl]phenycarbamate

To a mixture of 1-(2-aminophenyl)-5-bromoindoline hydrochloride (2.2 g, 6.8 mmoles), triethylamine (3 g, 20.4 mmoles) and dichloromethane (30 ml) was added phenylchloroformate (1.33 g, 8.5 mmoles) at room temperature. The mixture was stirred for 1 hour. Additional phenyl chloroformate (0.26 g, 1.7 mmoles) was added and the reaction mixture was stirred for 20 minutes. The solvent was evaporated. The residue was purified by flash chromatography on a silica gel column (200 g, 230–400 mesh), eluted with a mixture of 10:90 dichloromethane:hexane (3 l), 15:85 dichloromethane:hexane (2 l) and 20:80 dichloromethane:hexane (2 l). The fractions containing pure material were combined and concentrated to give 1.93 g (70%) of product.

ANALYSIS: Calculated for $C_{21}H_{17}BrN_2O_2$: 61.63%C 4.19%H 6.84%N. Found: 61.71%C 4.29%H 6.82%N.

EXAMPLE 46

N-[2-(5-chloro-1-indolinyl)phenyl]phenylcarbamate

To a mixture of 1-(2-aminophenyl)-5-chloroindoline (24.0 g, 98.0 mmoles), triethylamine (20 ml, 143 mmoles) and dichloromethane (750 ml) was added dropwise, with stirring, phenylchloroformate (28 g, 178 mmoles) over a 30 minute period. After the addition was complete, the reaction mixture was concentrated to a small volume (50 ml) and flash chromatographed on 1 kg. of silica gel (230–400 mesh) using a solution of 2 parts hexane to 1 part dichloromethane as eluent to provide 24.6 g (68%) of product.

EXAMPLE 47

N-[5-Methoxy-2-(2,3-dihydro-1H-indol-1-yl)phenyl]-4-methyl-1-piperazinecarboxamide maleate To a stirred mixture, under nitrogen, of 24.0 g (0.10 mole) of 1-(2-amino-4-methoxyphenyl)indoline and 55.3 (0.40 mole) of milled potassium carbonate in 500 ml of chloroform was added 29.9 g (0.15 mole) of 4-methyl-1-piperazine carbonyl chloride hydrochloride in portions over 5 minutes. The reaction mixture was heated under reflux for 6 hours and additional potassium carbonate (6.91 g, 0.05 mole) and 4-methyl-1-piperazine carbonyl chloride hydrochloride (9.95 g, 0.05 mole) were added. The mixture was heated under reflux overnight, and a second addition of the same amounts of potassium carbonate and 4-methyl-1-piperazine carbonyl chloride hydrochloride charge was made. After heating under reflux for a total of 48 hours, the reaction mixture was cooled, treated with 500 ml of water, and stirred vigorously for 15 minutes. The layers were separated, and the organic phase was washed thrice with water, dried over anhydrous sodium sulfate, and concentrated. The residue was dissolved in a small volume of dichloromethane and adsorbed on a chromatography column containing 200 g of silica gel packed in dichloromethane. Elution with dichloromethane gave 16.6 g (45%) of product. A 9.1 g (0.025 mole) portion was dissolved in 30 ml of methanol and treated with a solution of 3.48 g (0.03 mole) of maleic acid in 10 ml of methanol. The precipitate was collected and dried to afford 10.5 g of product maleate, mp 161°–163° C. dec.

ANALYSIS: Calculated for $C_{21}H_{26}N_4O_2.C_4H_4O_4$: 62.22%C 6.27%H 11.61%N. Found: 62.16%C 6.51%H 11.53%N.

EXAMPLE 48

N-[5-Bromo-2-(2,3-dihydro-1H-indol-1-yl)phenyl]-N',N'-dimethyl urea

To a stirred mixture, under nitrogen, of 28.9 g (0.10 mole) of 1-(2-amino-4-bromophenyl)indoline hydrochloride and 16.8 g (0.20 mole) of anhydrous powdered sodium bicarbonate in 500 ml of chloroform was added a solution of 21.5 g (0.20 mole) of dimethylcarbamyl chloride in 25 ml of chloroform, over a 10 minute period. The mixture was heated under reflux for 7 hours, and 8.4 g (0.10 mole) of sodium bicarbonate and 10.7 g (0.10 mole) of the dimethylcarbamyl chloride were added. After heating under reflux for 2 days, equivalent amounts (8.4 g of sodium bicarbonate and 10.7 g of dimethylcarbamyl chloride) were added. After three days under reflux, the mixture was cooled and 500 ml of water was added. The phases were stirred vigorously for 0.5 hours and separated. The organic phase was washed three times with water, dried over anhydrous sodium sulfate and concentrated in vacuo. The residue was dissolved in 200 ml of dichloromethane and adsorbed on a chromatography column containing 1 kg of silica gel packed in and eluted with dichloromethane. The fractions containing product were combined and concentrated to afford 14.5 g (40%) of product. Recrystallization from toluene (charcoal)/hexane gave the analytical sample, mp 119°–121° C.

ANALYSIS: Calculated for $C_{17}H_{18}BrN_3O$: 56.67%C 5.04%H 11.66%N. Found: 56.80%C 5.14%H 11.82%N.

EXAMPLE 49

1-(2-Amino-4-methoxyphenyl)indoline maleate

A Parr bottle, charged with 3.30 g (0.0122 mole) of 1-(4-methoxy-2-nitrophenyl)indoline, 30 ml of benzene, 30 ml of ethanol, and 0.5 g of 5% palladium-on-charcoal was shaken under an initial pressure of 61 psi of hydrogen until uptake ceased. The catalyst was removed by filtration and the filtrate was concentrated to a residue. The residue was dissolved in 20 ml of ether and then a solution of 1.74 g (0.015 mole) of maleic acid in 80 ml of hot diethyl ether was added. The solution was concentrated to a small volume and the salt was allowed to crystallize. The precipitate was collected, filtered, washed with a little ether and dried to afford 2.80 (64%) of product as the maleate, mp 103°–105° C.

ANALYSIS: Calculated for $C_{15}H_{16}N_2O.C_4H_4O_4$: 64.03%C 5.66%H 7.87%N. Found: 63.91%C 5.80%H 7.80%N.

EXAMPLE 50

1-(2-Aminophenyl)-5-bromoindoline hydrochloride

To a warm solution of 2-(5-bromo-1-indolinyl)nitrobenzene (20 g, 0.062 mole) in dimethylformamide (100 ml) and ethanol (500 ml) was added 1% platinum-on-carbon (4.0 gm). The mixture was shaken under hydrogen (59 psi) for three hours. The mixture was filtered and the filtrate concentrated under vacuum at 55° C. The residue was purified by flash chromatography over silica gel (200 mg, 230–400 mesh), eluted with 1:1 hexane:dichloromethane (3 l). The fractions containing product were pooled and concentrated to give 14.5 g (80%) of product, as an oil. The oil was treated with ethanolic hydrogen chloride and the precipitate was collected. Recrystallization from 95% ethanol afforded the analytical sample of the product hydrochloride, mp 207°–210° C. dec.

ANALYSIS: Calculated for $C_{14}H_{13}BrN_2$ HCl: 51.64%C 4.33%H 8.60%N. Found: 51.67%C 4.28%H 8.59%N.

EXAMPLE 51

5-Bromo-1-(2-nitrophenyl)indoline

5-Bromoindoline (4.0 g, 0.02 mole), collidine (3.6 g, 0.03 mole), and o-fluoronitrobenzene (2.8 g, 0.02 mole) in xylene (25 ml) were heated at 185° C. (oil bath temperature) for 24 hours. The mixture was cooled to room temperature and poured into dichloromethane. The dichloromethane solution was washed with 1N hydrochloric acid (3 times, 150 ml), brine (200 ml), dried over anhydrous magnesium sulfate and filtered. The solvent was evaporated. Crystallization of the residue was induced by stirring in ether (15 ml) followed by hexane (200 ml), then chilling in the refrigerator overnight. The solid was filtered and washed with hexane and dried to yield 3.5 g (55%) of product. Recrystallization from 2-propanol yielded the analytical sample, mp 12°–114° C.

ANALYSIS: Calculated for $C_{14}H_{11}BrN_2O_2$: 52.69%C 3.47%H 8.78%N. Found: 53.01%C 3.50%H 8.95%N.

EXAMPLE 52

2-(5-Methyl-7-nitro-1-indolinyl)benzoic acid

A stirred solution under nitrogen of potassium hydroxide (30 g, 0.53 mole) in ethylene glycol (250 ml) and water (35 ml) was heated to 175° C., at which temperature there was added 2-(5-methyl-7-nitroindolin-1-yl)benzonitrile (26 g, 0.093 mole). After heating at 175° C. for 3 hours, the reaction mixture was cooled to room temperature and dichloromethane (1 liter) and water (500 ml), were added, with stirring. The aqueous phase was separated and extracted with two 250 ml-portions of dichloromethane. The aqueous phase was then cooled in an ice-bath and acidified with concentrated hydrochloric acid. The product was extracted out with three 500 ml-portions of dichloromethane. The combined organic extracts were washed twice with brine, dried, filtered, and concentrated to afford 9.0 g (32%) of product.

EXAMPLE 53

2-(5-Methyl-7-nitroindolin-1-yl)benzonitrile

A solution of 2-(5-methylindolin-1-yl)benzonitrile (13.85 g, 59 mmoles) and silver nitrate (11 g, 64 mmoles) in acetonitrile (60 ml) was chilled to 5° C. A solution of acetyl chloride (5.6 g, 71 mmoles) in acetonitrile (2 ml) was slowly added dropwise. The reaction mixture was stirred at ambient temperature for 1.5 hours. The reaction mixture was diluted with dichloromethane (350 ml), filtered, and the filter cake was washed with dichloromethane (2 times, 100 ml). The combined organic solutions were washed with brine (250 ml), dried over anhydrous sodium sulfate and anhydrous potassium carbonate, filtered, and concentrated to afford 16.9 g (100%) of product. Recrystallization from ethanol gave the analytical sample, mp 138°–139° C.

ANALYSIS: Calculated for $C_{16}H_{13}N_2O_3$: 68.81%C 4.69%H 15.04%N. Found: 68.89%C 4.79%H 15.23%N.

EXAMPLE 54

2-(5-Methylindolin-1-yl)benzonitrile

A slurry of 5-methylindoline (31 g, 0.23 mole), sodium hydride (11.3 g, 60% in oil) and dimethylsulfoxide (120 ml) was stirred at room temperature for 1 hour. A solution of o-fluorobenzonitrile (31 gm, 0.25 mole) in dimethylsulfoxide (25 ml) was added dropwise at a temperature below 20° C. Upon completion of the addition, the mixture was stirred for 2 hours at room temperture. The reaction mixture was partitioned between methylene chloride (700 ml) and ice-water (700 ml). The dichloromethane solutions were separated. The aqueous phase was extracted with dichloromethane (2 times, 600 ml). The combined dichloromethane solutions were washed with 2N hydrochloric acid (2 times, 500 ml), water (500 ml), brine (2 times, 400 ml), dried over anhydrous sodium sulfate, filtered, and concentrated. The residue was dissolved in ethanol (300 ml) and heptane (100 ml), and chilled in a freezer. The precipitate was collected. The mother liquor was concentrated and purified by flash chromatography on a silica gel column (400 g, 230–400 mesh) eluted with hexane:dichloromethane (3:1, 3 l); hexane:dichloromethane (1:1, 2 l) and dichloromethane (2 l). The fractions containing product were pooled and concentrated to yield 33 g (73% overall yield). The analytical sample was prepared by high-pressure liquid chromatography (Water Associates Prep 500, 10 g, 2 chamber, elution with hexane:dichloromethane, 9:1, 12 l) followed by crystallization from ethanol, mp 59°–60° C.

ANALYSIS: Calculated for $C_{16}H_{14}N_2$: 82.02%C 6.02%H 11.96%N. Found: 82.47%C 6.08%H 12.10%N.

EXAMPLE 55

1-(2-Amino-4-methylsulfonylphenyl)indoline hydrochloride

A Parr bottle, charged with 9.55 g (0.030 mole) of 1-(4-methylsulfonyl-2-nitrophenyl)indoline, 250 ml of tetrahydrofuran, and 1.0 g of 5% palladium-on-charcoal, was shaken under an initial pressure of 60 psi of hydrogen until uptake ceased. The catalyst was removed by filtration and the filtrate was concentrated in vacuo. The residue was dissolved in 25 ml of methanol and then treated with 25 ml of ether saturated with hydrogen chloride gas. Diethyl ether (500 ml) was added. The supernatant ether was decanted. The residue was treated twice with fresh diethyl ether (100 ml) followed by decantation. The residue was taken up in hot methanol, boiled 5 minutes with charcoal, filtered, and the solution was treated with diethyl ether until a small amount of oil separated. The supernatant was separated and concentrated to give 7.3 g (74%) of product. The analytical sample was prepared by boiling and triturating the product with 50 ml of 4:1 ether:methanol, followed by recrystallization from methanol-ether, mp 198°–201° C.

ANALYSIS: Calculated for $C_{15}H_{16}N_2O_2S.HCl$: 55.46%C 5.28%H 8.63%N. Found: 55.79%C 5.29%H 8.65%N.

EXAMPLE 56

N-[2-(5-bromo-1-indolinyl)phenyl]-4-methyl-1-piperazinecarboxamide

A solution of N-[2-(5-bromo-1-indolinyl)phenyl]-phenylcarbamate (11.5 g, 28.5 mmoles), N-methylpiperazine (15 ml) and ether (50 ml) was stirred at room temperature for 2 hours. The ether was evaporated. The mixture was filtered through a silica gel column (150 g), packed with dichloromethaane, and the column was washed with 2% methanol-dichloromethane solution (2 l). The solvent was evaporated. The residue was purified by flash chromatography on a silica gel column (150 g, 230–400 mesh), eluted with 1% methanol/dichloromethane (4 l), 1.5% methanol/dichloromethane (2 l), and 2% methanol/dichloromethane. The fractions containing the desired material were collected and evaporated to give 10.9 g (90%) of product. Crystallization from chloroform and hexane afforded the analytical sample, mp 108°–110° C.

ANALYSIS: Calculated for $C_{20}H_{23}BrN_4O$: 58.32%C 5.58%H 13.49%N. Found: 58.10%C 5.58%H 13.39%N.

EXAMPLE 57

Starting with 6-bromotetrahydroquinoline and following steps 1a to 1d and 1f, or alternatively, 1a to 1c, 1e and 1f, of Example 1, one may obtain, in sequence, 2-(6-bromo-1,2,3,4-tetrahydroquinolin-1-yl)benzamide, 2-(6-bromo-8-nitro-1,2,3,4-tetrahydroquinolin-1-yl)benzamide, 2-(8-amino-6-bromo-1,2,3,4-tetrahydroquinolin-1-yl)benzamide, 5-bromo-2,3-dihydro-1H-quino[1,8-ab][1,4]benzodiazepin-8-one, and 5-bromo-8-(4-methyl-1-piperazinyl)-2,3-dihydro-1H-quino[1,8-ab][1,4]benzodiazepine.

EXAMPLE 58

Starting with 6-methyl-1,2,3,4-tetrahydroquinoline and 2-fluoronitrobenzene and following steps 1a to 1f of Example 2, one may obtain, in sequence, 6-methyl-1-(2-nitrophenyl)-1,2,3,4-tetrahydroquinoline, 1-(2-aminophenyl)-6-methyl-1,2,3,4-tetrahydroquinoline, N-[2-(6-methyl-1-phenyl)-1,2,3,4-tetrahydroquinolin-1-yl]-4-methyl-1-piperazine carboxamide, and 5-methyl-7-(4-methyl-1-piperazinyl)-2,3-dihydro-1H-quino[1,8-ab][1,5]benzodiazepine.

EXAMPLE 59

Starting with 1,2,3,4-tetrahydroquinoline and 5-bromo-2-fluoronitrobenzene and following the steps of 1a to 1f of Example 2, one may obtain, in sequence, 1-(4-bromo-2-nitrophenyl)-1,2,3,4-tetrahydroquinoline, 1-(2-amino-4-bromophenyl)-1,2,3,4-tetrahydroquinoline, N-[2-{1-(5-bromophenyl)-1,2,3,4-tetrahydroquinolin-1-yl}]-4-methyl-1-piperazine carboxamide, and 10-bromo-7-(4-methyl-1-piperazinyl)-2,3-dihydro-1H-quino[1,8-ab][1,5]benzodiazepine.

EXAMPLE 60

Starting with 1,2,3,4-tetrahydroquinoline and 5-chloro-2-fluoronitrobenzene and following the steps of 1a to 1f of Example 2, one may obtain, in sequence, 1-(4-chloro-2-nitrophenyl)-1,2,3,4-tetrahydroquinoline, 1-(2-amino-4-chlorophenyl)-1,2,3,4-tetrahydroquinoline, N-[2-{1-(5-chlorophenyl)-1,2,3,4-tetrahydroquinolin-1-yl}]-4-methyl-1-piperazine carboxamide, and 10-chloro-7-(4-methyl-1-piperazinyl)-2,3-dihydro-1H-quino[1,8-ab][1,5]benzodiazepine.

EXAMPLE 61

Starting with 1,2,3,4-tetrahydroquinoline and 2-fluoro-5-methylnitrobenzene and following the steps of 1a to 1f of Example 2, one may obtain, in sequence, 1-(4-methyl-2-nitrophenyl)-1,2,3,4-tetrahydroquinoline, 1-(2-amino-4-methylphenyl)-1,2,3,4-tetrahydroquinone, 1-(2-amino-4-methylphenyl)-1,2,3,4-tetrahydroquinoline, N-[2-{1-(5-methylphenyl)-1,2,3,4-tetrahydroquinolin-1-yl}]-4-methyl-1-piperazine carboxamide, and 10-methyl-7-(4-methyl-1-piperazinyl)-2,3-dihydro-1H-quino[1,8-ab][1,5]benzodiazepine.

EXAMPLE 62

1-(2-Nitrophenyl)-1,2,3,4-tetrahydroquinoline

A stirred mixture, under nitrogen of 70.6 g (0.50 mole) of 1-fluoro-2-nitrobenzene, 133.2 g (1.00 mole) of 1,2,3,4-tetrahydroquinoline and 121.2 g (1.00 mole) of symmetrical collidine in 500 ml of 1,2,3-trimethylbenzene was refluxed (bp 178°) for 5 days. The mixture was concentrated in vacuo. The residue was taken up in 1000 ml of chloroform and extracted with 500 ml of 2N-hydrochloric acid. The aqueous phase was back extracted with 250 ml of chloroform. The combined organic layers were washed 3 times with 2N-hydrochloric acid, once with 2N-sodium hydroxide solution, twice with water and dried over anhydrous sodium sulfate. The solvent was removed in vacuo. The residual oil was dissolved in 300 ml of 1:1 hexane:toluene and adsorbed on a chromatography column containing 2 kg of silica gel packed in hexane. Elution with 1:1 hexane:toluene gave fractions containing product. The fractions were combined and concentrated to afford 28.2 g (22%) of product. Recrystallization from hot isopropyl ether afforded the analytical sample, mp 69°–71° C.

ANALYSIS: Calculated for $C_{15}H_{14}N_2O$: 70.85%C 5.55%H 11.02%N. Found: 70.82%C 5.66%H 11.00%N.

EXAMPLE 63

1-(2-Aminophenyl)-1,2,3,4-tetrahydroquinoline maleate

A Parr hydrogenation bottle was charged with 12.7 g (0.050 mole) of 1-(2-nitrophenyl)-1,2,3,4-tetrahydroquinoline, 1.0 g of 5% palladium-on-charcoal, 100 ml of thiophene-free benzene and 100 ml of ethanol. The mixture was shaken under an initial hydrogen pressure of 55 psig until uptake ceased. The mixture was filtered to remove the catalyst and the filtrate was concentrated in vacuo to give 11.2 g (100%) of product, as an oil. An 8.4 g portion of the product was dissolved in 50 ml of ether and treated with a hot solution of 4.3 g of maleic acid in 350 ml of ether. The precipitate (8.4 g) was collected and melted at 119°–121° C. For analysis, the salt was recrystallized from hot ethanol to afford a sample melting at 119°–121° C.

ANALYSIS: Calculated for $C_{15}H_{16}N_2C_4H_4O_4$: 67.04%C 5.92%H 8.23%N. Found: 67.34%C 6.03%H 8.53%N.

EXAMPLE 64

9-Bromo-6-[(2-dimethylamino)ethylamino]-1,2-dihydrobenzo[b]pyrrolo[3,2,1-jk][1,4]benzodiazepine A stirred mixture of 7.88 g (0.0250) mole of 9-bromo-1,2-dihydrobenzo[b]pyrrolo[3,2,1-jk][1,4]benzodiazepin-6-one and 1200 ml of toluene was heated under nitrogen until a solution resulted. Then there was added 22.0 g (0.250 mole) of 2-(dimethylamino)ethylamine, followed by 14.2 g (0.075 mole) of titanium tetrachloride. The mixture was refluxed for three hours, cooled to room temperature and treated with 500 ml of 2N-sodium hydroxide solution. After stirring vigorously for 15 minutes, the layers were separated. The aqueous phase was extracted with 300 ml of toluene. The toluene layers were combined, washed once with 2N-sodium hydroxide solution, twice with water, dried over anhydrous sodium sulfate and concentrated. The residue was taken up into 100 ml of boiling ethyl acetate, filtered, and concentrated under a nitrogen stream to a volume of 25 ml. At this point, 50 ml of hexane were added. The precipitate was collected to give 6.60 g (67%), of product, mp 118°–122° C. Recrystallization from hot methanol to which hexane was added afforded the analytical sample, mp 119°–122° C.

ANALYSIS: Calculated for $C_{19}H_{21}BrN_4$: 59.22%C 5.49%H 14.54%N. Found: 59.45%C 5.50%H 14.72%N.

EXAMPLE 65

4-Bromo-6-(4-methyl-1-piperazinyl)-9-methyl-1,2-dihydrobenzo[b]pyrrolo[3,2,1-jk][1,4]benzodiazepine A solution of N-[2-(5-bromo-1-indolinyl)-5-methylphenyl]-4-methyl-1-piperazinecarboxamide (3.3 g, 7.68 mmoles) and phosphorus oxychloride (30 ml) was heated at reflux for 25 minutes under nitrogen. The solution was cooled and excess phosphorus oxychloride was removed at 55°–60° C. under vacuum. Ice-chilled 2N-sodium hydroxide solution (100 ml) and dichloromethane (250 ml) were added to the residue. The organic phase was separated and washed with brine (2 times, 100 ml), dried over anhydrous magnesium sulfate, and concentrated. Purification was accomplished by flash chromatography over aluminum oxide (Grade III, 100 g), eluted with dichloromethane (2 l). The fractions containing pure material were pooled and concentrated. Recrystallization from isopropanol (30 ml) yielded 1.7 g (53.9%) of product, mp 187°–189° C.

ANALYSIS: Calculated for $C_{21}H_{23}BrN_4$: 61.32%C 5.64%H 13.62%N. Found: 61.13%C 5.66%H 13.61%N.

EXAMPLE 66

9-Methoxy-6-(4-methyl-1-piperazinyl)-1,2-dihydrobenzo[b]pyrrolo[3,2,1-jk][1,4]benzodiazepine A stirred mixture of 9.90 g (0.027 mole) of N-[2-(2,3-dihydro-1H-indol-1-yl)-5-methoxyphenyl]-1-piperazinecarboxamide in 150 ml of phosphorus oxychloride was refluxed for 1 hour under nitrogen, then cooled to room temperature. The excess phosphorus oxychloride was removed at aspirator pressure at 50° C. The residue was chilled in an ice-bath (with exclusion of moisture), and treated first with 500 ml of ice-cold 2N-sodium hydroxide solution and then with 500 ml of dichloromethane. The mixture was stirred vigorously for 15 minutes and suction filtered through a pad of celite. The organic phase was separated, washed with 2N-sodium hydroxide solution, 4 times with water, dried and concentrated in vacuo. Crystallization from ethyl acetate afforded 3.90 g (42%) of product, mp 152°–155° C.

ANALYSIS: Calculated for $C_{21}H_{24}N_4O$: 72.39%C 6.94%H 16.08%N. Found: 72.45%C 6.95%H 16.14%N.

EXAMPLE 67

10-Bromo-9-methyl-6-(4-methyl-1-piperazinyl)-1,2-dihydrobenzo[b]pyrrolo[3,2,1-jk][1,4]benzodiazepine A solution of N-bromosuccinimide (0.91 g, 5.1 mmoles) in dimethylformamide (3 ml) was added dropwise to a solution of 6-(4-methyl-1-piperazinyl)-9-methyl-1,2-dihydrobenzo[b]pyrrolo[3,2,1-jk][1,4]benzodiazepine (1.6 g, 4.8 mmoles) in dimethylformamide (30 ml) at 0°–3° C. The reaction mixture was stirred for 30 minutes. The solution was poured into dichloromethane (250 ml), and was washed with brine (4 times, 150 ml), and dried over anhydrous magnesium sulfate. The solvent was removed at reduced pressure and the residue was dried. Purification was accomplished by flash chromatography on an aluminium oxide column (grade III, 60 g), eluted with dichloromethane (500 ml) and 2% methanol in dichloromethane (250 ml). The fractions containing the product were pooled and concentrated. Recrystallization from 2-propanol:water (1:1, 20 ml) yielded 230 mg (11.6%) of product, mp 177°–177° C.

ANALYSIS: Calculated for $C_{21}H_{23}BrN_4$: 61.32%C 5.64%H 13.62%N. Found: 61.69%C 5.72%H 13.60%N.

EXAMPLE 68

4-Bromo-6-(4-methyl-1-piperazinyl)-9-methylbenzo[b]pyrrolo[3,2,1-jk][1,4]benzodiazepine To a solution of 4-bromo-6-(4-methyl-1-piperazinyl)-9-methyl-1,2-dihydrobenzo[b]pyrrolo[3,2,1-jk][1,4]benzodiazepine (5.7 g, 13.8 mmoles) in chloroform (540 ml) was added manganese dioxide (25 gm), and the mixture was heated under reflux for 4 days. The mixture was filtered, and the filter cake washed with dichloromethane. The filtrate was concentrated under vacuum. The residue was purified on a silica gel column, eluted with 2% methanol/dichloromethane. The fractions (75–100 ml each) containing pure product were pooled and concentrated. Recrystallization from a small volume of 2-propanol yielded 2.41 g (42%) of product, mp 153°–155° C.

ANALYSIS: Calculated for $C_{21}H_{21}BrN_4$: 61.62%C 5.17%H 13.69%N. Found: 61.41%C 5.07%H 13.92%N.

EXAMPLE 69

4-(5-Bromo-1-indolinyl)-3-nitrotoluene

To a solution of N-(2-nitro-4-tolyl)indoline (28 g, 0.11 mole) in dimethylformamide (500 ml) was added dropwise a solution of N-bromosuccinimide (21.5 g, 0.12 mole) in dimethylformamide (110 ml) at −6° C. The reaction was stirred for 0.5 hour. The reaction mixture was poured into 2% sodium hydroxide-ice-water solution (2 l), with stirring. The precipitate was collected by filtration, and then dissolved into dichloromethane (2 l). The dichloromethane solution was washed with brine, (2 times, 1 l), dried over anhydrous magnesium sulfate and concentrated. The residue was triturated with hot isopropyl alcohol (60 ml); yield 30.3 g (84%). The isopropyl alcohol solution was concentrated. The residue was purified on a flash chromatography column, silica gel, 100 g, eluted with 3:1 hexane:dichloromethane (2 l) to give a second crop, 3.7 g of product. Recrystallization from hot isopropyl alcohol yielded the analytical sample, mp 105°–107° C.

ANALYSIS: Calculated for $C_{15}H_{13}BrN_2O_2$: 54.04%C 3.93%H 8.41%N. Found: 53.55%C 3.88%H 8.44%N.

EXAMPLE 70

1-(2-Amino-4-methylphenyl)-5-bromoindoline hydrochloride

To a warm solution of 4-(5-bromo-1-indolinyl)-3-nitrotoluene (10 g, 0.03 mole) in dichloromethane (40 ml) and ethanol (160 ml) was added 1% platinum-on-carbon (2.0 gm). The mixture was shaken under hydrogen (57 psi) for 3.5 hours. The mixture was filtered and concentrated. The residue was dried under vacuum at 55° C. Purification was accomplished by flash chromatography over silica gel (100 g), eluted with a mixture of hexane:dichloromethane (3:1, 2 l and 1:1, 1 l). The fractions containing pure product were pooled and concentrated. The residue was dissolved in ether (250 ml) and added to a methanol/hydrogen chloride solution, and the mixture was stirred at 0° C. for 10 minutes. The precipitate was filtered and dried to afford 4.0 g (39%) of product, mp 195°–200° C. dec.

ANALYSIS: Calculated for $C_{15}H_{15}BrN_2HCl$: 53.04%C 4.75%H 8.25%N. Found: 53.16%C 4.75%H 8.22%N.

EXAMPLE 71

N-[2-(5-bromo-1-indolinyl)-5-methylphenyl]phenylcarbamate

To a mixture of N-[2-amino-4-methylphenyl]-5-bromoindoline (9.0 g, 30 mmoles), triethylamine (10 ml) and dichloromethane (180 ml) was added phenylchloroformate (7.05 g, 45 mmoles) at 0° C. The reaction mixture was stirred for 2 hours at 0° C. and 1 hr at room temperature. At the end of three hours, silica gel (10 g) was added, and the solvent was removed at reduced pressure. The mixture was purified on a flash chromatography column (silica gel, 150 gm), eluted with 80%:20% hexane:dichloromethane (4 l). The fractions containing the pure product were combined and concentrated. The residue was further purified on a Water Associates Prep 500 high-pressure liquid chromatography apparatus, eluted with 90:10 hexane:dichloromethane (v/v). The fractions containing the desired product were pooled and concentrated to give 2.3 g (23%) of product as a colorless oil.

ANALYSIS: Calculated for $C_{22}H_{19}BrN_2O_2$: 62.42%C 4.52%H 6.62%N. Found: 63.16%C 4.85%H 6.42%N.

EXAMPLE 72

N-[2-(5-bromo-1-indolinyl)-5-methylphenyl]-4-methyl-1-piperazinecarboxamide

A solution of N-[2-(5-bromo-1-indolinyl)-5-methylphenyl]phenylcarbamate (24.0 g, 56 mmoles), N-methylpiperazine (24 ml) and ether (150 ml) was stirred at room temperature for 1 hour. After standing overnight at 0° C., the reaction mixture was allowed to stand at room tempertaure for 3 hours. Hexane (100 ml) and seed crystals were added. Crystallization was induced by stirring at room temperature for 2 hours, followed by briefly cooling to sub-zero temperature (acetone-dry ice bath). The crystals was filtered and dried to give 17.5 g (72%) of product. The analytical sample was prepared by flash chromatography (silica gel, 140 g; eluted with 1% methanol:dichloromethane, 6 l) followed by recrystallization from chloroform:hexane, and had mp 115°–117° C.

ANALYSIS: Calculated for $C_{21}H_{25}BrN_4O$: 58.75%C 5.87%H 13.05%N. Found: 58.83%C 5.84%H 13.13%N.

EXAMPLE 73

1-(2-Nitro-4-bromophenyl)-5-bromoindoline

To a solution of 1-(2-nitro-4-bromophenyl)indoline (15 g, 0.047 moles) in dimethylformamide (150 ml) at −10° C. was added dropwise a solution of N-bromosuccinimide (9.4 g, 0.054 mole) in dimethylformamide (50 ml) over 10 minutes. The reaction mixture was stirred at 0° C. for 15 minutes. The solution was added slowly to water (1 l) with vigorous stirring. The solid was filtered, dried, and dissolved in dichloromethane (300 ml). The solution was added to boiling methanol (1 l). The precipitate was collected by filtration to give 12.7 g (68%) of product, mp 150°–152° C.

ANALYSIS: Calculated for $C_{14}H_{10}Br_2N_2O_2$: 42.24%C 2.53%H 7.04%N. 42.23%C 2.58%H 7.05%N.

EXAMPLE 74

1-(2-Amino-4-bromophenyl)-5-bromoindoline hydrochloride

To a warm solution of 1-(2-nitro-4-bromophenyl)-5-bromoindoline (8.5 g, 21.3 mmoles) in dimethylformamide (80 ml) was added boiling ethanol (160 ml) and 1% platinum/carbon (1 g, wet in ethanol). The mixture was shaken under an initial pressure of 59 psi of hydrogen for 15 minutes. The mixture was filtered, the filter cake rinsed with ethanol and the filtrate was concentrated to dryness under reduced pressure at 55° C. The residue was dissolved into ether (150 ml) and the mixture was filtered. To form the hydrochloride salt, the filtrate was treated with a solution of methanol (20 ml) and acetyl chloride (2 g), prepared at 0° C., with stirring, to give 7.5 g (87%) of product. Recrystallization from ethanol and ether afforded the analytical sample, mp 183°–185° C.

ANALYSIS: Calculated for $C_{14}H_{12}Br_2N_2.HCl$: 41.57%C 3.24%H 6.92%N. Found: 41.86%C 3.12%H 6.90%N.

EXAMPLE 75

N-[2-(5-bromoindolin-1-yl)-5-bromophenyl]-4-methyl-1-piperazinecarboxamide

N-Bromosuccinimide (2.6 g, 14.5 mmoles) was added to a solution of N-[2-(indolin-1-yl)-5-bromophenyl]-4-methyl-1-piperazinecarboxamide (5.0 g, 12.0 mmoles) in dimethylformamide (50 ml). The solution was stirred at room temperature for 15 minutes and at 60° C. for 15 minutes. The solution was cooled and poured into dichloromethane (500 ml). The layers were separated and the organic phase was washed with water (3×500 ml), brine (500 ml), and dried over anhydrous sodium sulfate. The mixture was filtered and the filtrate was concentrated. The residue was purified by chromatography over silica gel (60 g, eluted with 4% methanol:96% dichloromethane, 1 l). The appropriate fractions were pooled and concentrated to give 4.8 g (84%) of product. Recrystallization from chloroform and hexane gave the analytical sample, mp 118°–119.5° C.

ANALYSIS: Calculated for $C_{20}H_{22}Br_2N_4O$: 48.60%C 4.49%H 11.34%N. Found: 48.21%C 4.56%H 11.30%N.

EXAMPLE 76

4,9-Dibromo-6-(4-methyl-1-piperazinyl)-1,2-dihydrobenzo[b]pyrrolo[3,2,1-jk][1,4]benzodiazepine A solution of N-[2-(5-bromo-1-indolinyl)-5-bromophenyl]-4-methyl-1-piperazinecarboxamide (12.3 g, 24.8 mmoles) and phosphorus oxychloride (250 ml) was heated under reflux for 1 hour. The reaction mixture was cooled and then concentrated at 50°–60° C. under vacuum. Ice-chilled sodium hydroxide solution (15%, 500 ml) and dichloromethane (500 ml) was added to the reaction mixture. The mixture was stirred for 20 minutes. The organic phase was separated and the aqueous phase was extracted once with dichloromethane (250 ml). The combined dichloromethane solutions were washed with 1N sodium hydroxide solution (350 ml) and brine (2×350 ml), dried over anhydrous sodium sulfate and filtered. The filtrate was evaporated. The residue was purified on a silica gel column (250 gm), eluted with 2% and then 3% methanol:dichloromethane. The appropriate fractions were combined and concentrated to give 8.3 g (70%) of product. Recrystallization from isopropanol gave the analytical sample, mp 215°–216° C.

ANALYSIS: Calculated for $C_{20}H_{20}Br_2N_4.0.5H_2O$: 49.50%C 4.36%H 11.54%N. Found: 49.31%C 4.19%H 11.55%N.

EXAMPLE 77

4,9-Dibromo-6-(4-methyl-1-piperazinyl)benzo[b]pyrrolo[3,2,1-jk][1,4]benzodiazepine A mixture 4,9-dibromo-6-(4-methyl-1-piperazinyl)-1,2-dihydrobenzo[b]pyrrolo[3,2,1-jk][1,4]-benzodiazepine (4.5 g, 9.45 mmoles) and manganese(IV) dioxide (7.0 g) in chloroform (150 ml) was heated under reflux for 3.5 hours. An additional 4.5 g of manganese dioxide was added. The reaction mixture was stirred overnight at room temperature. The mixture was filtered through celite and the filtrate was concentrated. The residue was purified by flash chromatography over a silica gel column (140 gm), eluted with 2% methanol:98% dichloromethane (2 l). The appropriate fractions were collected and evaporated. Crystallization of the residue from isopropanol (10 ml) yielded 3.37 g (75%) of product, mp 158°–159° C.

ANALYSIS: Calculated for $C_{20}H_{18}Br_2N_4$: 50.66%C 3.83%H 11.81%N. Found: 50.48%C 3.99%H 11.76%N.

EXAMPLE 78

6-Bromo-1-(2-nitrophenyl)-1,2,3,4-tetrahydroquinoline

A stirred solution, under nitrogen, of 1-(2-nitrophenyl)-1,2,3,4-tetrahydroquinoline (76.3 g, 0.30 mole) in dimethylformamide (1000 ml) was cooled to −10° C. A solution of of N-bromosuccinimide (58.7 g, 0.33 mole) in dimethylformamide (250 ml) was added dropwise at such a rate as to keep the reaction temperature below 0° C. (1.5 hours). Half-an hour after the addition was completed, the reaction mixture was poured into 7 liters of 2N-sodium hydroxide solution/ice, with stirring. The product separated as an oil. The quench fluids were decanted and the oil was rinsed several times with water. The oil was dissolved in dichloromethane (1.5 l). The organic solution was extracted once with 2N-sodium hydroxide solution, thrice with water, dried over sodium sulfate and concentrated. The residue was dissolved in 1:1 hexane:toluene (250 ml) and the solution was absorbed on a chromatography column containing 2 kg of silica gel packed in 1:1 hexane:toluene. Elution with this solvent mixture provided 82.7 g (82%) of product, as an oil. For analysis, a sample was Kugelrohr distilled at a vessel temperature of 166°–168° C. (0.2 mm Hg).

ANALYSIS: Calculated for $C_{15}H_{13}BrN_2O_2$: 54.07%C 3.93%H 8.41%N. Found: 53.73%C 4.30%H 8.35%N.

EXAMPLE 79

1-(2-Aminophenyl)-6-bromo-1,2,3,4-tetrahydroquinoline maleate

A Parr hydrogenation bottle was charged with 6-bromo-(2-nitrophenyl)-1,2,3,4-tetrahydroquinoline (16.7 g, 0.050 mole), 1% platinum-on-carbon (1 g), benzene (100 ml) and ethanol (100 ml). The mixture was shaken under an initial hydrogen pressure of 58 psi until uptake ceased. The mixture was then filtered to remove the catalyst and the filtrate was concentrated under vacuum. The residue was taken up in hot ether (150 ml), filtered, and the filtrate was treated with a hot solution of maleic acid (6.4 g, 0.055 mole) in ether (500 ml). The solution was boiled down to about 300 ml and allowed to cool. The supernatant was decanted from an oil, which separated. The supernatant was concentrated and the process was repeated several times to give 11.4 g (55%) of product. Recrystallization from ethyl acetate afforded the analytical sample, mp 113°–116° C.

ANALYSIS: Calculated for $C_{15}H_{15}BrN_2.C_4H_4O_4$: 54.42%C 4.57%H 6.68%N. Found: 54.40%C 4.60%H 6.64%N.

EXAMPLE 80

4-Methyl-N-[2-(6-bromo-1,2,3,4-tetrahydro-1-quinolinyl)phenyl]piperazinecarboxamide maleate A stirred solution, under nitrogen, of 1-(2-aminophenyl)-6-bromo-1,2,3,4-tetrahydroquinoline (21.2 g, 0.070 mole) and triethylamine (10.1 g, 0.10 mole) in dichloromethane (200 ml) was cooled to 0° C. Then there was added dropwise phenylchloroformate (15.7 g, 0.10 mole) at such a rate as to keep the reaction temperature below 5° C. The addition took 30 minutes. The mixture was stirred for 1 hour at ice-bath temperature, 2 hours at room temperature, and N-methylpiperazine (28.1 g, 0.28 mole) dissolved in dichloromethane (30 ml) was added dropwise over a 45 minute period. The solution was stirred for 3 hours and an additional charge of N-methylpiperazine (14.05 g, 0.14 mole) dissolved in dichloromethane (15 ml) was added, and the mixture was stirred overnight. Water (250 ml) was added with vigorous stirring. The layers were separated and the organic phase was washed twice with water, dried over anhydrous sodium sulfate and concentrated. The residue was dissolved in ethanol (200 ml), with heating, and treated with a warm solution of maleic acid (8.93 g, 0.077 mole) in ethanol (100 ml). The maleate salt was collected to give 23.2 g (61%) of product. Recrystallization from methanol afforded the analytical sample, mp 172°–174° C.

ANALYSIS: Calculated for $C_{21}H_{25}BrN_4O \cdot C_4H_4O_4$: 55.05%C 5.36%H 10.27%N. Found: 55.15%C 5.34%H 10.34%N.

EXAMPLE 81

5-Bromo-7-(4-methyl-1-piperazinyl)-2,3-dihydro-1H-quino[1,8-ab][1,5]benzodiazepine A stirred mixture of 4-methyl-N-[2-(6-bromo-1,2,3,4-tetrahydro-1-quinolinyl)phenyl]piperazine-carboxamide (14.2 g, 0.0330 mole) in phosphorus oxychloride (250 ml) was heated under reflux under nitrogen for 5 hours. The reaction mixture was cooled to room temperature and excess phosphorous oxychloride was removed at aspirator pressure with heating. The residue was chilled in an ice-bath (with exclusion of moisture), and treated with ice-cold 2N sodium hydroxide solution (250 ml) and dichloromethane (500 ml). The mixture was stirred, the organic phase was separated, washed with 2N sodium hydroxide solution, twice with water, dried over anhydrous sodium sulfate, and concentrated in vacuo. The residue was digested in boiling methanol (40 ml) to afford 10.7 g (79%) of product. Recrystallization from ethanol provided the analytical sample, mp 181°–183° C.

ANALYSIS: Calculated for $C_{21}H_{23}BrN_4$: 61.31%C 5.64%H 13.62%N. Found: 61.14%C 5.75%H 13.68%N.

EXAMPLE 82

1-(4-Bromo-2-nitrophenyl)-1,2,3,4-tetrahydroquinoline

A stirred mixture, under nitrogen, of 2,5-dibromonitrobenzene (140.5 g, 0.50 mole), 1,2,3,4-tetrahydroquinoline (133.2 g, 1.00 mole) and symmetrical collidine (121.2 g, 1.00 mole) in 1,2,3-trimethylbenzene (500 ml) as solvent was heated at 160°–165° C. for 7 days. The mixture was cooled to room temperature, filtered, and the filtrate was concentrated in vacuo (100° C.). The residue was taken up in dichloromethane (1.5 l) and the solution was extracted three times with dilute hydrochloric acid, once with dilute sodium hydroxide solution, three times with water, dried over anhydrous sodium sulfate and concentrated. This residue was dissolved in 1:1 hexane:toluene (250 ml) and adsorbed on a chromatography column containing 3 kg of silica gel. Elution with 1:1 hexane:toluene gave 30 g (18%) of product, as an oil. A portion of the oil was Kugelrohr distilled at an oven-temperature of 163°–165° C. (0.1 mm Hg) to provide the analytical sample.

ANALYSIS: Calculated for $C_{15}H_{13}BrN_2O_2$: 54.07%C 3.93%H 8.41%N. Found: 53.99%C 4.02%H 8.31%N.

EXAMPLE 83

1-(4-Bromo-2-aminophenyl)-1,2,3,4-tetrahydroquinoline 1-(4-Bromo-2-nitrophenyl)-1,2,3,4-tetrahydroquinoline (11.6 g, 0.035 mole) was dissolved in benzene (125 ml), and ethanol added (75 ml), followed by 1% platinum-on-charcoal (0.40 g). The mixture was shaken under an initial pressure of 56 psi for 6.5 hours. The mixture was filtered and the filtrate was evaporated at 50° C. under vacuum to provide 10.6 g (100%) of product, as a gum.

EXAMPLE 84

4-Methyl-N-[5-bromo-2-(1,2,3,4-tetrahydro-1-quinolinyl)phenyl]piperazinecarboxamide 1-(4-Bromo-2-aminophenyl)-1,2,3,4-tetrahydroquinoline (10.6 g, 0.035 mole) was dissolved on a steam bath in dichloromethane (150 ml). The solution was cooled to −5° C. in ice/methanol and triethylamine (5.01 g, 0.050 mole) was added in one portion, followed by a solution of phenylchloroformate (7.85 g, 0.050 mole) dissolved in dichloromethane (10 ml), dropwise over 15 minutes. The mixture was stirred 1 hour in the cold, 2 hours at room temperature, and an additional charge of phenylchloroformate (1.57 g, 0.010 mole) was added. After one hour, a solution of N-methylpiperazine (14.1 g, 0.14 mole) dissolved in dichloromethane (15 ml) was added over 0.5 hour. The reaction mixture was stirred under nitrogen at room temperature overnight. Water (100 ml) was added and the mixture was stirred 0.5 hour. The organic phase was separated, washed 4 times with water, dried over anhydrous sodium sulfate, and evaporated in a 100° C. bath in vacuo. The residue was dissolved in toluene (40 ml), adsorbed on a column of silica gel (500 g) packed in toluene and eluted with dichloromethane-methanol (98:2). The appropriate fractions were combined and evaporated to give 9.2 g (61%) of product, as an oil.

EXAMPLE 85

10-Bromo-7-(4-methyl-1-piperazinyl)-2,3-dihydro-1H-quino[1,8-ab][1,5]benzodiazepine A stirred solution of 4-methyl-N-[5-bromo-2-(1,2,3,4-tetrahydro-1-quinolinyl)phenyl]piperazinecarboxamide (8.6 g, 0.020 mole) in phosphorus oxychloride (200 ml) was heated under reflux under nitrogen for 6 hours. The reaction mixture was cooled to room temperature and excess phosphorus oxychloride was removed at aspirator pressure with heating. The residue was chilled in an ice-bath (with exclusion of moisture), and treated with ice-cold 2N sodium hydroxide solution (250 ml) and dichloromethane (250 ml). The mixture was stirred and triturated until the residue dissolved. The organic phase was separated, washed again with 2N sodium hydroxide solution, twice with water, dried over sodium sulfate, and concentrated in vacuo. The residue was taken up in 4N hydrochloric acid (100 ml), filtered, and the filrate was stirred 15 minutes with charcoal. After filtration, the solution was stirred with dichloromethane (100 ml), and the mixture was made alkaline by the addition of cold 2N sodium hydroxide solution. The organic phase was separated, washed twice with water, dried over sodium sulfate, and boiled 15 minutes with charcoal. After filtration, the solution was concentrated to give 4.6 g (56%) of product, as an oil, which crystallized on standing. The product was taken up in boiling methanol (20 ml) and allowed to crystallize first at room temperature, then in the refrigerator. Recrystallization from methanol afforded the analytical sample, mp 153°–156° C.

ANALYSIS: Calculated for $C_{21}H_{23}BrN_4$: 61.31%C 5.64%H 13.62%N. Found: 61.13%C 5.66%H 13.56%N.

EXAMPLE 86

4-Methyl-N-[2-(1,2,3,4-tetrahydro-1-quinolinyl)-phenyl]piperazinecarboxamide maleate A stirred solution, under nitrogen of 1-(2-aminophenyl)-1,2,3,4-tetrahydroquinoline (4.50 g, 0.020 mole), and triethylamine (3.04 g, 0.030 mole) in dichloromethane (50 ml) was cooled to 0° C. and phenylchloroformate (4.70 g, 0.030 mole) was added dropwise at such a rate such as to keep the reaction temperature below 5° C. The addition took 10 minutes. The mixture was stirred for 1 hour at ice-bath temperature, 1 hour at room temperature, and N-methylpiperazine (8.02 g, 0.080 mole) was added dropwise over a 5 minute period. The solution was stirred for 2 hours, N-methyl-piperazine (4.01 g, 0.040 mole) was added and the solution was stirred overnight. Water (100 ml) was added with vigorous stirring. The layers were separated, and the organic phase was washed twice with water, dried over anhydrous sodium sulfate and concentrated in vacuo. The residue was dissolved in ethanol (100 ml) and treated with a warm solution of maleic acid (2.6 g 0.022 mole) in ethanol (15 ml). The precipitate was collected to provide 6.1 g (65%) of product. Recrystallization from methanol afforded the analytical sample, mp 171°–173° C. dec.

ANALYSIS: Calculated for $C_{21}H_{26}N_4O \cdot C_4H_4O_4$: 64.36%C 6.48%H 12.01%N. Found: 64.29%C 6.44%H 12.01%N.

EXAMPLE 87

7-(4-Methyl-1-piperazinyl)-2,3-dihydro-1H-quino[1,8-ab][1,5]benzodiazepine

A stirred mixture of 4-methyl-N-[2-(1,2,3,4-tetrahydro-1-quinolinyl)phenyl]piperazinecarboxamide (15.9 g, 0.0450 mole) in phosphorus oxychloride (300 ml) was heated to reflux under nitrogen. The reaction mixture was heated under reflux for 5 hours, cooled to room temperature and evaporated at aspirator pressure with heating. The residue was chilled in an ice-bath (with exclusion of moisture), and treated with ice-cold 2N-sodium hydroxide solution (500 ml) and with dichloromethane (500 ml). The mixture was stirred and triturated until the residue dissolved. The organic phase was separated, washed with 2N sodium hydroxide solution, twice with water, dried over anhydrous sodium sulfate, and filtered. Concentration of the residue in vacuo gave 13.7 g (92%) of product. Recrystallization from ethanol gave the analytical sample, mp 129°–132° C.

ANALYSIS: Calculated for $C_{21}H_{24}N_4$: 75.87%C 7.28%H 16.85%N. Found: 76.04%C 7.44%H 16.52%N.

We claim:

1. A compound of the formula

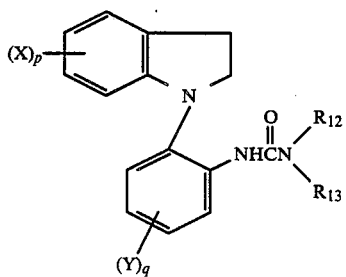

-continued

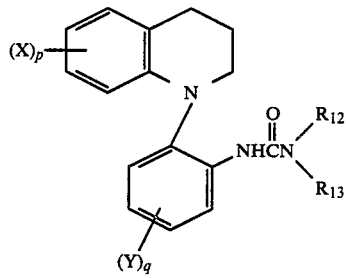

wherein X and Y may be the same or different and each is hydrogen, halogen, $CF_3$, lower alkyl, lower alkoxy, lower alkylthio or lower alkylsulfonyl, p and q are independently 1 or 2; $R_{12}$ and $R_{13}$ are lower alkyl; and $R_{12}$ and $R_{13}$ taken together with the nitrogen atom to which they are attached form a group of the formula

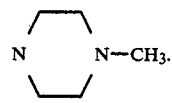

2. A compound as defined in claim 1 wherein $R_{12}$ and $R_{13}$ taken together with the nitrogen atom to which they are attached form a group of the formula

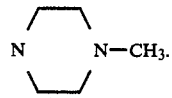

3. The compound as defined in claim 2 which is N-[5-chloro-2-(2,3-dihydro-1H-indol-1-yl)phenyl]-4-methyl-1-piperazinecarboxamide.

4. The compound as defined in claim 2 which is N-[5-methylsulfonyl-2-(2,3-dihydro-H-indol-1-yl)phenyl]-4-methyl-1-piperazinecarboxamide.

5. The compound as defined in claim 2 which is N-[5-methylthio-2-(2,3-dihydro-1H-indol-1-yl)phenyl]-4-methyl-1-piperazinecarboxamide.

6. The compound as defined in claim 2 which is N-[2-(2,3-dihydro-1H-indol-1-yl)-5-methoxyphenyl]-4-methyl-1-piperazinecarboxamide.

7. The compound as defined in claim 2 which is N-[5-chloro-2-(2,3-dihydro-5-chloro-1H-indol-1-yl)phenyl]-4-methyl-1-piperazinecarboxamide.

8. The compound as defined in claim 2 which is N-[2-(2,3-dihydro-1H-indol-1-yl)phenyl]-4-methyl-1-piperazinecarboxamide.

9. The compound as defined in claim 2 which is N-[2(2,3-dihydro-1H-indol-1-yl)-5-(α,α,α-trifluoromethyl)phenyl]-4-methyl-1-piperazinecarboxamide.

10. The compound as defined in claim 2 which is N-[5-methyl-2-(2,3-dihydro-1H-indol-1-yl)phenyl]-4-methyl-1-piperazinecarboxamide.

11. The compound as defined in claim 2 which is N-[5-bromo-2-(2,3-dihydro-1H-indol-1yl)phenyl]-4-methyl-1-piperazinecarboxamide.

12. The compound as defined in claim 2 which is N-[2-(2,3-dihydro-1H-indol-1-yl)5-fluorophenyl]4-methyl-1-piperazinecarboxamide.

13. The compound as defined in claim 2 which is N-[2-(5-chloro-2,3-dihydro-1H-indol-1-yl)phenyl]-4-methyl-1-piperazinecarboxamide.

14. The compound as defined in claim 1 which is N-[5-bromo-2-(2,3-dihydro-1H-indol-1-yl)phenyl]-N',N'-dimethylurea.

15. The compound as defined in claim 2 which is N-[2(5-bromo-1-indolinyl)phenyl]-4-methyl-1-piperazinecarboxamide.

16. The compound as defined in claim 2 which is N-[2(5-bromo-1-indolinyl)-5-methylphenyl]-4-methyl-1-piperazinecarboxamide.

17. The compound as defined in claim 2 which is N-[2(5-bromo-2-(2,3-dihydro-1H-indol-1yl)phenyl]-4-methyl-1-piperazinecarboxamide.

18. The compound as defined in claim 2 which is 4-methyl-N-[2(6-bromo-1,2,3,4-tetrahydro-1-quinolinyl)phenyl]piperazinecarboxamide.

19. The compound as defined in claim 2 which is 4-methyl-N-[5-bromo-2-(1,2,3,4-tetrahydro-1,2,3,4-tetrahydro-1-quinolinyl)phenyl]piperazinecarboxamide.

20. The compound as defined in claim 2 which is 4-methyl-N-[2-(1,2,3,4-tetrahydro-1-quinolinyl)phenyl]piperazinecarboxamide.

* * * * *

UNITED STATES PATENT AND TRADEMARK OFFICE
CERTIFICATE OF CORRECTION

PATENT NO. : 4,723,007
DATED : Feb. 2, 1988
INVENTOR(S) : Edward J. Glamkowski & Yulin Chiang It is certified that error appears in the above-identified patent and that said Letters Patent is hereby corrected as shown below:

Face of Patent should read:

Related U.S. Application Data

[60] "continuation-in-part of Ser. No. 495,569, May 18, 1983, abandoned" should be -- continuation-in-part of Ser. No. 495,569, May 18, 1983. --

Signed and Sealed this

Twenty-third Day of August, 1988

Attest:

DONALD J. QUIGG

*Attesting Officer*　　　　*Commissioner of Patents and Trademarks*